US012653572B2

(12) United States Patent
Litke et al.

(10) Patent No.: US 12,653,572 B2
(45) Date of Patent: Jun. 16, 2026

(54) SINGLE PORT INSTRUMENT ACCESS DEVICE

(71) Applicant: Intuitive Surgical Operations, Inc., Sunnyvale, CA (US)

(72) Inventors: Ronald G. Litke, Sandy Hook, CT (US); Jake A. Luckman, New Haven, CT (US); Jeffrey D. Brown, Palo Alto, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 830 days.

(21) Appl. No.: 17/764,893

(22) PCT Filed: Sep. 30, 2020

(86) PCT No.: PCT/US2020/053577
§ 371 (c)(1),
(2) Date: Mar. 29, 2022

(87) PCT Pub. No.: WO2021/067461
PCT Pub. Date: Apr. 8, 2021

(65) Prior Publication Data
US 2022/0401125 A1 Dec. 22, 2022

Related U.S. Application Data

(60) Provisional application No. 62/908,501, filed on Sep. 30, 2019.

(51) Int. Cl.
*A61B 17/34* (2006.01)
*A61B 17/00* (2006.01)
*A61B 17/02* (2006.01)

(52) U.S. Cl.
CPC ...... *A61B 17/3423* (2013.01); *A61B 17/0218* (2013.01); *A61B 2017/00477* (2013.01);
(Continued)

(58) Field of Classification Search
CPC ............ A61B 17/3423; A61B 17/0218; A61B 2017/00477; A61B 2017/3445;
(Continued)

(56) References Cited

U.S. PATENT DOCUMENTS

| | | | |
|---|---|---|---|
| 8,021,296 B2 | 9/2011 | Bonadio et al. | |
| 9,271,753 B2 | 3/2016 | Butler et al. | |
| (Continued) | | | |

FOREIGN PATENT DOCUMENTS

| | | |
|---|---|---|
| CN | 101822554 A | 9/2010 |
| CN | 101822556 A | 9/2010 |
| (Continued) | | |

OTHER PUBLICATIONS

International Preliminary Report on Patentability for Application No. PCT/US2020/053577, mailed Apr. 14, 2022, 11 pages.
(Continued)

*Primary Examiner* — Theodore J Stigell
(74) *Attorney, Agent, or Firm* — Schwegman, Lundberg & Woessner, P.A.

(57) ABSTRACT

Disclosed are medical devices for surgical procedures, especially procedures that involve the manipulation of surgical instrument end effectors close to the skin surface at an incision site. In accordance with some embodiments, an instrument access device is configured to couple to a wound retractor at a distal end of the device and to receive a multiple instrument entry guide in a port at the proximal end of the instrument access device, with an envelope between the distal and proximal ends defining a sealed cavity for maintaining insufflation pressure. Various embodiments provide means for rotating an assistant port in the envelope about a port that receives the instrument entry guide without twisting the envelope. Also disclosed are various envelope (Continued)

shapes. Also disclosed is an instrument entry guide that aligns surgical instrument shafts.

21 Claims, 35 Drawing Sheets

(52) U.S. Cl.
CPC ................. *A61B 2017/3445* (2013.01); *A61B 2017/3466* (2013.01); *A61B 2217/002* (2013.01)

(58) Field of Classification Search
CPC ...... A61B 2017/3466; A61B 2217/002; A61B 34/35; A61B 17/3498; A61B 17/3474; A61B 90/40; A61B 2017/3452; A61B 2034/302
See application file for complete search history.

(56) References Cited

U.S. PATENT DOCUMENTS

| | | | |
|---|---|---|---|
| 9,820,771 | B2 | 11/2017 | Norton et al. |
| 10,582,948 | B2 | 3/2020 | Norton et al. |
| 10,874,427 | B2 | 12/2020 | Norton et al. |
| 11,202,653 | B2 | 12/2021 | Bonadio et al. |
| 11,298,153 | B2 | 4/2022 | Norton et al. |
| 11,771,460 | B2 | 10/2023 | Bonadio et al. |
| 12,213,700 | B2 | 2/2025 | Bonadio et al. |
| 2010/0312063 | A1 | 12/2010 | Hess et al. |
| 2011/0015491 | A1* | 1/2011 | Ravikumar .............. A61B 1/32 600/233 |
| 2018/0338777 | A1 | 11/2018 | Bonadio et al. |

FOREIGN PATENT DOCUMENTS

| | | | |
|---|---|---|---|
| EP | | 2226027 A1 | 9/2010 |
| WO | WO-2014144233 A1 | | 9/2014 |

OTHER PUBLICATIONS

International Search Report and Written Opinion for Application No. PCT/US2020/053577, mailed Dec. 17, 2020, 12 pages.

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

Office Action for Chinese Application No. CN202080067603, mailed Jun. 30, 2025, 6 pages.

* cited by examiner

1000

1054

1026

1100

1100

1054

1102

SINGLE PORT INSTRUMENT ACCESS DEVICE

CLAIM OF PRIORITY

This application is a U.S. National Stage Filing under 35 U.S.C. 371 from International Application No. PCT/US2020/053577, filed on Sep. 30, 2020, and published as WO 2021/067461 A1 on Apr. 8, 2021, which claims the benefit of priority to U.S. Provisional Patent Application No. 62/908,501, filed on Sep. 30, 2019, each of which is incorporated by reference herein in its entirety.

TECHNICAL FIELD

This document relates generally to medical devices, and more particularly, to medical devices for use in minimally invasive surgical procedures.

BACKGROUND

Surgical systems that operate at least in part with computer-assisted control ("telesurgical systems"), such as those employed for minimally invasive medical procedures, can include large and complex equipment to precisely control relatively small instruments. Such systems are sometimes referred to as robotic surgical systems or surgical robots. The da Vinci® Surgical Systems commercialized by Intuitive Surgical, Inc. are examples of telesurgical systems.

Various telesurgical system architectures exist. Some system architectures enable multiple (e.g., two, three, four, or more) surgical instruments to enter the body through a single body opening (surgical incision or natural orifice), and these systems are sometimes referred to as "single-port" systems (e.g., the da Vinci SP® Surgical System). Other system architectures enable multiple surgical instruments to enter the body individually at corresponding multiple locations, and these systems are sometimes referred to as "multi-port" systems (e.g., the da Vinci Xi® Surgical System). Persons of skill in the art will understand that multi-port systems may sometimes be configured during surgery to operate through a single natural body orifice, such as the mouth or anus, or through a single incision (e.g., Intuitive Surgical's Single Site® technology used with a da Vinci Xi® Surgical System). Persons of skill in the art will also understand that single- and multi-port configurations may be combined simultaneously in a single telesurgical system (e.g., two or more instruments inserted via one body opening, and one or more other instruments inserted via one or more corresponding other body openings).

Surgical instruments used during minimally invasive surgery typically include an endoscopic camera or therapeutic end effector mounted at the end of a long, slender instrument shaft. Since instrument end effectors are typically located deep within the body during surgery, telesurgical systems are designed to constrain rotation of the instrument at a point located on the instrument's shaft, often referred to as a remote center of motion. Either kinematic hardware structure or control system software design (or a combination of the two) may be used to impose this remote center of motion constraint. To minimize tissue trauma during surgery, the constrained remote center of motion is typically located at or near the body opening through which the instrument enters.

If a telesurgical system is to be used at or near the body opening, however, then several challenges exist. First, to provide sufficient distance between an instrument's constrained remote center of motion and its end effector, the constrained remote center of motion may need to be located proximally of the body opening, sometimes by several centimeters or more. Second, if part of the surgery is performed proximally of the ultimate surgical site (e.g., using the telesurgical system to perform dissection to reach the ultimate surgical site), there needs to be an easy way to relocate the constrained remote center of motion distally as the surgery progresses towards the deepest surgical site in the patient's body. A third challenge exists if insufflation is to be used in the body cavity in which the ultimate surgical site is located (e.g., the abdomen, the rectum). When the constrained remote center of motion is located at the patient's body wall, and when cannulas are used to introduce instruments past the body wall, seals in the cannulas are used to maintain insufflation gas pressure within the body cavity both when an instrument is inserted through the body wall via the cannula and when the instrument is removed from the cannula. But if the cannula is located proximal of the body opening, insufflation gas pressure must still be maintained.

Further, for a single-port system in which two or more instruments can be introduced into a patient and moved as a single instrument cluster, these challenges become more complex because the constrained remote centers of motion for the two or more instruments are located at the same point or close to one another. In addition, single-port system instruments may be designed with joints that allow them to be inserted close to one another, but then individually spread apart after passing beyond the body wall to provide triangulation to more effectively perform surgery. And, a further challenge exists during the use of a single-port system if an additional instrument (either a telesurgical system instrument or a manually operated instrument) is to be introduced to assist the surgery, because the cluster of single-port system instruments blocks some access locations of the additional instrument.

What is required, therefore, is a way to allow a single-port telesurgical system to be used with its constrained remote center of motion located proximally of the patient's body opening to perform surgery at or near the patient's body opening, to allow insufflation gas pressure to be maintained during this surgery, and also to allow an assist instrument to be introduced to any desired location in relation to the cluster of telesurgical system instruments during this surgery.

SUMMARY

Examples according to this disclosure include a medical device that allows a multiple instrument entry guide to be located outside a patient's body and that simultaneously provides a sealed space between the entry guide and an opening in the patient's body wall to maintain insufflation. In this description, such a medical device is referred to as an "instrument access device". The instrument access device includes an envelope, and the envelope includes a distal opening at a distal end, a proximal opening at a proximal end, and an interior cavity between the distal and proximal openings. The envelope may have various shapes, such as a spheroid shape, ellipsoid shape, ovoid shape, barrel shape, lenticular shape, or bellows shape, for example.

At the distal end, the envelope can be coupled to a medical port device, such as a wound retractor, via a distal coupling component (e.g., a clamp) at the distal opening. At the proximal end, the envelope can be coupled, via a proximal coupling component, to a telesurgical system. The proximal coupling component is configured to accommodate multiple surgical instruments through a single opening and seal against insufflation gas escaping through the single opening.

The instrument access device is optionally configured to receive an insufflation gas and to maintain insufflation pressure within a cavity in the body of a patient and within the interior cavity of the envelope. The pressurized and sealed envelope cavity provides an operating space for shafts of multiple instruments of a telesurgical system to articulate outside the patient's body such that instrument end effectors are located at or near the surface of the body at the port device coupled to the instrument access device.

The proximal coupling component of the instrument access device is located at and is coupled to the proximal opening of the envelope. In some examples, the proximal coupling component includes a first port and a second port. The first port may be, for example, configured to receive an entry guide receptacle and, in the entry guide receptacle, an instrument entry guide (also simply "entry guide"), while the second port may be, for example, an assistant port. The assistant port may, for instance, support the introduction of a manually-operated instrument, items required for surgery, and removal of large and/or delicate specimens during a procedure. The proximal coupling component includes a center, and the first and second ports are located eccentrically on the proximal coupling component.

In an example, an entry guide receptacle is received in the first port of the instrument seal assembly. The entry guide receptacle works similarly to a cannula that would be received in the wound in cases where the end effectors are located deep inside the body. In some examples, the entry guide receptacle includes an instrument entry guide seal, which is configured to receive and seal an instrument entry guide. Compared with instrument entry guides received in a cannula in the wound, the instrument entry guide received, remote from the wound, in the entry guide receptacle within the first port may be shortened.

Instrument access devices in accordance with this disclosure optionally also include a mechanism configured to rotate the second (e.g., assistant) port around the first port without the envelope twisting about a central axis of the envelope. In some examples, the mechanism includes a gear train. In another example, the mechanism includes a linkage. Additionally, in examples, the mechanism can include a clutch (may also be referred to as torque limiting clutch or torque limiter), which disengages at least part of the mechanism in response to a threshold applied torque.

This Summary is intended to provide an overview of subject matter of the present patent application. It is not intended to provide an exclusive or exhaustive explanation of the invention. The detailed description and accompanying drawings provide further information about various aspects of the inventive subject matter of the present patent application.

BRIEF DESCRIPTION OF THE DRAWINGS

In the drawings, which are not necessarily to scale, like numerals describe similar components in different views. Like numerals having different letter suffixes represent different instances of similar components. The drawings illustrate generally, by way of example, but not by way of limitation, various embodiments discussed in this document.

DETAILED DESCRIPTION

Figure 1A:
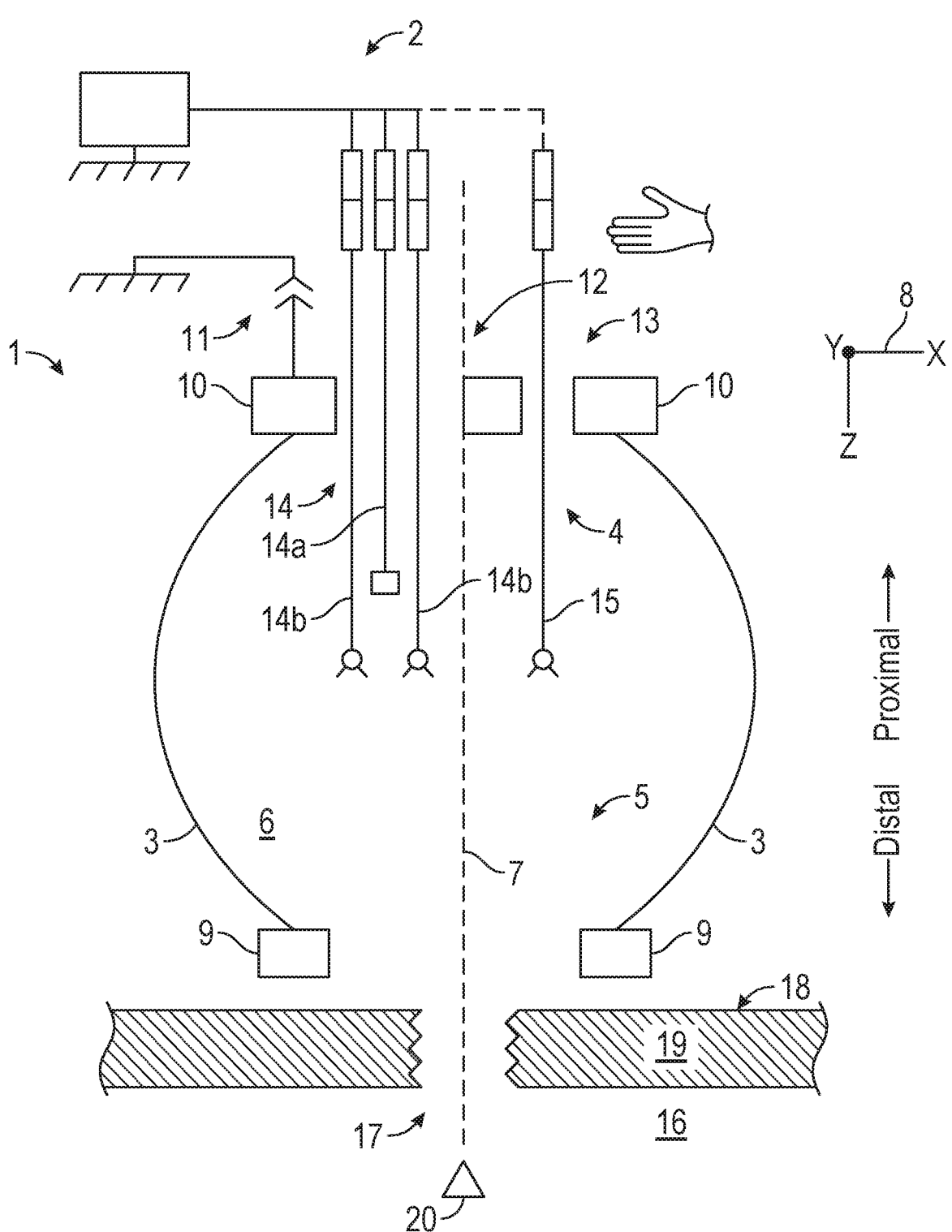
FIG. 1A is a schematic cross-sectional view of an instrument access device used together with a telesurgical system, in accordance with various embodiments.

FIGS. 1A-IE are schematic cross-sectional views that illustrate aspects of various embodiments of an instrument access device 1 that is used together with a telesurgical system 2. As shown in FIG. 1A, instrument access device 1 includes an envelope 3, which has a proximal opening 4 and a distal opening 5. The interior 6 of envelope 3 is empty so that one or more surgical instruments can be inserted through proximal opening 4 into the interior 6, and the instruments can pass through and exit interior 6 through distal opening 5. Envelope 3 may have various shapes as described in more detail below.

For reference, a center longitudinal axis 7 of instrument access device 1 and envelope 3 is defined extending through the proximal and distal openings 4,5. As illustrated, in this specification, locations associated with the instrument access device are denoted as "proximal" or "distal". The term "distal" means a location closer to a surgical site. The term "proximal" means a location farther away from the surgical site and, thus, closer to the mechanical ground of the telesurgical system 2. Similarly, as indicated by the arrows as shown, the—distal direction generally denotes the direction along the instrument access device away from the mechanical ground of telesurgical system 2 and towards a surgical site, and the proximal direction generally denotes the direction along the instrument access device away from the surgical site and towards the mechanical ground of telesurgical system 2. And for still further reference, a world reference frame 8 is arbitrarily defined and is fixed in space. Typically, the instrument access device 1, when in use, is oriented with its proximal opening 4 located above the distal opening 5 relative to the patient's body (i.e., the proximal opening being the "top opening", and the distal opening 5 being the "bottom opening"), as shown, such that surgery is performed from above. Note, however, that the instrument access device 1 can be used in any orientation.

Instrument access device 1 includes a distal coupling component 9 and a proximal coupling component 10. Distal coupling component 9 is coupled, optionally removably or fixedly, to envelope 3 at distal opening 5, and proximal coupling component 10 is coupled, optionally removably or fixedly, to envelope 3 at proximal opening 4.

As shown, proximal coupling component 10 is removably coupled to mechanical ground at a coupling 11. Any suitable coupling type may be used, and proximal coupling component 10 may be coupled, optionally, to mechanical ground via telesurgical system 2 (e.g., where telesurgical system 2 includes a proximal portion of coupling 11), via another piece of operating room equipment (e.g., an operating table), or via any other suitable supporting structure that allows proximal coupling component 10 to be placed at a desired position and orientation in space (i.e., with reference to frame 8; the combination of translational position and rotation orientation defining a unique pose of an object in three-dimensional space) and then be held stationary in that desired position and orientation during surgery performed with the use of telesurgical system 2.

As shown, proximal coupling component 10 includes a first opening 12 and a second opening 13. First opening 12 is sized to receive one or more telesurgical system instruments 14 of telesurgical system 2. A cluster of three telesurgical system instruments 14 is show—an endoscopic camera 14a and two therapeutic instruments 14b (e.g., grasping, cutting, or electrosurgical instruments, and the like). This instrument cluster is illustrative of various combinations of telesurgical system instruments 14 that may be received through first opening 12 into the interior 6 of envelope 3. Second opening 13 is sized to receive one or more assist instruments 15 (e.g., grasping, cutting, electrosurgical, suction/irrigation, or stapling instruments, and the like). In some implementations the one or more assist instruments 15 are manually operated (illustrated by the hand symbol), and in other optional implementations the one or more assist instruments 15 are operated via telesurgical system 2 (illustrated in dashed line connection). Although a single second opening 13 is shown, proximal coupling component 10 may optionally include two, three, or more second openings to receive various combinations of additional manual or teleoperated assist instruments.

Distal coupling component 9 is removably coupled to patient 16 and surrounds a body opening 17—either an incision or a natural orifice, such as the anus. During a surgical procedure, telesurgical system instruments 14 are received into envelope 3 and extend towards its distal opening 5. In this way, telesurgical system instruments 14 may work at the patient's skin surface 18, within the patient's body wall 19, or at a surgical site 20 distal of the body wall 19.

Figure 1B:
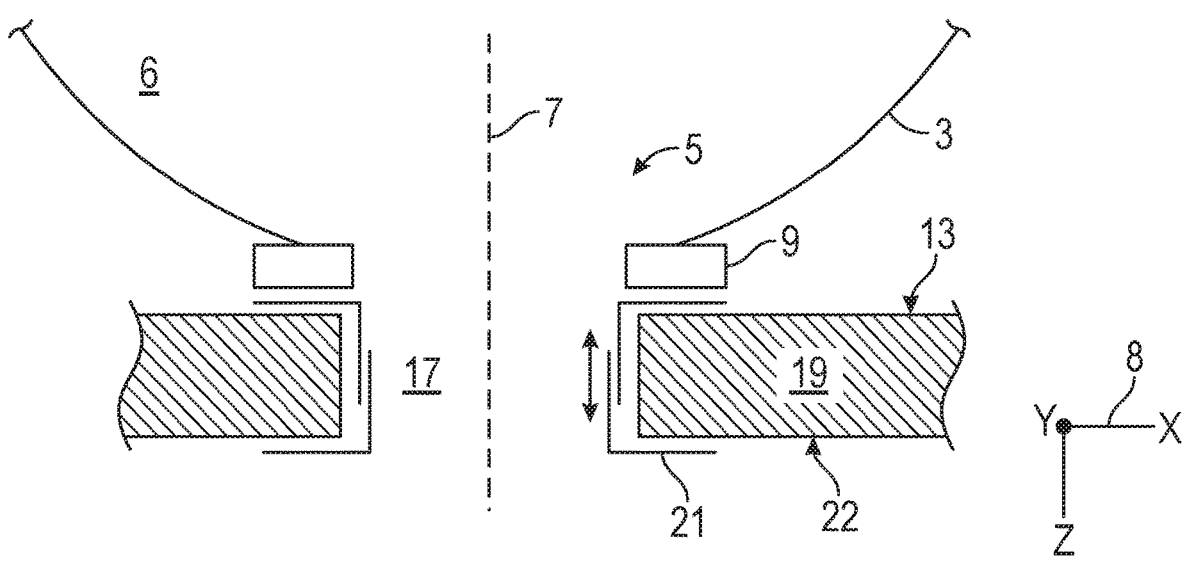
FIGS. 1B-1D are schematic cross-sectional views that illustrate in more detail coupling of the distal end of the instrument access device of FIG. 1A to a port device, in accordance with various embodiments.
Figure 1C:
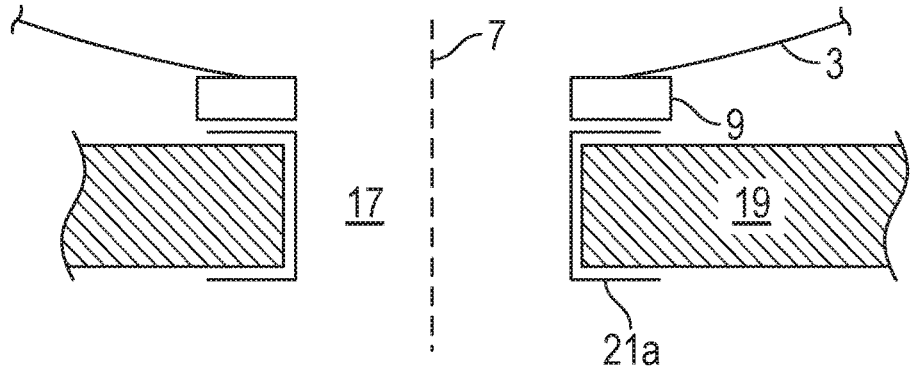
Figure 1D:
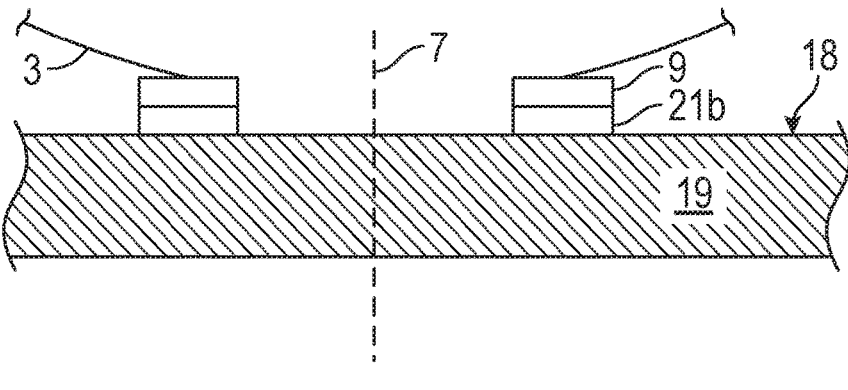

FIGS. 1B-1D are schematic cross-sectional views that illustrate in more detail the coupling of the distal end of instrument access device 1 to a port device 21 located at body opening 17 in a patient in various embodiments. Port device 21 retracts the patient's tissue and so keeps opening 17 open to allow surgical instruments to enter. As shown in FIG. 1B, port device 21 may have a generally fixed diameter and be adjustable in height as shown by the double-headed arrow so that it can be tightened against the patient's skin surface 18 and an interior surface 22 of body wall 19. (An example of this type of port device 21 is commonly referred to as a wound retractor, or by similar terms.) Alternatively, as shown in FIG. 1C, distal coupling component 9 may be removably or fixedly coupled to another type of port device 21a, which generally has a fixed diameter and a fixed height and is inserted into opening 17. (An example of this type of port device 21a is an anal port used during transanal surgery.) Alternatively, distal coupling component 9 may be removably or fixedly coupled to yet another type of port device 21b, which generally has a fixed diameter and a fixed height and is placed on the patient's skin surface, for example by adhesive or suction. If envelope 3 is sufficiently stiff, then a distally-directed force transmitted from proximal coupling component 10 (receiving, for example, a distally-directed force from telesurgical system 2) through envelope 3 may be sufficient to maintain port device 21b in position. Alternatively, a structural support (not shown) may be coupled to port device 21b and used to keep port device 21b in position. This type of port device 21b allows the surgical instruments to work at or slightly below the patient's skin surface (e.g., to make an incision or to dissect tissue immediately under the skin surface). Other variations of port devices optionally may be used. If the distal coupling component 9 is removably coupled to a port device, then distal coupling component 9 may be optionally coupled to any of port devices 21, 21*a*, or 21*b*, or to any other style of port device used during a surgical procedure. That is, a single instrument access device 1 may be used with any of two or more ports devices, depending on the surgery to be performed. Distal coupling component 9 optionally includes a clamp (not shown) or other suitable device that may be used to removably couple distal coupling component 9 to a port device. It should be noted that although gas pressure used to insufflate a body cavity for surgery can also be used to insufflate envelope 3, the instrument access device and associated components optionally may be used in clinical situations in which patient insufflation gas is not used, in which case insufflation gas may be used solely to hold envelope 3 in its desired shape or to otherwise provide clinical benefits such as smoke evacuation from within envelope 3.

Figure 1E:
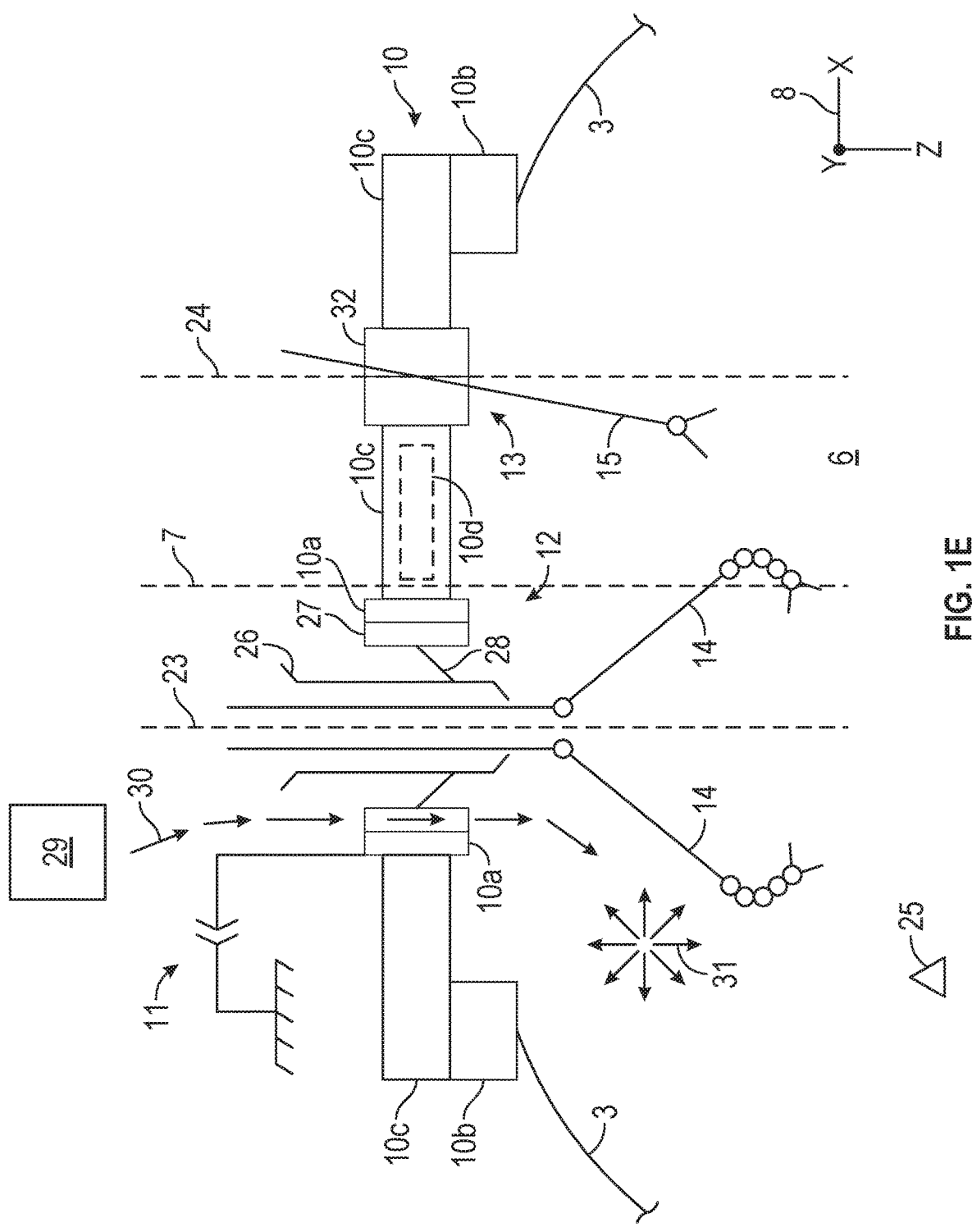
FIG. 1E is a schematic cross-sectional view that illustrates in more detail proximal elements of the instrument access device of FIG. 1, in accordance with various embodiments.

FIG. 1E is a schematic cross-sectional view that illustrates proximal elements of instrument access device 1 in more detail. During surgery, teleoperated instruments 14 are inserted through first opening 12 along telesurgical instrument insertion axis 23, and one or more assist instruments 15 are inserted through second opening 13 generally along assist instrument insertion axis 24. If it becomes necessary to insert an assist instrument 15 into envelope 3 to a location 25 that is blocked by one or more telesurgical instruments 14, then the position of second opening 13 must move with reference to the position of first opening 12 so that the assist instrument 15 can reach the desired location 25. Therefore, since first opening 12 and its associated telesurgical instrument insertion axis 23 are stationary with reference to global frame 8, second opening 13 and its associated assist instrument insertion axis 24 must orbit around first opening 12 (i.e., telesurgical instrument insertion axis 23) until second opening 13 and its associated assist instrument insertion axis 24 are at a position from which assist instrument 15 can reach the location 25. But, even though the distal coupling component 9 of envelope 3 is fixed with reference to frame 8 when coupled to a patient, envelope 3 should not twist around center axis 7 as second opening 13 and assist instrument insertion axis 24 orbit around first opening 12 and telesurgical instrument insertion axis 23.

In one aspect, telesurgical instrument insertion axis 23 is offset from center axis 7; in an alternate aspect, telesurgical instrument insertion axis 23 is coincident with center axis 7; in yet another alternate aspect, alternate instrument insertion axis 24 is offset from center axis 7; and in still another alternate aspect, alternate instrument insertion axis 24 is coincident with center axis 7. Therefore it can be seen that if one of the center axis 7, telesurgical instrument insertion axis 23, or assist instrument insertion axis 24 is held stationary in space, the other two axes if offset from the stationary axis will orbit around the stationary axis without envelope 3 twisting. It can also be seen that if the center axis 7 is coincident with telesurgical instrument insertion axis 23 or assist instrument insertion axis 24, then if the coincident axes are held stationary in space the remaining non-coincident axis will orbit around the coincident axes without envelope 3 twisting, and if the remaining non-coincident axis is held stationary in space, the coincident axes will orbit around the remaining non-coincident axis without envelope 3 twisting. Likewise, a similar relationship between fixed axes (single or coincident) and orbiting axes (single or coincident) exists for implementations in which two, three, or more optional second openings 13 are used. The following description concentrates on aspects in which the telesurgical instrument insertion axis is fixed in space and offset from center axis 7, to avoid prolix description; skilled persons will understand that the described implementations can easily be modified to similarly describe other implementations in which the center axis 7 or assist instrument insertion axis 24 is fixed in space, and other implementations that include coincident axes.

Figure 2:
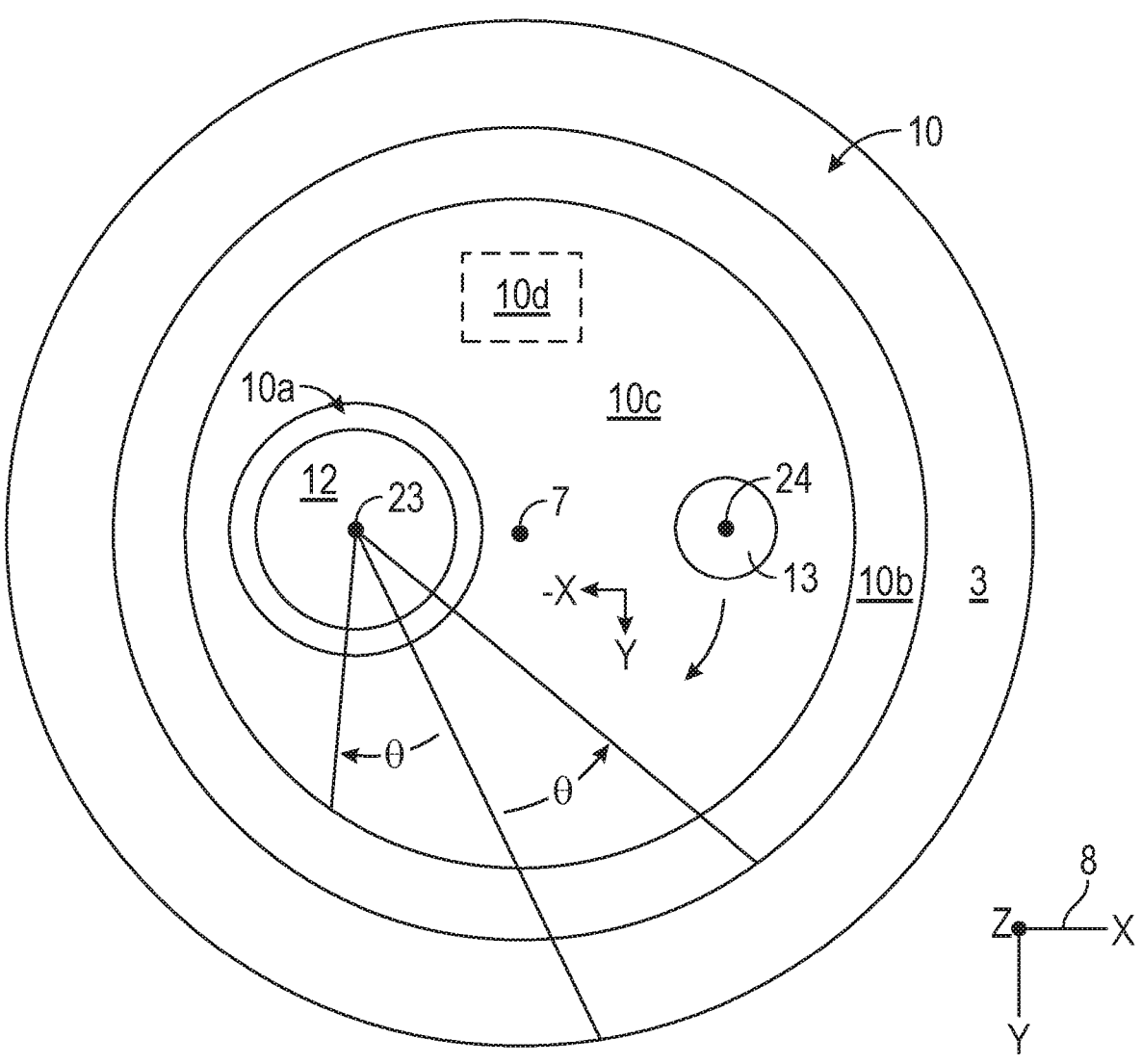
FIG. 2 is a schematic top view that illustrates operating features of proximal coupling component 10.

FIG. 2 is a schematic top view that illustrates operating features of proximal coupling component 10. Referring to FIGS. 1E and 2 together, proximal coupling component 10 includes an inner stationary element 10*a*, an outer element 10*b*, and an orbital element 10*c* between stationary element 10*a* and outer element 10*b*. Stationary element 10*a* is coupled to mechanical ground (e.g., via coupling 11 as described above) so that, during a surgical procedure, element 10*a* remains stationary at a desired position and orientation with reference to reference frame 8 until a clinician moves stationary element 10*a* to a different (second) desired position and orientation if necessary. Outer element 10*b* is coupled to envelope 3 at proximal opening 4 and remains stationary relative to proximal opening 4. Orbital element 10*c* is coupled to stationary element 10*a* and rotates around stationary element 10*a* at teleoperated instrument insertion axis 23.

During use, when the distal opening 5 is fixed in space (e.g., when distal coupling component 9 is coupled to a port device), envelope 3 will undesirably twist if proximal opening 4 is rotated. Therefore, orbital element 10*c* includes a countermotion mechanism 10*d* that is coupled to outer element 10*b*, so that, as orbital element 10*c* rotates in a first direction around stationary element 10*a* by an angular amount θ, countermotion mechanism 10*d* rotates outer element 10*b* relative to orbital element 10*c* by an equal angular amount θ but in an opposite direction of rotation from orbital element 10*c*'s direction of rotation around stationary element 10*a* (i.e., −θ). And since the two rotations are by equal angular amounts but in opposite directions, outer element 10*b*'s orientation does not change with reference to frame 8, and envelope 3 does not twist around center axis 7 when distal coupling component 9 is stationary with reference to frame 8. That is, proximal opening 4, distal opening 5, stationary element 10*a*, outer element 10*b* and distal coupling component 9 all remain in the same relative orientation to one another as orbital element 10*c* rotates with reference to them. It can further be seen that since stationary element 10*a* is fixed in space, outer element 10*b* and orbital element 10*c* translate in position with reference to frame 8 (−x, y, as shown for orbital element 10*c*'s rotation angle θ) as orbital element 10*c* orbits around stationary element 10*a*. But since envelope 3 is flexible or sufficiently movable with reference to distal opening 5 and distal coupling component 9, its proximal opening 4 can translate with reference to its distal opening 5 without any accompanying twisting of envelope 3 around center axis 7.

Referring to FIG. 1E, telesurgical instruments 14 are inserted through first opening 12 via an optional telesurgical instrument entry guide 26. Non-limiting examples of telesurgical system entry guides 26 that accommodate two or more telesurgical instruments 14 are disclosed in U.S. Pat. No. 9,877,744 B2 (filed Feb. 12, 2010)(disclosing "Entry Guide for Multiple Instruments in a Single Port Surgical System") and U.S. Pat. No. 9,757,149 B2 (filed Jun. 16, 2014) (disclosing "Surgical System Entry Guide"), and also in International Patent Application Pubs. No. WO 2018/ 013730 A1 (filed Jul. 12, 2017) (disclosing "Surgical Instrument Guide") and WO 2018/013734 A1 (filed Jul. 12, 2017)

(disclosing "Surgical Instrument Guide with Insufflation Channels"), all of which are incorporated herein by reference.

In some implementations, entry guide 26 is inserted through an optional entry guide receptacle 27, which is inserted through stationary element 10a and performs the function of an entry guide cannula. In other optional implementations, entry guide receptacle 27 is combined with or constitutes stationary element 10a, and entry guide 26 is inserted directly through stationary element 10a, which in this case performs the function of an entry guide cannula.

To prevent insufflation gas under pressure from leaking from interior 6 of envelope 3 through entry guide 26 with or without telesurgical instruments 14 inserted through entry guide 26, or through receptacle 27 (or stationary element 10a functioning as an entry guide receptacle) either with or without an entry guide 26 inserted through receptacle 27 (or stationary element 10a functioning as an entry guide receptacle), various gas seal arrangements may be used. Non-limiting examples of entry guide seals 28 are disclosed in U.S. Patent Application Pub. No. US 2014/0276464 A1 (filed Mar. 14, 2014)(disclosing "Sealing Multiple Surgical Instruments"), which is incorporated herein by reference.

Insufflation gas under pressure may be introduced into the interior 6 of envelope 3 via stationary element 10a, or via entry guide 26, or via receptacle 27, or via seal 28, or by an arrangement of any of these four elements combined together to define a gas flow path. For example, if aspects of stationary element 10a and receptacle 27 are combined into a single element and an entry guide seal 28 is used, insufflation gas may be introduced via these combined elements. As illustrated, insufflation gas from an insufflation gas source 29 travels along a gas flow path 30 into interior 6 of envelope 3. As a result, an insufflation gas pressure 31 higher than the ambient atmospheric pressure outside of envelope 3 is maintained in interior 6.

Alternatively, insufflation gas may be introduced into the interior 6 of envelope 3 via gas flow paths other than illustrated by gas flow path 30, such as an instrument seal in second opening 13 (described below), or such as a dedicated insufflation port in orbital element 10c, envelope 3, or distal coupling component 9. And optionally, one or more gas flow paths from interior 6 to outside envelope 3 may be defined, illustrated by the reverse direction of gas flow path 30. Such an outward gas flow path may be used for functions such as smoke evacuation if a teleoperated instrument 14 or an assist instrument 15 is not used to perform a smoke evacuation function.

Envelope 3 may have various shapes and may be made of various materials. For example, envelope 3 may have a generally spheroid shape, a generally ellipsoid shape (i.e., flattened or elongated with reference to center axis 7), a generally ovoid shape (i.e., tapered at one end along center axis 7), a generally cylindrical shape around center axis 7, or other three-dimensional shape of clinical benefit (e.g., generally conical, generally prism-shaped, and the like).

Envelope 3 may be made of flexible plastic sheeting that assumes the designed shape when sufficient insufflation gas pressure 31 exists within interior 6 of envelope 3. Optionally, envelope 3 may be made of a flexible, resilient material that holds its shape without the need for interior gas pressure. In still other options, structural elements (e.g., support ribs or similar structures) are used to help envelope 3 hold its shape during use. And in still other options, envelope is rigid.

Envelope 3 may be generally transparent so that a clinician outside envelope 3 may view the pose of an instrument

14, 15 within envelope 3. Alternatively, envelope 3 may be opaque, in which case an image from an endoscopic camera within envelope 3 may be used to determine the pose of an instrument 14, 15 within envelope 3. As another alternative, envelope 3 may be opaque with one or more transparent windows.

Still referring to FIG. 1E, an assist instrument 15 is inserted through second opening 13 via an assist instrument seal 32. Instrument seal 32 functions to maintain insufflation gas pressure within envelope 3 when an assist instrument 15 is either inserted or not inserted. Various suitable instrument seals are known and may be used, and non-limiting examples of an instrument seal 32 are disclosed in U.S. Patent Application Pub. No. 2017/0095269 A1 (filed Mar. 17, 2015) and in International Patent App. No. PCT/US2019/031393 (filed May 8, 2019) (disclosing "Instrument Seal"), which are incorporated herein by reference.

Further aspects and details will now be described.

Telesurgical System

To illustrate the general context in which an instrument access device as described above may be used, FIG. 3 provides a schematic perspective view that illustrates aspects of a telesurgical system in accordance with various embodiments. In general, for the purposes of this description, a telesurgical system includes three main components: an endoscopic imaging system, a user control system (master), and a manipulator system 210E (slave) (shown in FIG. 3), all interconnected by wired (electrical or optical) or wireless connections. One or more data processors (i.e., one or more logical units coupled to one or more memory systems) may be variously located in these main components to provide system functionality. Examples are disclosed in U.S. Pat. No. 9,060,678 (filed Jun. 13, 2007) (disclosing "Minimally Invasive Surgical System"), which is incorporated by reference herein.

The imaging system performs image processing functions on, e.g., captured endoscopic imaging data of the surgical site and/or preoperative or real-time image data from other imaging systems external to the patient. The imaging system outputs processed image data (e.g., images of the surgical site, as well as relevant control and patient information) to a surgeon at user control system. In some aspects, the processed image data is output to an optional external monitor visible to other operating room personnel or to one or more locations remote from the operating room (e.g., a surgeon at another location may monitor the video; live feed video may be used for training; etc.).

The user control system includes multiple-degrees-of-freedom mechanical input devices that allow the surgeon to manipulate the instruments, entry guide(s), and imaging system devices, with computer assistance. These input devices may in some aspects provide haptic feedback from the instruments and surgical device assembly components to the surgeon. The user control system also includes a stereoscopic video output display positioned such that images on the display are generally focused at a distance that corresponds to the surgeon's hands working behind/below the display screen.

Control during insertion and use of the instruments may be accomplished, for example, by the surgeon moving the instruments presented in the image with one or two of the input devices; the surgeon uses the input devices to translate and rotate the instrument in three-dimensional space. Similarly, one or more input devices may be used to translate and rotate the imaging system or an associated surgical device assembly to steer an endoscope or instrument cluster towards a desired location on the output display and to advance inside the patient.

Figure 3:
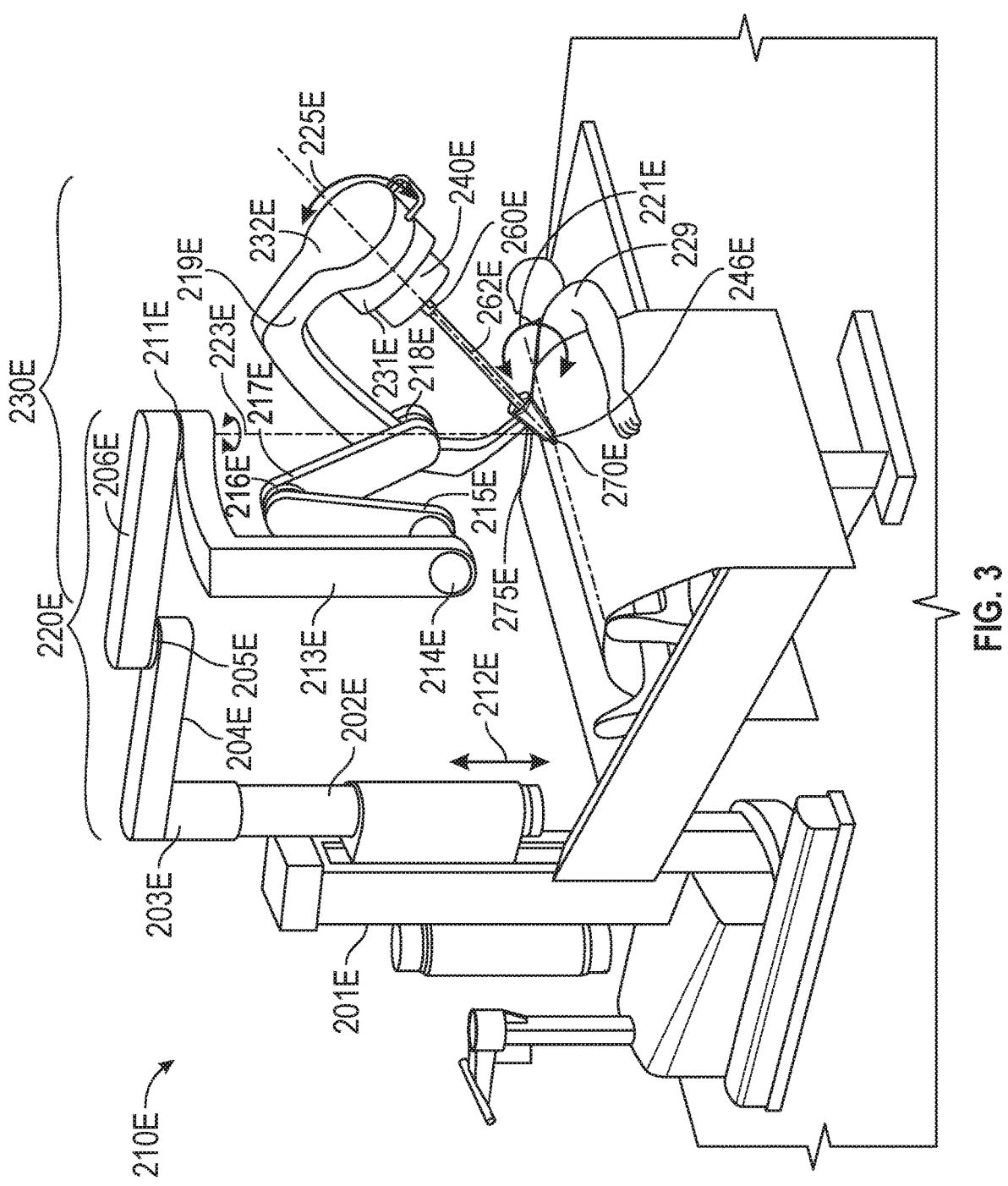
FIG. 3 is a perspective view of an example telesurgical system in accordance with various embodiments.

A manipulator system 210E is illustrated in FIG. 3. In the depicted example, the manipulator system 210E is implemented as a patient-side cart, and the surgery is in the abdomen of patient 229. However, the surgical system including manipulator system 210E can be used for a wide variety of surgeries by using various combinations of instruments.

Manipulator system 210E includes a floor-mounted base 201E as shown, or alternately a ceiling-mounted or other mechanically grounded base (not shown). Base 201E may be movable or fixed (e.g., to the floor, ceiling, wall, or other equipment such as an operating table). Base 201E supports the remainder of the manipulator system, which includes a usually passive, uncontrolled manipulator support structure 220E and an actively controlled manipulator system 230E, herein also referred to as entry guide manipulator 230E.

In one example, the manipulator support structure 220E includes a first setup link 202E and two passive rotational setup joints 203E and 205E. Rotational setup joints 203E and 205E allow manual positioning of the coupled setup links 204E and 206E. Alternatively, some of these setup joints may be actively controlled, and more or fewer setup joints may be used in various configurations. Setup joints 203E and 205E and setup links 204E and 206E allow a person to place entry guide manipulator 230E at various positions and orientations in Cartesian x, y, z space. A passive prismatic setup joint (not shown) between link 202E of manipulator support structure 220E and base 201E may be used for large vertical adjustments 212E.

Entry guide manipulator 230E includes an entry guide manipulator assembly 231E that supports a plurality of surgical device assemblies, at least one surgical device assembly being coupled to entry guide manipulator assembly 231E during a surgery. Each surgical device assembly includes a teleoperated manipulator and either a surgical instrument or a camera instrument mounted on the manipulator. For example, in FIG. 3, one surgical device assembly includes, mounted to manipulator 240E, an instrument 260E with a shaft 262E that extends through one of typically multiple channels of entry guide 270E during a surgical procedure.

Entry guide manipulator assembly 231E includes an instrument manipulator positioning system (hereinafter simply "positioning system"). The positioning system moves instrument mount interfaces of one or more manipulators 240E in a plane so that, when one or more instruments 260E are coupled to entry guide manipulator assembly 231E using the respective instrument mount interfaces, the shafts of the instruments 260E are each aligned for insertion into one of the channels in entry guide 270E. While the entry guide 270E is depicted as located at a body wall of the patient, it is to be understood that the manipulator system 210E can also be used, without need for modifications, with entry guides located at a distance from the body wall in an entry guide receptacle of an instrument access device as herein described.

The instrument mount interface(s) may be moved into position after attachment of the instrument(s). The plane in which the instrument mount interfaces are moved is generally perpendicular to the lengthwise axis of entry guide 270E, and the trajectories that instrument mount interfaces take in that plane may include straight and/or curved portions in various combinations. As a positioning element of a lateral motion mechanism of the positioning system moves along a trajectory, the instrument mount interface, and effectively a distal tip of a shaft of an instrument coupled to the instrument mount interface, moves along the same trajectory. Thus, motion of the positioning element causes the shaft to be moved to a location where the shaft is aligned with a channel in entry guide 270E. In this position, the shaft can enter and pass through the channel in entry guide 270E without damaging the instrument and without inhibiting operation of the instrument. The particular paths implemented in the positioning system depend at least in part on the types of surgical device assemblies that can be mounted on the entry guide manipulator assembly 231E and/or the configuration of channels in entry guide 270E.

Different entry guides may be used in different surgical procedures. An entry guide that enters the body between the ribs may optionally have a different shape than an entry guide that enters the body through an incision in the abdomen. Further, entry guides that enter the body generally differ, e.g., in length, from entry guides used outside the body, such as entry guides inserted through an entry guide receptacle at a proximal end of an envelope of an instrument access device as disclosed herein; entry guides used outside of and at a distance from the body may be shortened relative to those entering the body. The different shapes of the entry guides require different layouts of the channels that extend through the entry guides, i.e., different channel configurations. Also, the shapes and/or sizes of the shafts of the instruments may be different for different instruments. An entry guide is used that accommodates the shapes and sizes of the shafts of the instruments used in a particular surgical procedure. The trajectories are designed to accommodate a set of entry guides that can be used with manipulator system 210E.

The ability to individually position an instrument, and hence its shaft, with respect to a channel in an entry guide by moving an instrument mount interface provides versatility to manipulator system 210E. For example, this ability allows entry guides with different channel configurations to be used in system 210E. In addition, the positioning system eliminates the need for surgical-procedure-specific instruments. In other words, the instrument manipulator positioning system allows use of a common set of instruments with a variety of entry guides by moving the instrument shafts around, as described above.

Entry guide manipulator 230E includes a kinematic chain of active joints and links that are movable by motors or other actuators and receive movement control signals that are associated with master arm movements at the user control system. Using this kinematic chain, the entry guide manipulator 230E can adjust the position and orientation of the positioning system of entry guide manipulator assembly 231E and, by extension, the instrument. Usually, the entry guide manipulator 230E is configured and operated to constrain rotation of an instrument at a point located on the instrument's shaft, herein referred to as a remote center of motion.

Conventionally, the remote center of motion coincides generally with the position at which an instrument enters the patient (e.g., at the umbilicus for abdominal surgery). In accordance with this disclosure, however, where an instrument access device with an instrument entry guide located outside the body (in a port at the proximal end of the envelope of the instrument access device) is used, the position of the remote center of motion likewise falls outside the body. e.g., slightly above the body wall, and generally along the axis of the entry guide. A remote center of motion above the body wall allows for instruments to be moved radially outward from the entry guide's extended axis proximally of the patient's body wall and so get better triangulation access at or in the incision. Flexible instrument shafts in conjunction with a flexible wound retractor render such flexibility in operating the instruments possible without risking trauma to tissue.

The remote center of motion is the location at which yaw, pitch, and roll axes intersect, i.e., the location at which the kinematic chain of entry guide manipulator 230E remains effectively stationary while joints move through their range of motion. As shown in FIG. 3, a manipulator assembly yaw joint 211E is coupled between an end of setup link 206E and a first end, e.g., a proximal end, of a first manipulator link 213E. Yaw joint 211E allows first manipulator link 213E to move with reference to link 206E in a motion that may be arbitrarily defined as "yaw" around a manipulator assembly yaw axis 223E. As shown, yaw axis 223E of joint 211E is aligned with a remote center of motion located at or near the entry guide 270E.

A distal end of first manipulator link 213E is coupled to a proximal end of a second manipulator link 215E by a first actively controlled rotational joint 214E. A distal end of second manipulator link 215E is coupled to a proximal end of a third manipulator link 217E by a second actively controlled rotational joint 216E. A distal end of third manipulator link 217E is coupled to a fourth manipulator link 219E by a third actively controlled rotational joint 218E; the fourth manipulator link 219E extends in both directions away from the rotational joint 218E and, thus, has two distal ends relative to the location of the joint 218E.

In one embodiment, links 215E, 217E, and 219E are coupled together to act as a coupled motion mechanism. Coupled motion mechanisms are well known (e.g., such mechanisms are known as parallel motion linkages when input and output link motions are kept parallel to each other). For example, if rotational joint 214E is actively rotated, then joints 216E and 218E are also actively rotated so that link 219E moves with a constant relationship to link 215E. Therefore, it can be seen that the rotational axes of joints 214E, 216E, and 218E are parallel. When these axes are perpendicular to yaw axis 223E of joint 211E, links 215E, 217E, and 219E move with reference to link 213E in a motion that may be arbitrarily defined as "pitch" around a manipulator assembly pitch axis. The manipulator pitch axis extends into and out of the page in FIG. 3 at remote center of motion at or near the entry guide 270E. The motion around the manipulator assembly pitch axis is represented by arrow 221E. Since links 215E, 217E, and 219E move as a single assembly in this embodiment, first manipulator link 213E may be considered an active proximal manipulator link, and second through fourth manipulator links 215E, 217E, and 219E may be considered collectively an active distal manipulator link.

An entry guide manipulator assembly platform 232E is coupled to one of the distal ends of fourth manipulator link 219E. Entry guide manipulator assembly 231 is rotatably mounted on platform 232E. Entry guide manipulator assembly 231 can rotate a plurality of surgical device assemblies (e.g., 260E) as a group around axis 225E. Specifically, entry guide manipulator assembly 231 rotates as a single unit with reference to platform 232E in a motion that may be arbitrarily defined as "roll" around an entry guide manipulator assembly roll axis 225E.

In accordance with the present disclosure, all the instruments (including a camera instrument) enter the instrument access device via a single port, which is generally stationary relative to the remote center of motion imposed by entry guide manipulator 230E (and defined by the intersection of manipulator assembly yaw axis 223E, manipulator assembly pitch axis 221E, and manipulator roll axis 225E). The configuration of links 215E, 217E, and 219E, and the configuration of joints 214E, 216E, and 218E are such that remote center of motion is located distal of entry guide manipulator assembly, with sufficient distance to allow entry guide manipulator assembly to move freely with respect to the entry guide.

An entry guide receptacle 275E may be removably coupled (directly or indirectly via a mount) to the distal end of fourth manipulator link 219E opposite the distal end to which entry guide manipulator assembly platform 232E is coupled. In one implementation, the entry guide receptacle 275E or mount is coupled to link 219E by a rotational joint that allows it to move between a stowed position adjacent link 219E and an operational position that ensures that the remote center of motion is located along the entry guide receptacle 275E or the entry guide 270E received therein. During operation, the entry guide receptacle 275E is fixed in position relative to link 219E according to one aspect. Entry guide receptacles and entry guides may be made of various materials, e.g., steel or extruded plastic. Plastic, which is less expensive than steel, may be suitable for one-time use per surgical procedure.

The various passive setup joints/links and active joints/links allow positioning of the instruments and imaging system with a large range of motion when a patient 229 is placed in various positions on a movable table. Certain setup and active joints and links in the manipulator support structure 210E and/or entry guide manipulator 230E may be omitted to reduce the surgical system's size and shape, or joints and links may be added to increase degrees of freedom. It should be understood that the manipulator support structure 210E and entry guide manipulator 230E may include various combinations of links, passive joints, and active joints (redundant degrees of freedom may be provided) to achieve a necessary range of poses for surgery.

Instrument Access Devices with Countermotion Mechanisms

Figure 4A:
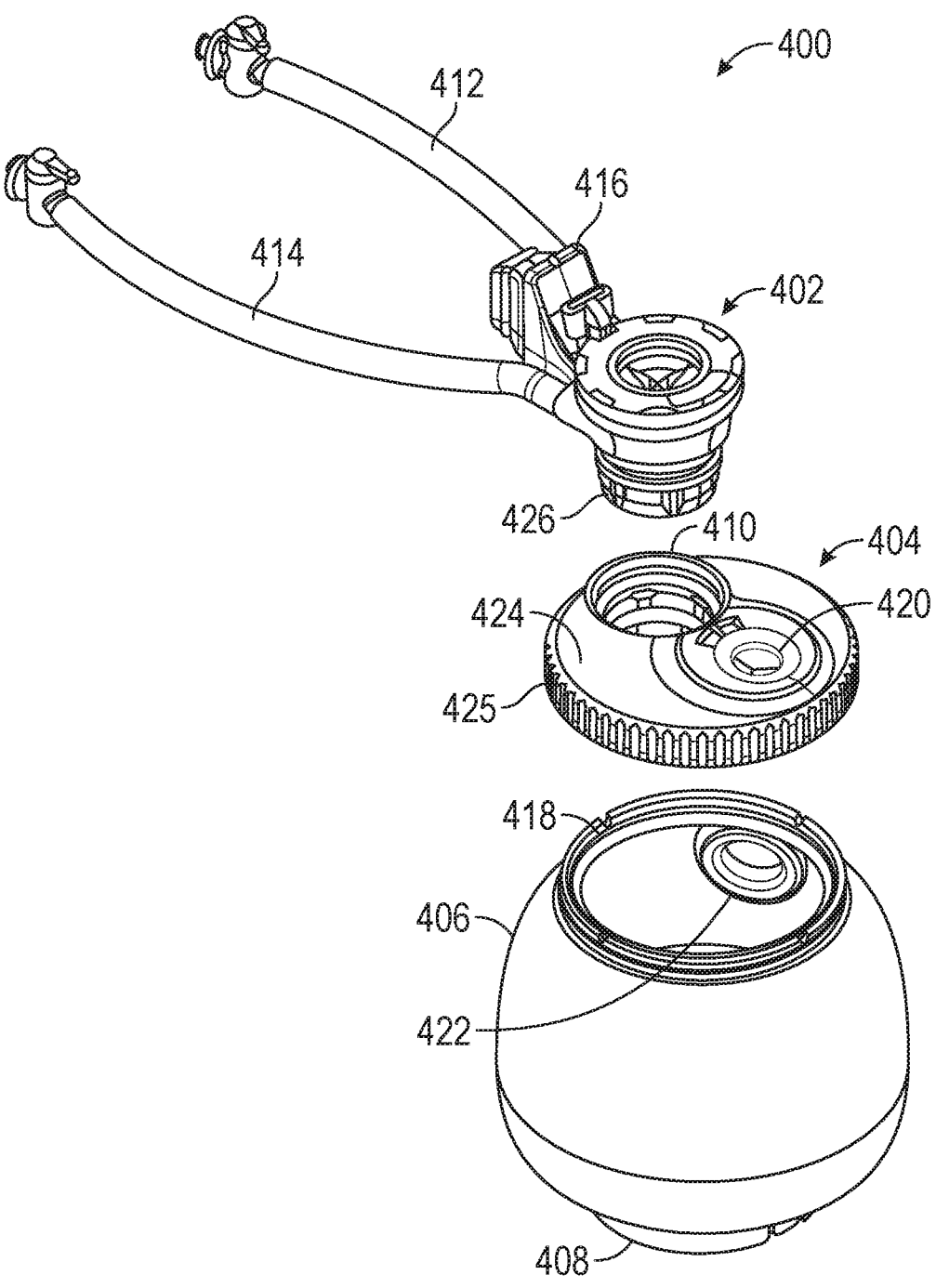
FIG. 4A is an exploded perspective view of an example instrument access device in accordance with various embodiments.

FIG. 4A is an exploded perspective view of an example instrument access device 400 in accordance with various embodiments. In FIG. 4A, instrument access device 400 includes entry guide receptacle assembly 402 (including entry guide receptacle 426), countermotion assembly 404, envelope 406, and clamp 408 (serving as distal coupling component). The entry guide receptacle 426 and countermotion assembly 404 together form the proximal coupling component in this embodiment.

Clamp 408 is received in a distal opening of envelope 406, and, in use, affixes instrument access device 400 to a wound retractor or similar port device at a body opening. Countermotion assembly 404 is received in a proximal opening 418 of envelope 406, and it includes a first port 410 that receives the entry guide receptacle 426 and is therefore also referred to as the "entry guide port" 410, and a second port 420 that can receive assist instruments and is therefore also referred to as the "assistant port" 420. One or more instruments enter instrument access device 400 at the proximal end through an entry guide received in entry guide receptacle 426 or through the assistant port 420. Envelope 406 also includes an additional envelope assistant port 422 through which further instruments can enter. The instruments (whether entering through the entry guide port 410 or either of the assistant ports 420, 422) either work within envelope 406 or leave it through the distal opening to enter the patient's body. The assistant port 422 may optionally be configured to allow surgical equipment (e.g., suture or mesh material, imaging probes, instrument accessories, and the like) to be introduced or removed from the interior of envelope 406, or to allow tissue to be removed from the interior of envelope 406.

Entry guide receptacle assembly 402 includes entry guide receptacle 426 as well as a connector 416 that affixes instrument access device 400 to an arm of a teleoperated surgical system, such as the system depicted and described with reference to FIG. 3. Further, entry guide receptacle assembly 402 includes gas lines 412 and 414, which carry insufflation gas through the lines and into instrument access device 400, including into envelope 406. The insufflation lines 412, 414 may have standard flow Luer fittings or, alternatively, other fittings that permit a higher gas flow volume over time. The use of two gas lines 412, 414 serves to enable connecting an insufflation source to either side of the entry guide port 410, which can accommodate spatial constraints in surgical setting. Further, the two gas lines 412, 414 allow one line to be used for insufflation and the other line to be used for smoke evacuation, e.g., by venting the second line to the room or using an insufflator with built-in smoke evacuator.

Countermotion assembly 404 includes an orbital element 424 (as an example of element 10c) in which the openings of the entry guide port 410 and the assistant port 420 are defined, an outer element 425 (as an example of element 10b) received in the proximal opening of the envelope 406, and a countermotion mechanism that rotates assistant port 420 around entry guide port 410 (and, thus, entry guide receptacle 426) without envelope 406 twisting about a central axis of the envelope 406. In use, when the instrument access device is affixed to a telesurgical system, entry guide receptacle 426 remains stationary in space as assistant port 420 rotates around it. (In this embodiment, entry guide receptacle 426 serves the function of the stationary component 10a.)

Figure 4B:
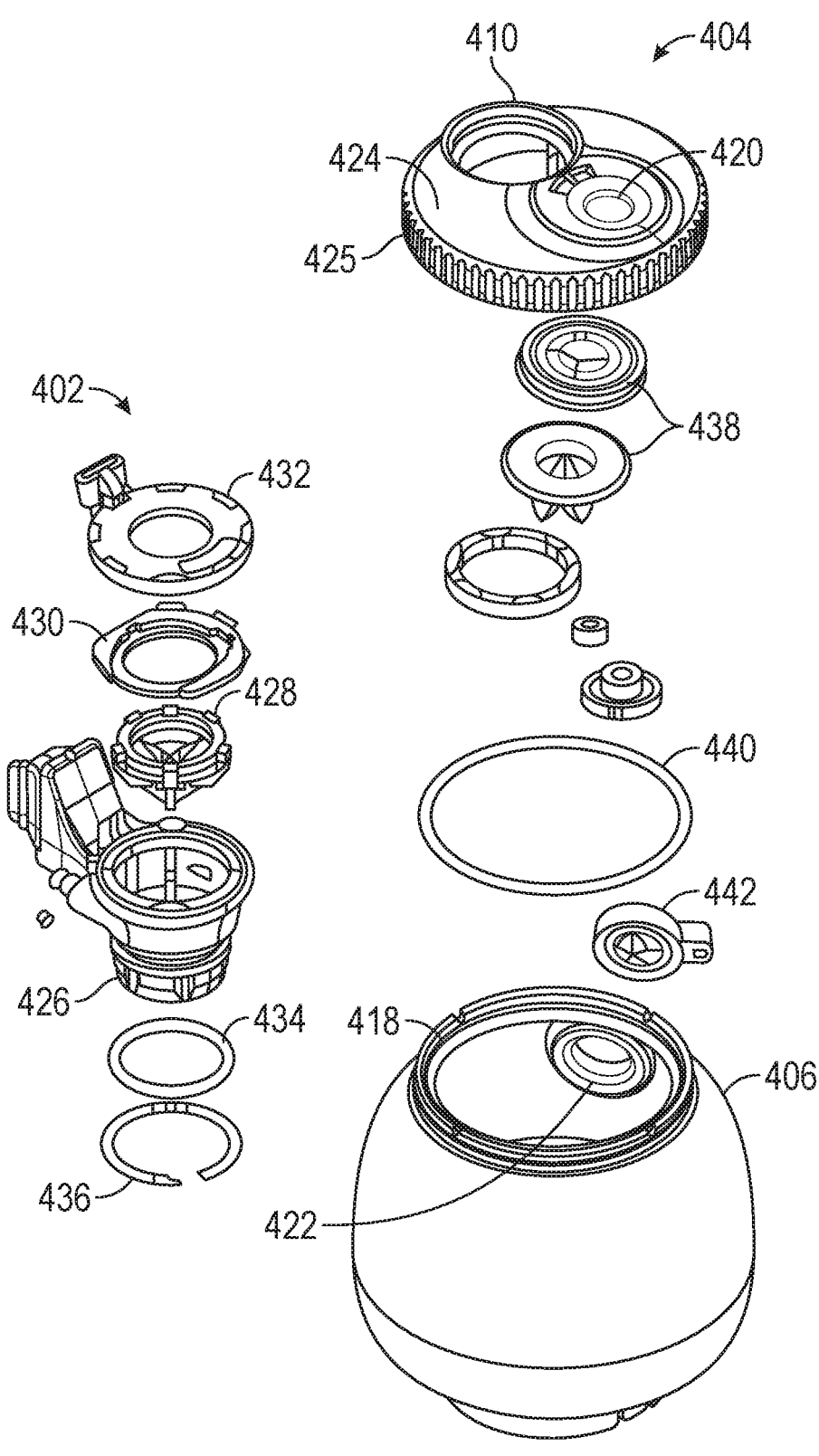
FIG. 4B is an exploded perspective view depicting additional details of the instrument access device of FIG. 4A.

FIG. 4B is an exploded perspective view depicting additional details of instrument access device 400. In FIG. 4B, entry guide receptacle assembly 402 includes entry guide receptacle 426, instrument guide seal 428, seal support 430, cover 432, entry guide receptacle O-ring 434, and entry guide receptacle retaining ring 436. Instrument guide seal 428 is received in entry guide receptacle 426. Cover 432 locks onto entry guide receptacle 426, capturing (or "sandwiching") seal support 430 and instrument guide seal 428 between the cover 432 and entry guide receptacle 426. Entry guide receptacle O-ring 434 is received in entry guide port 410 and seals the outer surface of the lumen of entry guide receptacle 426 in port 410. Entry guide receptacle retaining ring 436 couples entry guide receptacle 426 into entry guide port 410 and thereby connects entry guide receptacle assembly 402 to countermotion assembly 404.

In some examples, entry guide receptacle assembly 402 is configured to receive an instrument entry guide, which is configured to receive and seal multiple instruments through a single port. In such cases, instrument guide seal 428 is configured to receive and seal the instrument entry guide. In an example, instrument guide seal 428 can include a cross-slit seal, duckbill seal, wiper seal, septum seal, or another type of seal appropriate for receiving and sealing an instrument entry guide in accordance with this disclosure. In an example, instrument guide seal 428 includes a seal similar to that disclosed in International Application No. PCT/US2019/031393 (filed May 8, 2009) (disclosing an "INSTRUMENT SEAL"), the entire contents of which are incorporated herein by reference.

In FIG. 4B, countermotion assembly 404 includes orbital element 424, which includes entry guide port 410 and assistant port 420. In addition, countermotion assembly 404 includes assistant port seal 438 and envelope O-ring 440. Assistant port seal 438 is received in and is coupled to assistant port 420. Assistant port seal 438 is configured to receive and seal a manually operated instrument and can include a variety of types of seals, including a cross-slit, duckbill, wiper, or septum seal. In an example, assistant port seal 438 includes a seal similar to that disclosed in International Application No. PCT/US2019/031393. Envelope O-ring 440 is received in proximal opening 418 of envelope 406 and is configured to seal outer element 425 of countermotion assembly 404 in opening 418. Together with O-ring 434, O-ring 440 is important for holding insufflation while allowing the assistant port 420 to rotate about the entry guide port 410. The instrument access device 402 also includes an envelope assistant port seal 442, which is received in envelope assistant port 422 of envelope 406. Envelope assistant port seal 442 is configured to receive and seal a manually operated instrument and can include a variety of types of seals, including a cross-slit, duckbill, wiper, or septum seal. In an example, envelope assistant port seal 442 includes a seal similar to that disclosed in International Application No. PCT/US2019/031393.

Figure 4C:
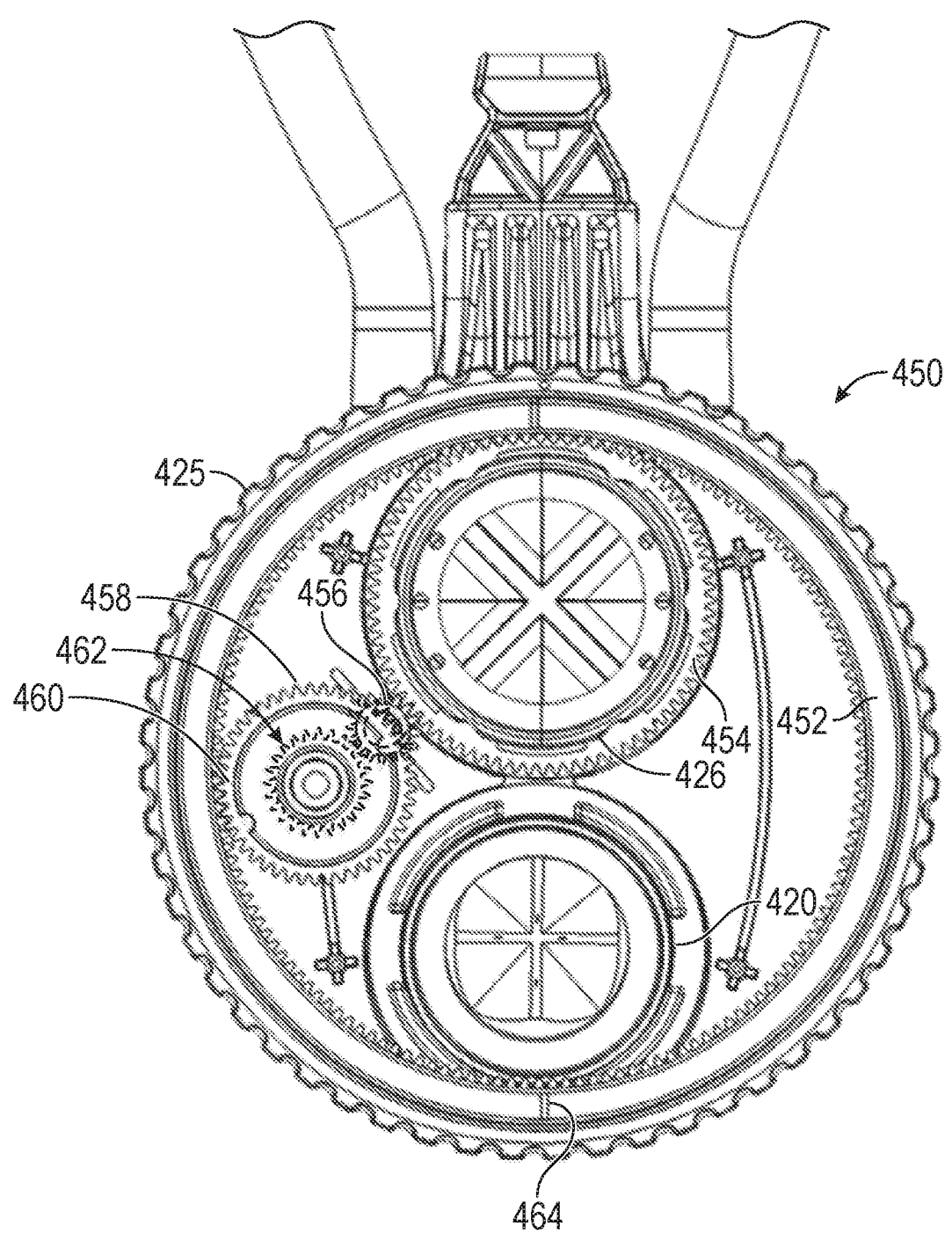
FIG. 4C is a bottom plan view depicting a gear train, in accordance with one embodiment, for rotating one port within an instrument access device as depicted in FIG. 4A around another port without twisting an envelope of the device.

FIG. 4C is a bottom plan view depicting gear train 450 in accordance with one embodiment. Gear train 450 is a mechanism by which assistant port 420 is able to rotate around entry guide receptacle 426 and entry guide port 410 without envelope 406 rotating about a central axis of the envelope, or, in other words, without envelope 406 twisting. Gear train 450 includes first gear 452, second gear 454, idler gear 456, and intermediate gear 458. In FIG. 4C, first gear 452 and second gear 454 are ring gears, with the gear teeth of first gear 452 facing radially inward and the gear teeth of second gear 454 facing radially outward. Intermediate gear 458 is a step spur gear including third spur gear 460 and fourth spur gear 462 (hidden behind third spur gear 460) engaged with idler gear 456 (partially hidden behind third spur gear 460). Third and fourth spur gears 460, 462 are coaxially coupled and rotate together.

First gear 452 is positioned around the outer periphery of orbital element 424 of countermotion assembly 404, and it is configured to be affixed to outer element 425, which is coupled to proximal opening 418 of envelope 406. Second gear 454 is coupled to the outer periphery of entry guide receptacle 426. Note that the first and second gears 452, 454 are located in different planes, second gear 454 being above (that is, in the bottom-up view, below) first gear 452, and they do not directly operatively engage each other. The first and second gears 452, 454 are coupled via idler gear 456 and intermediate gear 458 (all collectively forming countermotion mechanism 10d). More specifically, idler gear 456 operatively engages second gear 454 and fourth gear 462 of intermediate gear 458. Fourth gear 462 is coupled to third gear 460 of intermediate gear 458, which, in turn, operatively engages first gear 452. Idler gear 456 reverses the direction of rotation between first gear 452 and second gear 454. In particular, from the perspective of the view of FIG. 4C, idler gear 456 rotates counter-clockwise when intermediate gear 458 (including third and fourth gears 460 and 462) rotates clockwise.

Figure 4D:
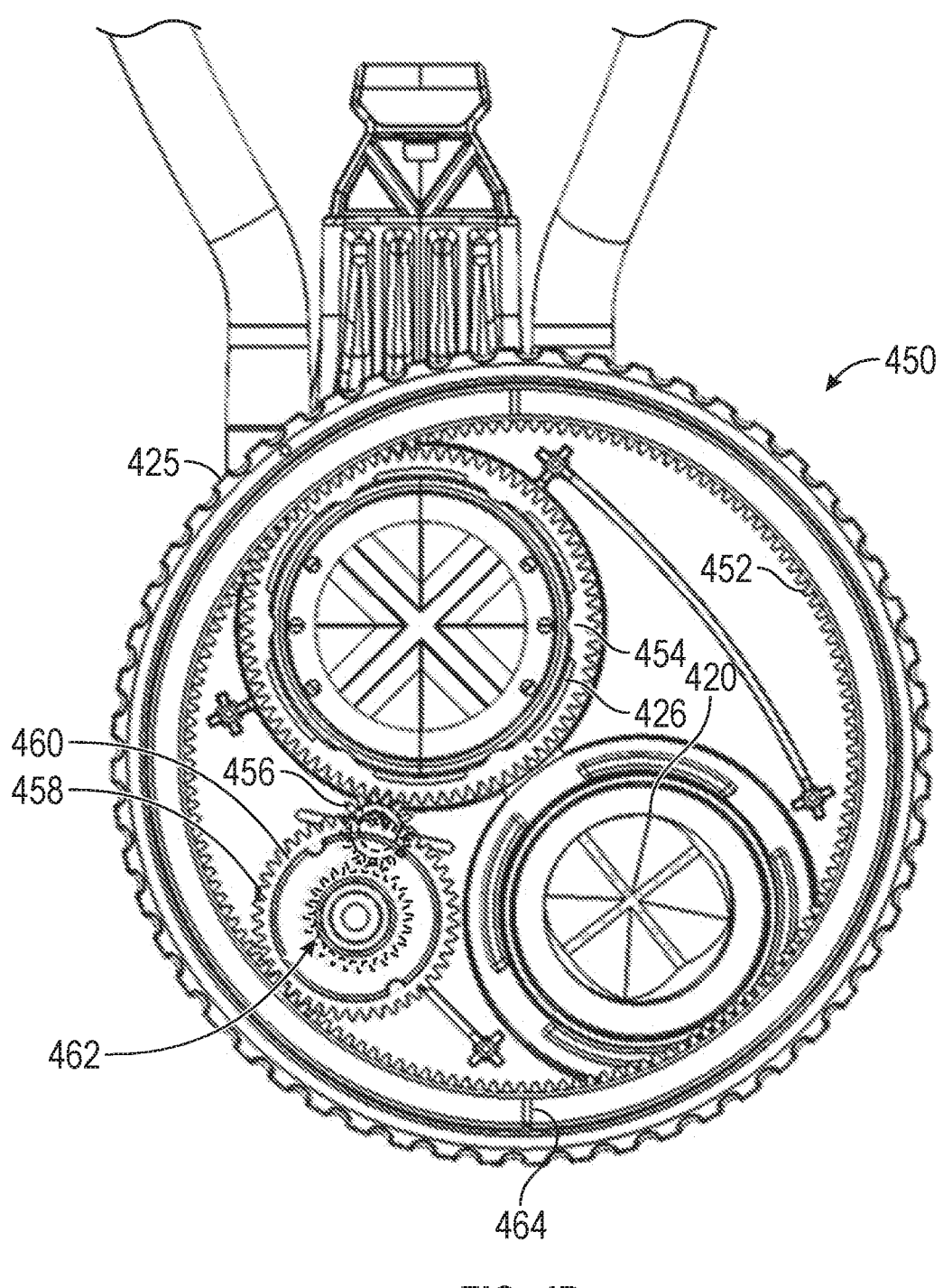
FIGS. 4D and 4E are bottom plan views depicting the gear train of FIG. 4C in different rotational positions.
Figure 4E:
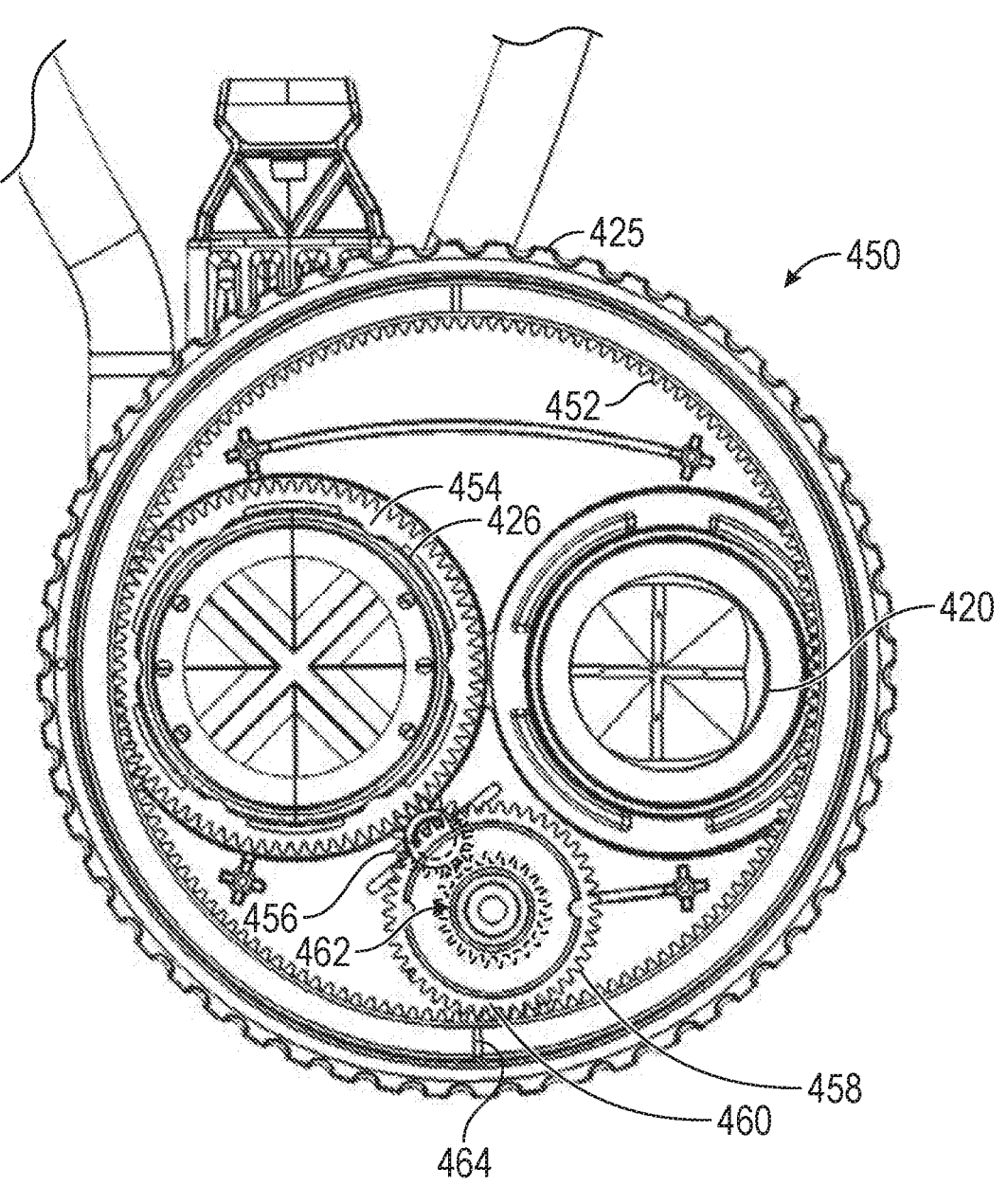

In the example of FIG. 4C, gear train 450 is depicted in a first position. To illustrate motion of the gear train 450, and by association assistant port 420, gear train 450 is depicted in two additional positions in FIGS. 4D and 4E. Referring to FIGS. 4C-4E, note first that second gear 454 and, by association, entry guide receptacle 426 stay fixed in space and do not either translate or rotate relative to the telesurgical system. (Entry guide port 410 is likewise translationally fixed in space but rotates along with the orbital element relative to the entry guide receptacle.) Idler gear 456 is operatively engaged with and rotates around second gear 454. As idler gear 456 turns as it translates around second gear 454, idler gear 456 turns fourth spur gear 462 of intermediate gear 458, which, in turn causes third spur gear 460 of intermediate gear 458 to turn. As third spur gear 460 turns, it rotates first gear 452 and causes first gear 452 to translate around a central axis of entry guide port 410 without rotating about the central axis of first gear 452. This is the manner in which assistant port 420 is able rotate around entry guide port 410 and entry guide receptacle 426 without causing envelope 406 (which is coupled to first gear 452) to twist. Note that, along with first gear 452 and the outer element 425 of the countermotion mechanism, the proximal opening of the envelope 406 translates as well and thereby changes its position relative to the distal opening of the envelope 406. This relative motion between the proximal and distal openings is accommodated by the flexible or movable nature of the envelope 406.

This swinging translation of first gear 452 (and by association envelope 406) about entry guide port 410 is enabled, at least in part, by the gear ratios of the various gears of gear train 450; the gear ratios are chosen such that the rotations remain synchronized in that a rotation of the first gear 452 relative to the idler gear 456 by a certain angle in one direction is accompanied by a rotation of the second gear 454 relative to the idler gear 452 by the same angle in the opposite direction. In particular, a gear ratio of the third spur gear 460 to the fourth spur gear 462 is equal to a gear ratio of first gear 452 to second gear 454. The motion of first gear 452 can be tracked in FIGS. 4A-4E by reference to index mark 464 on the outer element 425 and gear 452. Note that while index mark 464 translates relative to entry guide receptacle 426 and entry guide port 410, the mark 464 and therefore first gear 452 do not rotate. Or in other words, the first gear stays in a fixed rotational orientation relative to entry guide receptacle 426 and entry guide port 410.

Figure 5A:
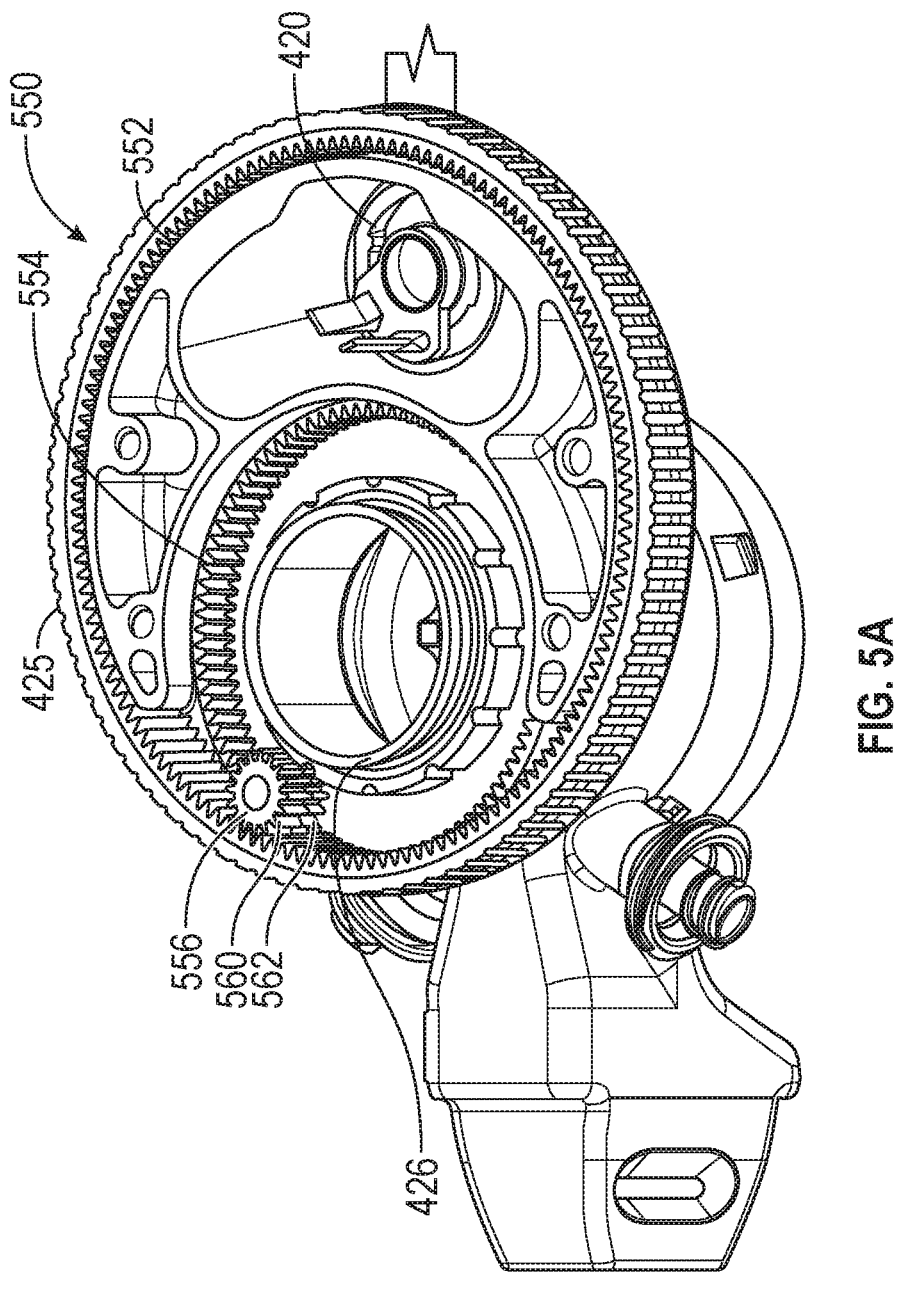
FIG. 5A is a bottom perspective view depicting a gear train, in accordance with another embodiment, for rotating one port within an instrument access device as depicted in FIG. 4A around another port without twisting an envelope of the device.

FIG. 5A is a bottom perspective view depicting gear train 550 in accordance with another embodiment. Gear train 550 is another mechanism by which assistant port 420 is able to rotate around entry guide receptacle 426 and entry guide port 410 without envelope 406 rotating about a central axis of the envelope, or in other words without envelope 406 twisting. Gear train 550 includes first gear 552, second gear 554, and intermediate gear 556. In FIG. 5A, first gear 552 and second gear 554 are ring gears with the gear teeth of first gear 552 and second gear 554 facing radially inward. Additionally, intermediate gear 556 is a step spur gear including third spur gear 560 and fourth spur gear 562, so that gears 560 and 562 are coaxially coupled and rotate together.

First gear 552 is positioned around the outer periphery of orbital element 424 of countermotion assembly 404 and is configured, along with outer element 425, to be positioned in and coupled to proximal opening 418 of envelope 406 (see FIGS. 4A and 4B). Second gear 554 is positioned around the outer periphery of entry guide receptacle 426. Intermediate gear 556 is positioned between first gear 552 and second gear 554. Third spur gear 560 of intermediate gear 556 operatively engages first gear 552. Fourth spur gear 562 of intermediate gear 556 operatively engages second gear 554.

Figure 5B:
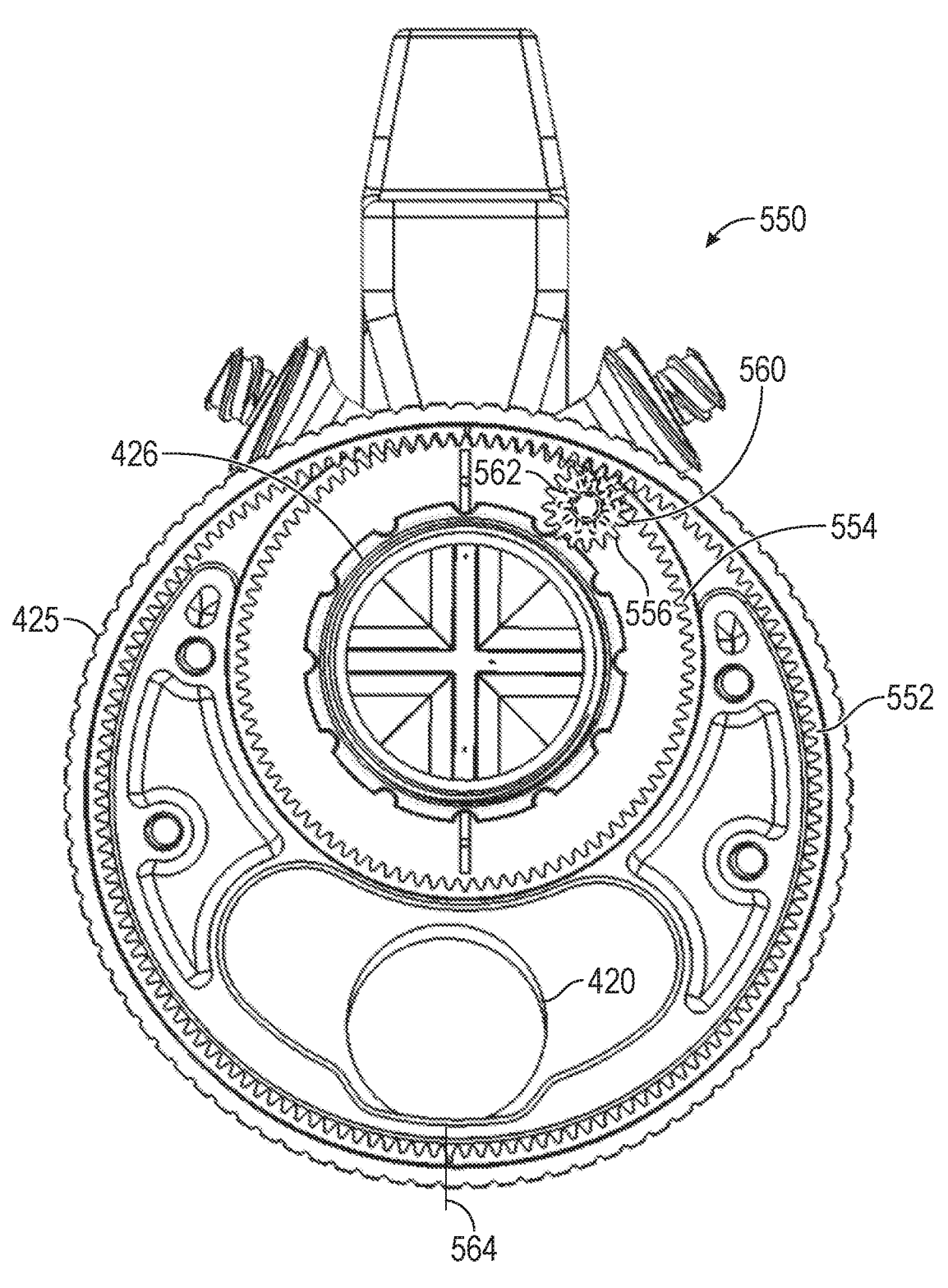
FIG. 5B-5D are bottom plan views depicting the gear train of FIG. 5A in different rotational positions.
Figure 5C:
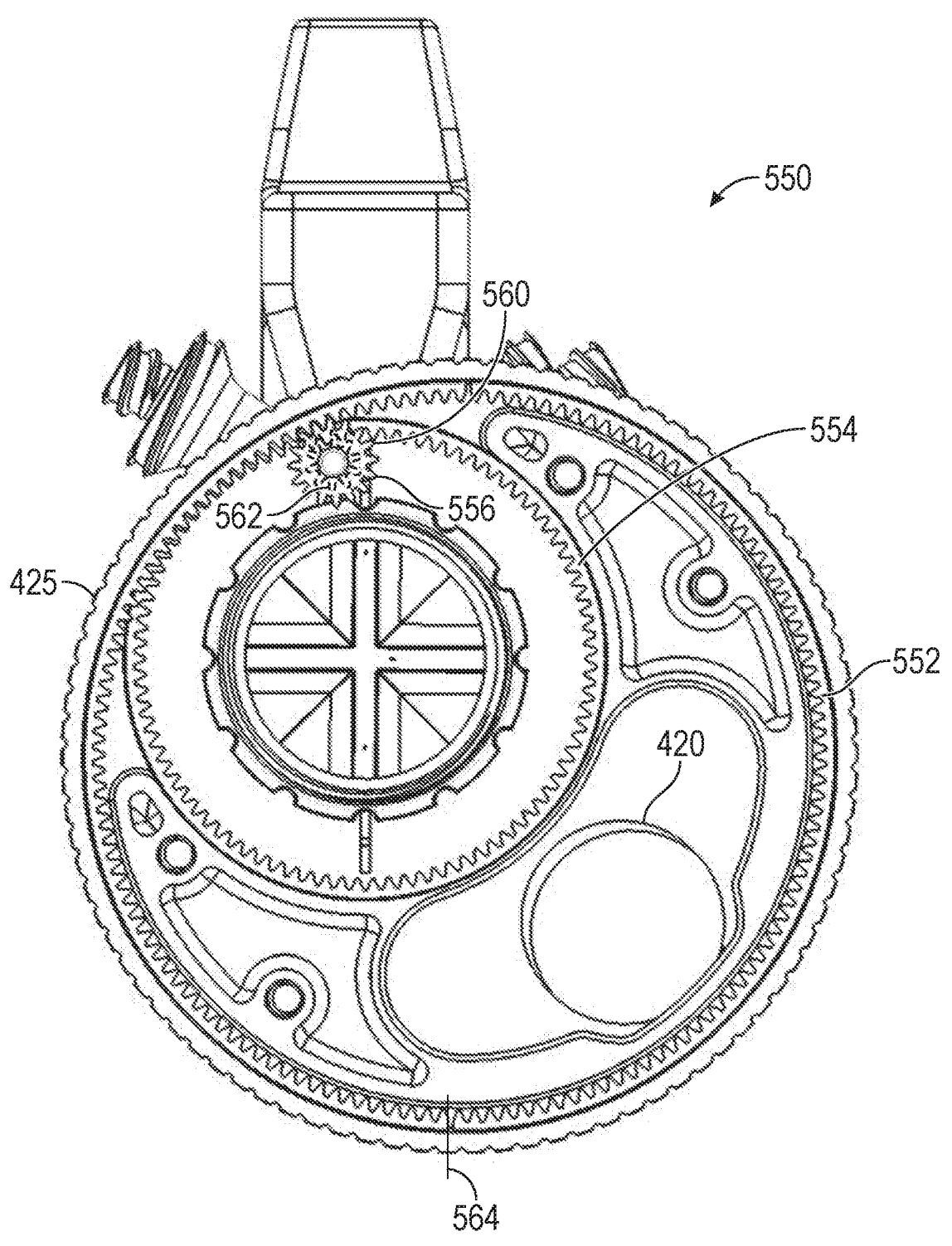
Figure 5D:
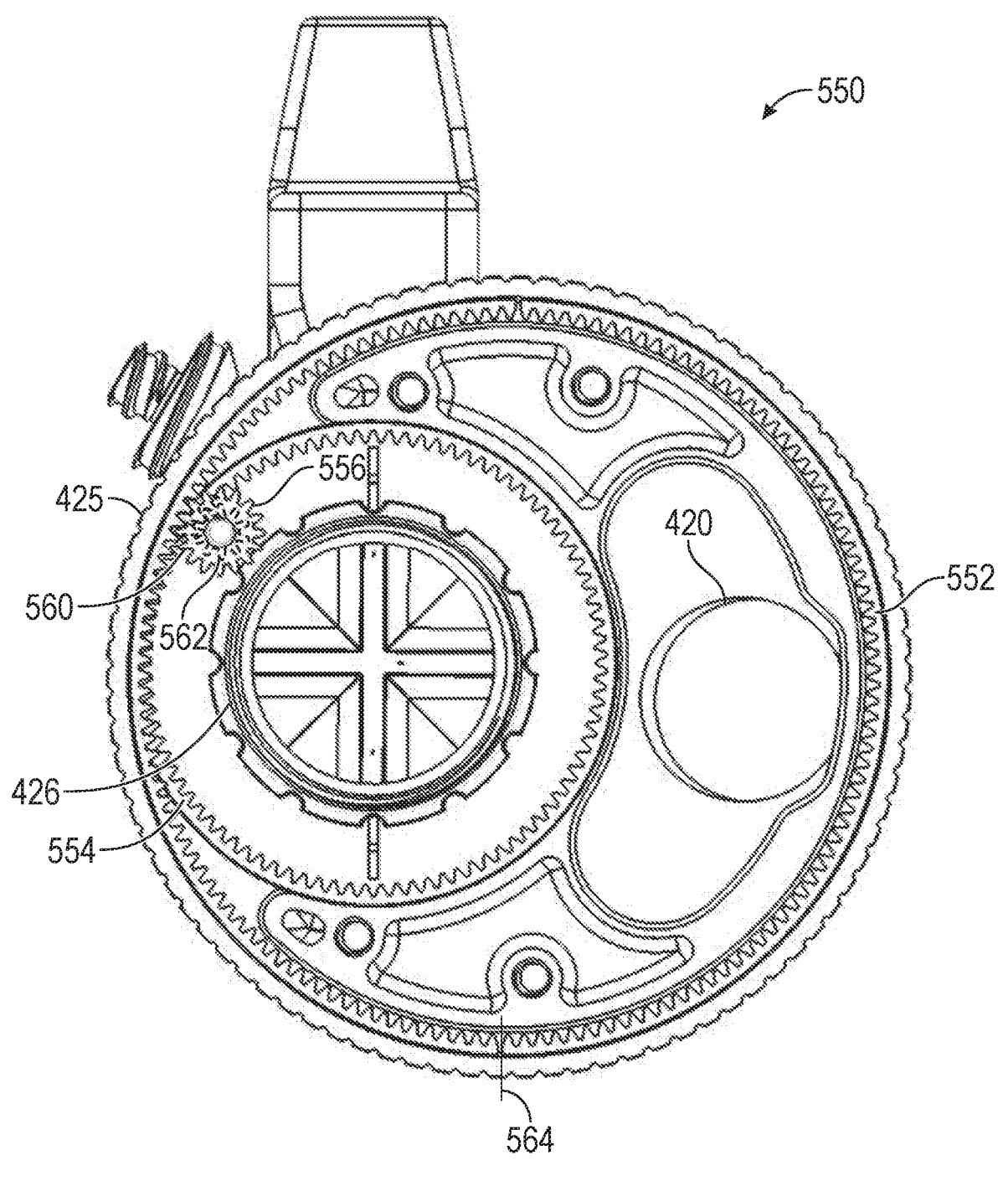

FIG. 5B is a bottom plan view depicting gear train 550. In the example of FIG. 5B, gear train 550 is depicted in a first position. To illustrate motion of the gear train 550, and by association orbital element 424, which includes assistant port 420, gear train 550 is depicted in two additional positions in FIGS. 5C and 5D. Referring to FIGS. 5B-5D, note first that second gear 554, and by association entry guide receptacle 426, stay fixed in space and do not either translate or rotate relative to other components. Fourth spur gear 562 of intermediate gear 556 rotates around and is operatively engaged to second gear 554. As fourth spur gear 562 rotates around second gear 554, third spur gear 560 of intermediate gear 556 engages and turns first gear 552, which causes first gear 452 to translate around a central axis of entry guide port 410 without rotating relative to the central axis of first gear 552. This is the manner in which assistant port 420 is able to rotate around entry guide port 410 and entry guide receptacle 426 without causing envelope 406 (which is coupled to first gear 552) to twist.

This swinging translation of first gear 552 (and by association envelope 406) about entry guide port 410 is enabled, at least in part, by the gear ratios of the various gears of gear train 550. In particular, a gear ratio of the third spur gear 560 to the fourth spur gear 562 is equal to a gear ratio of first gear 552 to second gear 554. The motion of first gear 552 can be tracked in FIGS. 5B-5D by reference to index mark 564 on the outer element 425 and gear 552. Note that while index mark 564 translates relative to entry guide receptacle 426 and entry guide port 410, the mark 564, and therefore first gear 552 do not rotate. In other words, the first gear stays in a fixed rotational orientation relative to entry guide receptacle 426 and entry guide port 410.

Figure 6A:
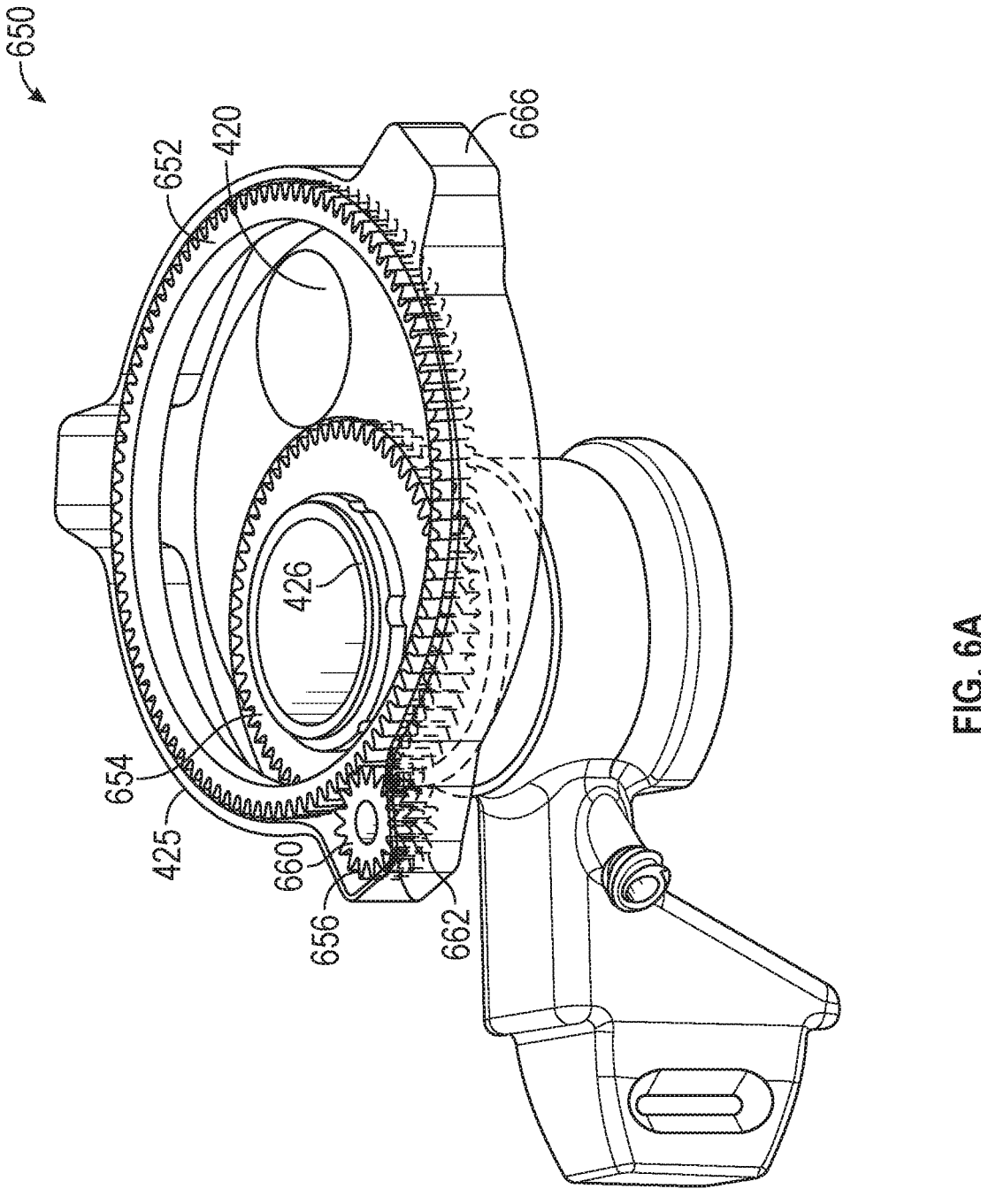
FIG. 6A is a bottom perspective view depicting a gear train, in accordance with yet another embodiment, for rotating one port within an instrument access device as depicted in FIG. 4A around another port without twisting an envelope of the device.

FIG. 6A is a bottom perspective view depicting gear train 650 in accordance with yet another embodiment. Gear train 650 is another mechanism by which assistant port 420 is able to rotate around entry guide receptacle 426 and entry guide port 410 without envelope 406 rotating about a central axis of the envelope, or in other words without envelope 406 twisting. Gear train 650 includes first gear 652, second gear 654, and intermediate gear 656, and it operates in a manner similar to gear train 550 with the differences that, as shown in FIG. 6A, first gear 652 and second gear 654 are ring gears with the gear teeth of first gear 652 and second gear 654 facing radially outward, and intermediate gear 656 is a step spur gear including third spur gear 660 and fourth spur gear 662 located outside the first and second ring gears 652, 654.

First gear 652 is positioned around the outer periphery of orbital element 424 of countermotion assembly 404 and is configured, along with the outer element 425, to be positioned in and coupled to proximal opening 418 of envelope 406 (see FIGS. 4A and 4B). Second gear 654 is positioned around the outer periphery of entry guide receptacle 426. Intermediate gear 656 is positioned between first gear 652 and second gear 654. In this example, the outer element 425 includes three outward-protruding optional tabs 666, and intermediate gear 656, which includes third and fourth spur gears 660, 662, is arranged within one of the three tabs 666. Tabs 666 can serve multiple functions, including housing intermediate gear 656 and providing finger grips to manipulate countermotion assembly 404 to rotate assistant port 420. Third spur gear 660 of intermediate gear 656 operatively engages first gear 652. Fourth spur gear 662 of intermediate gear 656 operatively engages second gear 654.

Figure 6B:
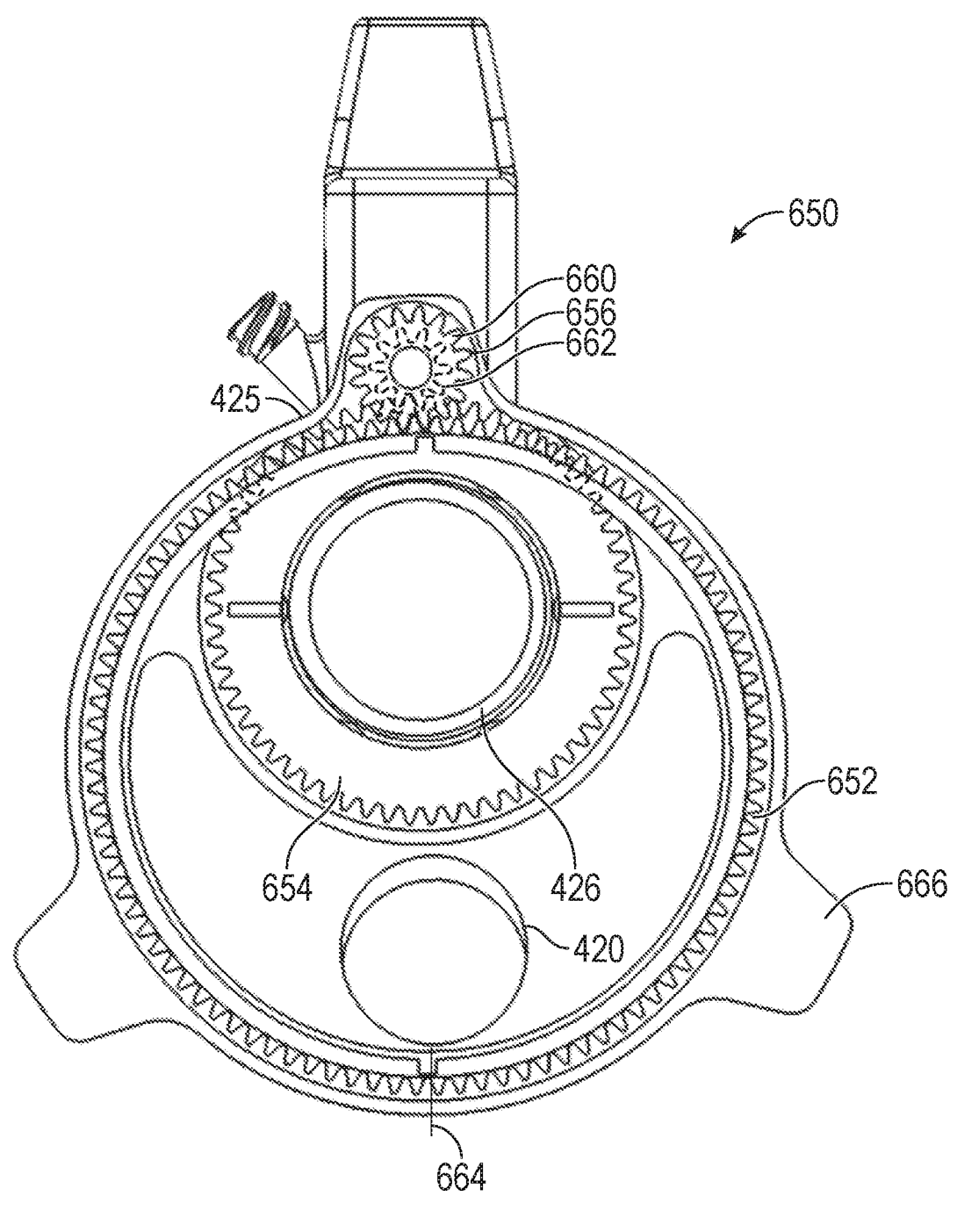
FIG. 6B-6D are bottom plan views depicting the gear train of FIG. 6A in different rotational positions.
Figure 6C:
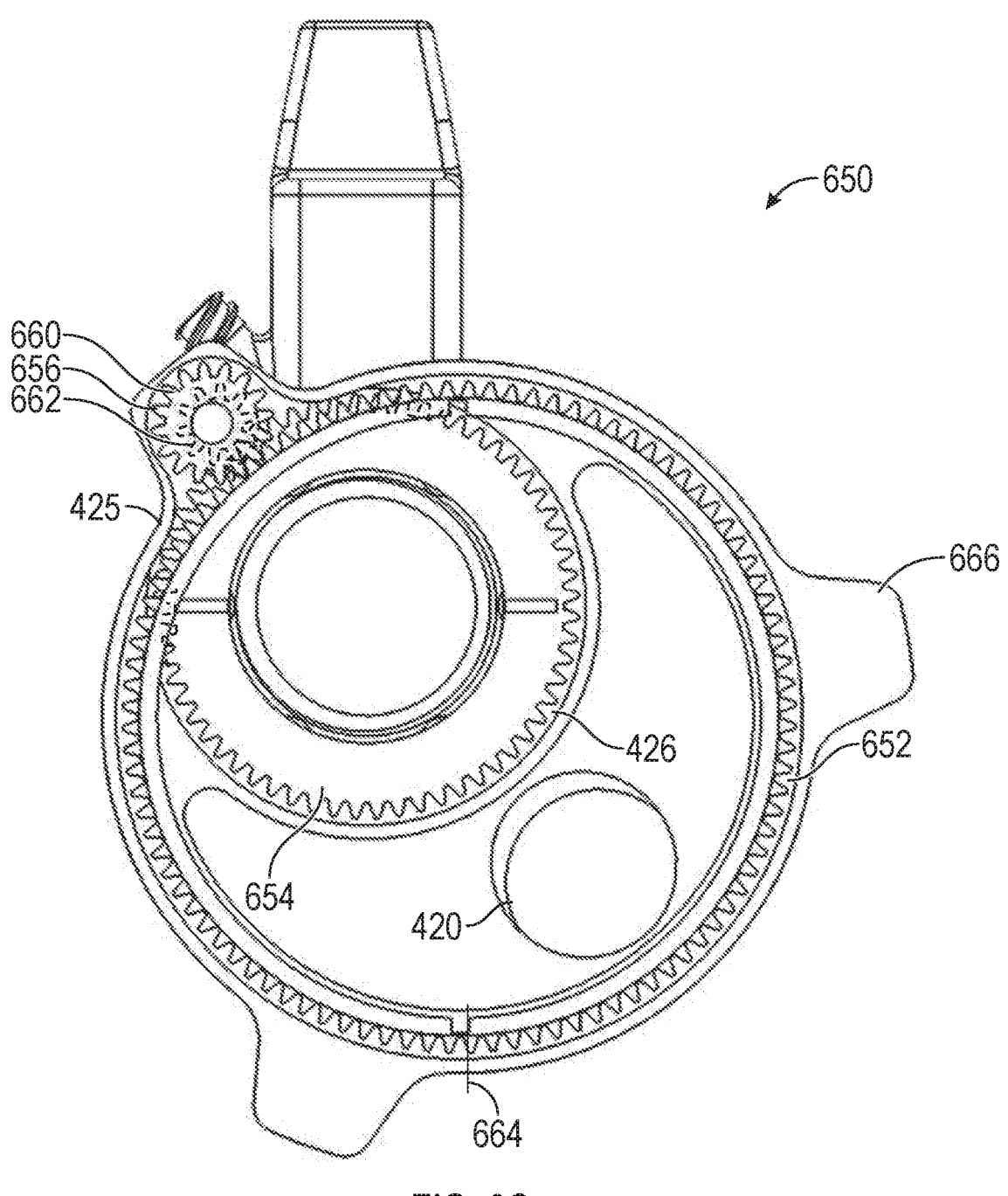
Figure 6D:
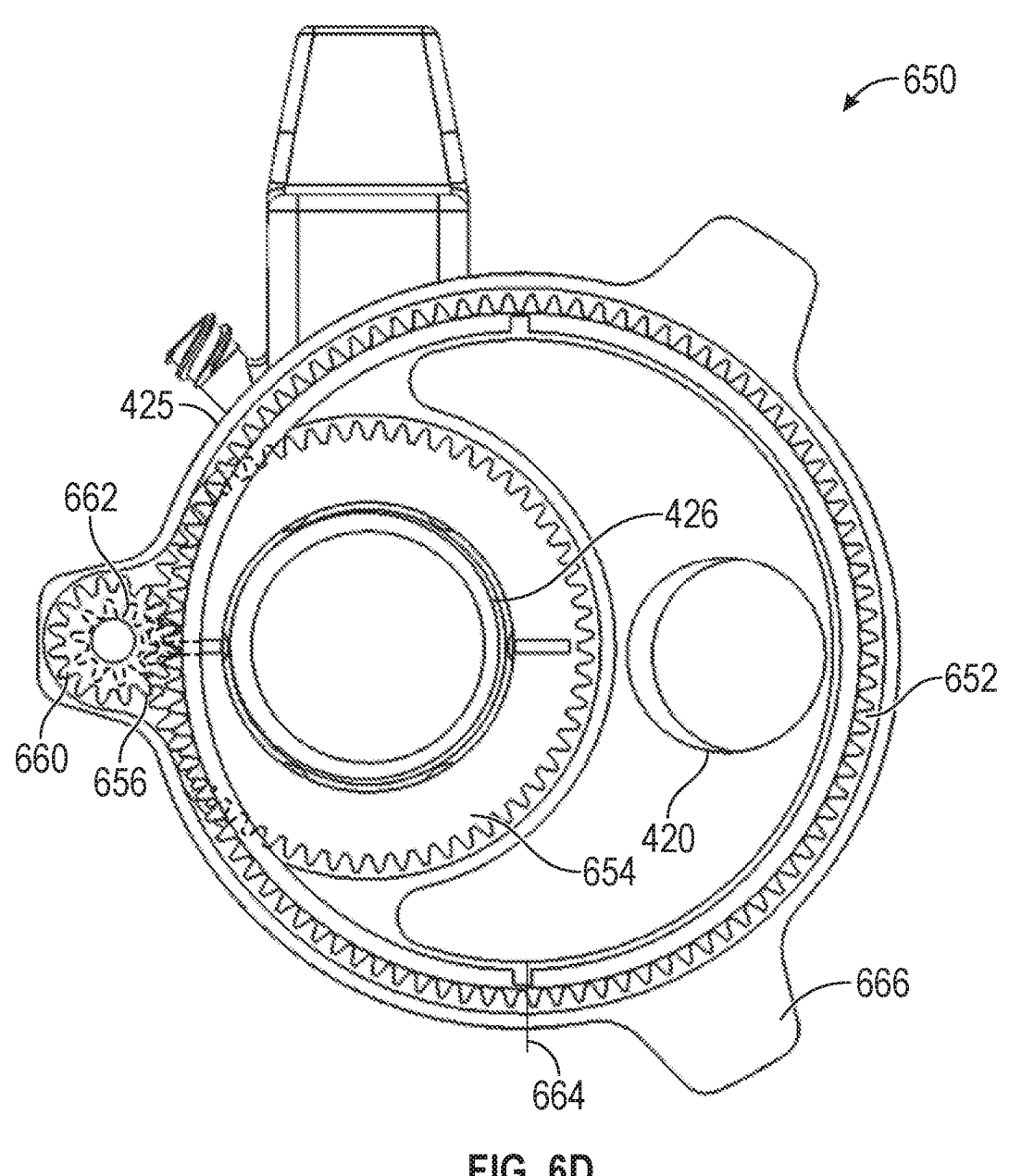

FIG. 6B is a bottom plan view depicting gear train 650 in accordance with this disclosure. In the example of FIG. 6B, gear train 650 is depicted in a first position. To illustrate motion of the gear train 650, and by association orbital element 424 and assistant port 420, gear train 650 is depicted in two additional positions in FIGS. 6C and 6D. Referring to FIGS. 6B-6D, note first that second gear 654 and by association entry guide receptacle 426 stay fixed in space and do not either translate or rotate relative to other components. Fourth spur gear 662 of intermediate gear 656 rotates around and is operatively engaged to second gear 654. As fourth spur gear 662 rotates around second gear 654, third spur gear 660 of intermediate gear 656 engages and turns first gear 652, which causes first gear 652 to translate around a central axis of entry guide port 410 without rotating about the central axis of first gear 652. This is the manner in which assistant port 420 is able rotate around entry guide port 410 and entry guide receptacle 426 without causing envelope 406 (which is coupled to first gear 652) to twist.

This swinging translation of first gear 652 (and by association envelope 406) about entry guide port 410 is enabled, at least in part, by the gear ratios of the various gears of gear train 650. In particular, a gear ratio of the third spur gear 660 to the fourth spur gear 662 is equal to a gear ratio of first gear 652 to second gear 654. The motion of first gear 652 can be tracked in FIGS. 6B-6D by reference to index mark 664 on the outer element 425 and gear 652. Note that while index mark 664 translates relative to entry guide receptacle 426 and entry guide port 410, the mark 664 and therefore first gear 652 do not rotate. In other words, the first gear stays in a fixed rotational orientation relative to entry guide receptacle 426 and entry guide port 410.

Figure 7A:
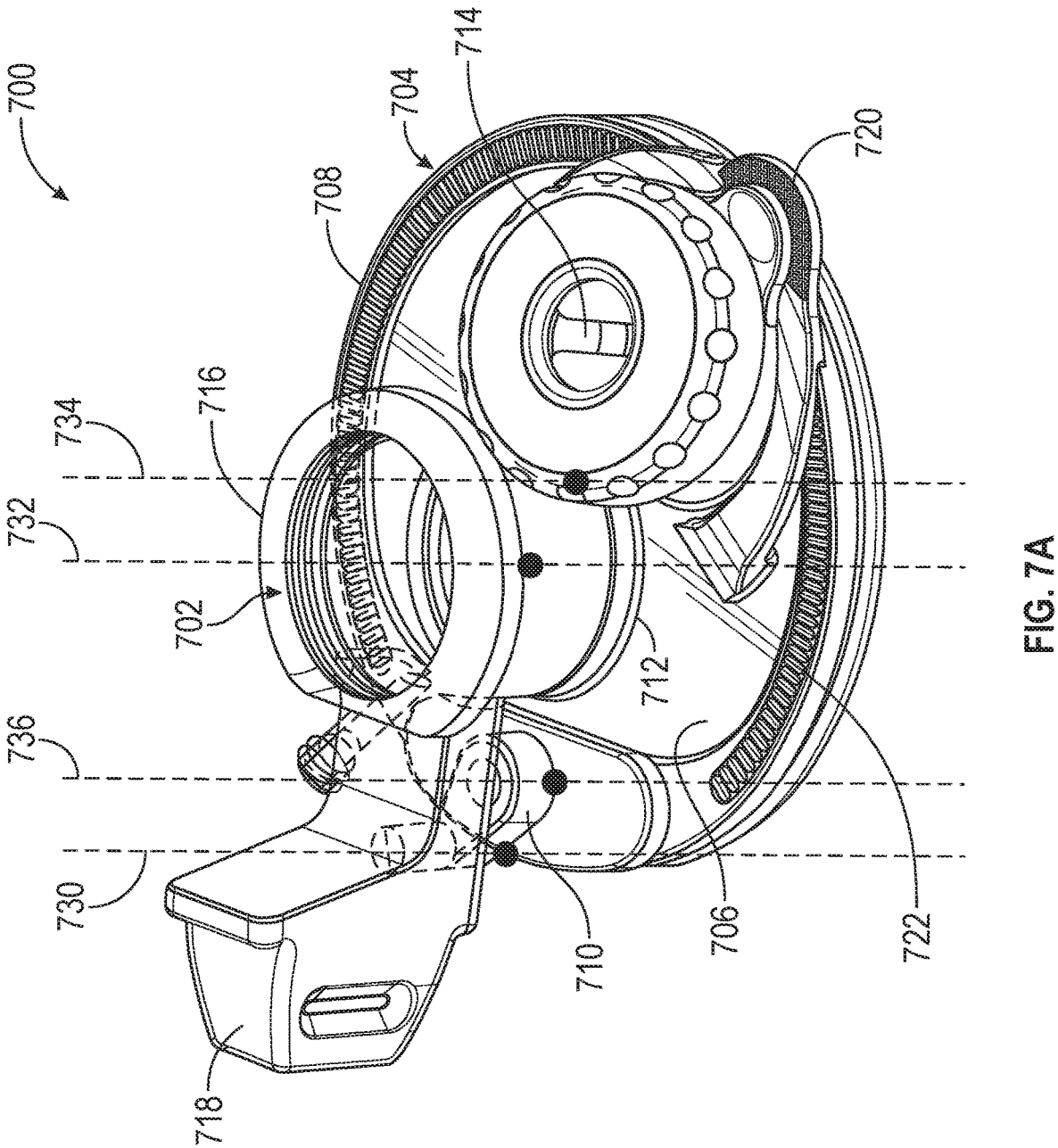
FIG. 7A is a top perspective view of another example instrument access device in accordance with various embodiments.

FIG. 7A is a top perspective view of proximal coupling component 700 of another instrument access device in accordance with various embodiments. The proximal coupling component 700 includes entry guide receptacle assembly 702 and countermotion assembly 704. The envelope (coupled to proximal coupling component) and clamp (disposed in and coupled to the distal opening of the envelope) of the instrument access device are not shown. The envelope and clamp are the same or similar to those depicted in FIGS. 4A and 4B for instrument access device 400.

Countermotion assembly 704 includes inner hub 706, outer rim 708, and crank arm 710. Inner hub 706 includes entry guide port 712 and assistant port 714. Entry guide port 712 and assistant port 714 are positioned eccentrically on inner hub 706. Outer rim 708 is coupled to the envelope. Inner hub 706 is rotatable relative to outer rim 708 about a central axis of outer rim 708. Entry guide receptacle assembly 702, which includes entry guide receptacle 716 and connector 718, is received in entry guide port 712. Crank arm 710 is pivotally connected to outer rim 708. Connector 718 affixes instrument access device 700 to an arm of a teleoperated surgical system, such as the system depicted and described with reference to FIG. 3.

Inner hub 706, outer rim 708, crank arm 710, and entry guide receptacle assembly 702 are connected to one another to form a linkage. The linkage is configured to rotate assistant port 714 around entry guide receptacle 716 without the envelope connected to outer rim 708 rotating about a central axis of the envelope. Thus, the linkage allows assistant port 714 to rotate around entry guide receptacle 716 without twisting the envelope.

In the example of FIG. 7A, inner hub 706, outer rim 708, crank arm 710, and entry guide receptacle assembly 702 are connected to one another to form a 4-bar linkage 724, more specifically, a parallel 4-bar linkage. Entry guide receptacle assembly 702 is the ground link of the 4-bar linkage, and crank arm 710 is the input link of the linkage. Inner hub 706 and outer rim 708 are each coupler links of the 4-bar parallel linkage formed by inner hub 706, outer rim 708, crank arm

710, and entry guide receptacle assembly 702. The four axes of rotation associated with the joints of the linkage 724, where pairs of adjacent links are coupled, are depicted with dashed lines in FIG. 7A. At the first axis 730, the crank arm 710 is coupled to the entry guide receptacle assembly 702 (at or near the connector 718 of the entry guide receptacle assembly 702). The second axis 732, which goes through the center of the entry guide port, corresponds to the joint that couples the entry guide receptacle assembly 702 to the inner hub 706. The third axis 734, which goes through the common center of the rim 708 and hub 706, corresponds to the joint that couples the hub 706 to the outer rim 708. The fourth axis 736, which is the pivot axis of the crank arm 710, couples the rim 708 to the crank arm 710. The distance between axes 730, 736 (the length of the crank-arm link) is equal to the distance between axes 732, 734 (the distance between the centers of the rim and the entry guide port), and the distance between axes 730, 732 is equal to the distance between axes 734, 736, such that the axes 730, 732, 734, 736 form a parallelogram.

Countermotion assembly 704 also includes a locking mechanism for locking linkage 724 from moving and thereby for locking assistant port 714 in a position relative to entry guide receptacle 716 and entry guide port 712. In FIG. 7A, lock arm 720 is deflectable relative to outer rim 708 and includes a catch on an underside of lock arm 720. Outer rim 708 includes ratchet teeth 722. Lock arm 720 is resilient and configured to lock into ratchet teeth 722. Lock arm 720 can be deflected to raise the lock arm out of engagement with ratchet teeth 722 and thereby unlock the linkage formed by inner hub 706, outer rim 708, entry guide receptacle assembly 702, and crank arm 710, which in turn allows assistant port 714 to rotate relative to and about entry guide receptacle 716 and entry guide port 712.

Figure 7B:
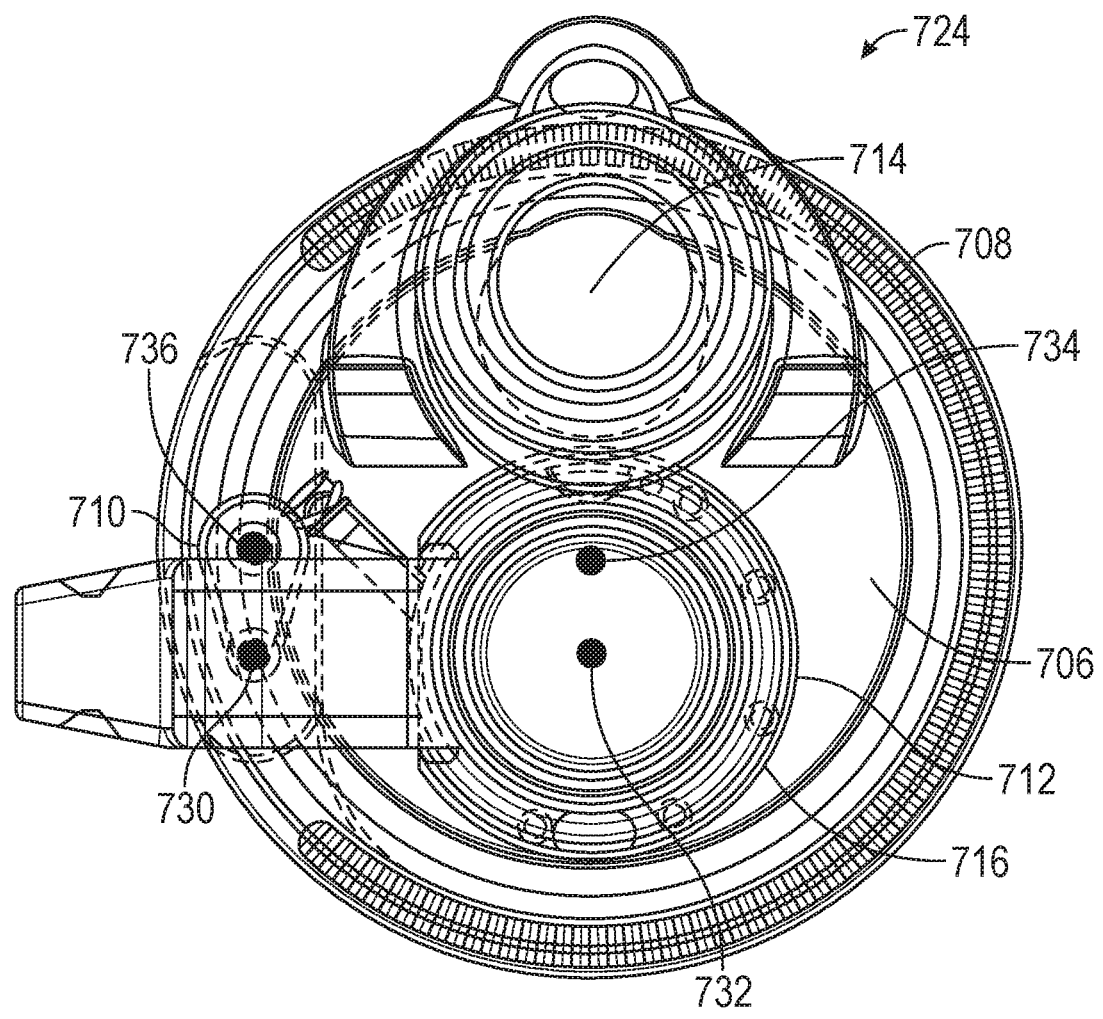
FIG. 7B is a top plan view depicting a linkage, in accordance with one embodiment, for rotating one port within an instrument access device as depicted in FIG. 7A around another port without twisting an envelope of the device.
Figure 7C:
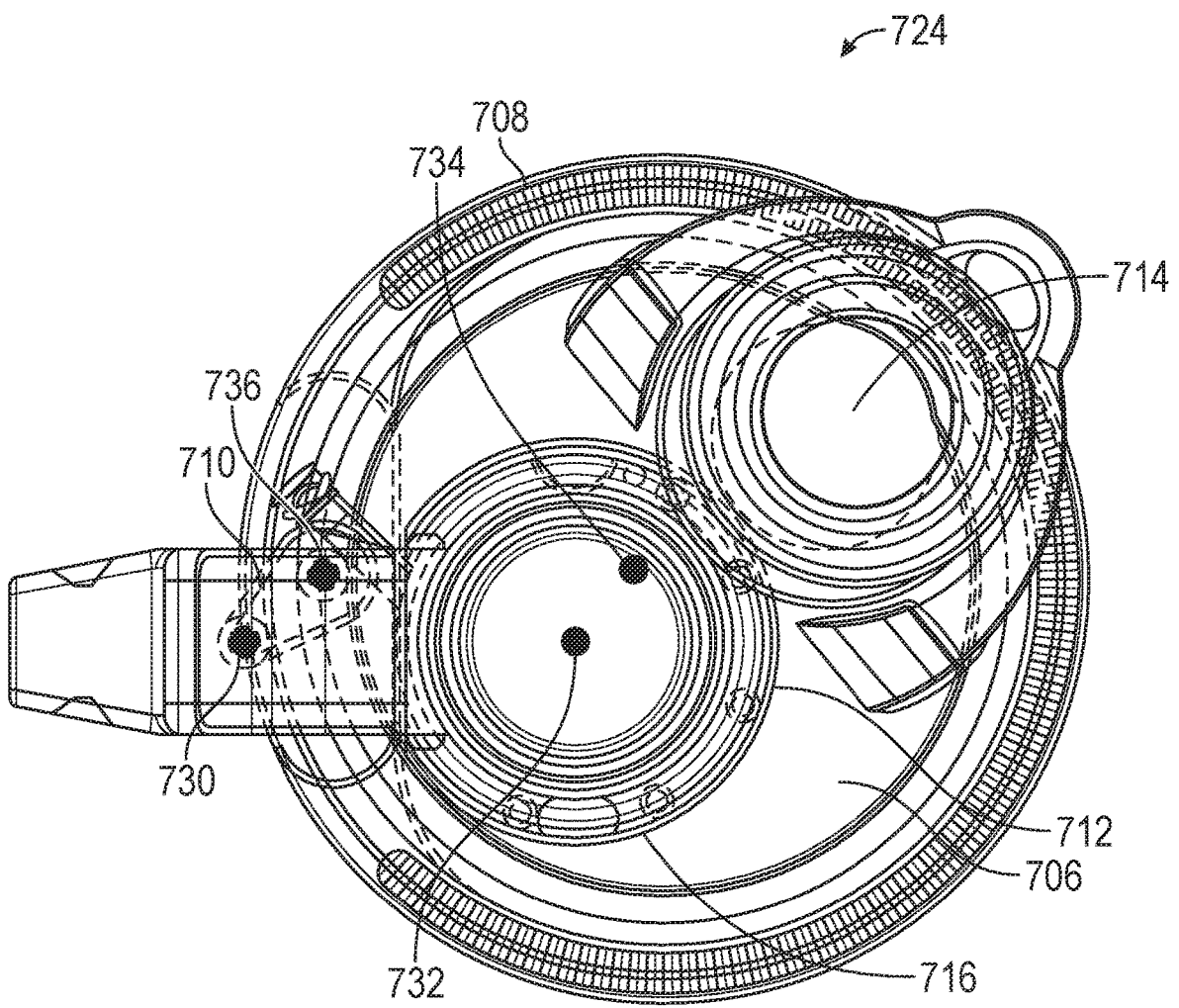
FIGS. 7C and 7D are top plan views depicting the linkage of FIG. 7B in different rotational positions.
Figure 7D:
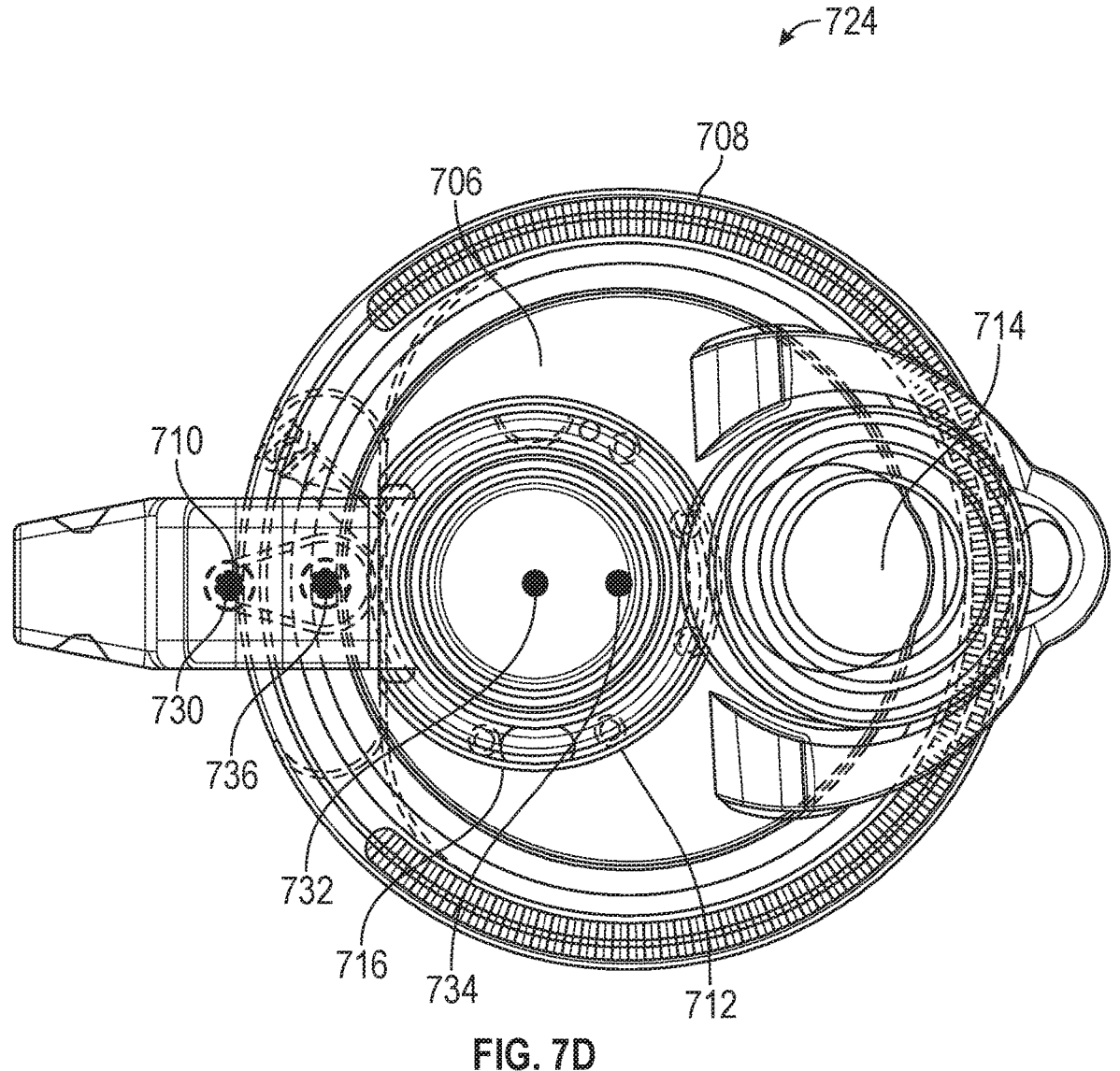

FIG. 7B is a plan view depicting linkage 724 formed by inner hub 706, outer rim 708, entry guide receptacle assembly 702, and crank arm 710. In the example of FIG. 7B, linkage 724 is depicted in a first position. To illustrate motion of linkage 724, and by association assistant port 714, linkage 724 is depicted in two additional positions in FIGS. 7C and 7D. The axes of rotation 730, 732, 734, 736 are indicated by black dots in these plan views. Referring to FIGS. 7B-7D, note first that entry guide receptacle 716 stays fixed in space and does not either translate or rotate relative to other components. Crank arm 710 is pivotable relative to inner hub 706 and outer rim 708. Pivoting crank arm 710 causes inner hub 706 to rotate relative to outer rim 708. Additionally, pivoting crank arm 710 causes outer rim 708, which is connected to the envelope, to translate without rotating about a central axis of outer rim 708. This is the manner in which assistant port 714 is able to rotate around entry guide receptacle 716 and entry guide port 712 without causing the envelope (which is coupled to outer rim 708) to twist.

Envelope

As noted above, examples according to this disclosure include an instrument access device that includes an envelope, and the envelope includes a distal opening at a distal end, a proximal opening at a proximal end, and a cavity between the distal and proximal ends and openings. The distal end of the envelope is coupled to a distal coupling component, which may be or include, e.g., a clamp. The clamp or other distal coupling component can, in turn, be coupled to a wound retractor or other port device. The proximal end of the envelope is coupled to a proximal coupling component, e.g., one including a countermotion assembly as described above. The instrument access device is configured to receive an insufflation gas and to maintain insufflation pressure within a cavity in the body of a patient and to maintain insufflation pressure within the cavity of the envelope. The pressurized and sealed envelope cavity provides an operating space for shafts of multiple instruments of a teleoperated surgical system to articulate outside the body such that instrument end effectors can be located at or near the surface of the body at the incision site of the wound retractor coupled to the instrument access device.

In examples according to this disclosure, the pressurized envelope is configured to allow shafts of multiple instruments of a teleoperated surgical system to triangulate within the cavity of the envelope. Thus, the envelope needs to provide enough space to allow multiple instruments to be manipulated within the cavity of the envelope and to allow a surgeon to triangulate the instruments to perform various procedures at or near the surface of the body at the incision site of the wound retractor coupled to the instrument access device. U.S. Pat. No. 9,060,678 B2 (filed Jun. 13, 2007) discloses aspects of instrument triangulation in a single-port surgical system and is herein incorporated by reference.

The pressurized envelope may be (but need not be) manufactured from a transparent material, including, for example, a transparent polymer. Beneficially, a transparent envelope provides visualization for a clinician to see the incision site to which the envelope is connected. In use of the instrument access device, the envelope is connected to a proximal coupling component (similar to the examples described above with reference to FIGS. 4A-7D) that can receive medical instruments via one or more ports (e.g., a primary entry guide port and an assistant port), and the envelope can provide visualization for the clinician for instruments introduced via these ports. When an opaque material is used for the envelope, visualization can be provided by an endoscopic camera inserted into the instrument access device via one of the ports, or optionally by one or more transparent windows in the envelope.

In various embodiments, the envelope of the instrument access device, when pressurized with insufflation gas or when constructed with sufficient rigidity, extends radially outward beyond the proximal and distal openings in the envelope (and thus beyond the portions of the proximal and distal coupling components received in the respective openings). Example shapes and configurations of the envelope are described with respect to FIGS. 8A-8F.

Figure 8A:
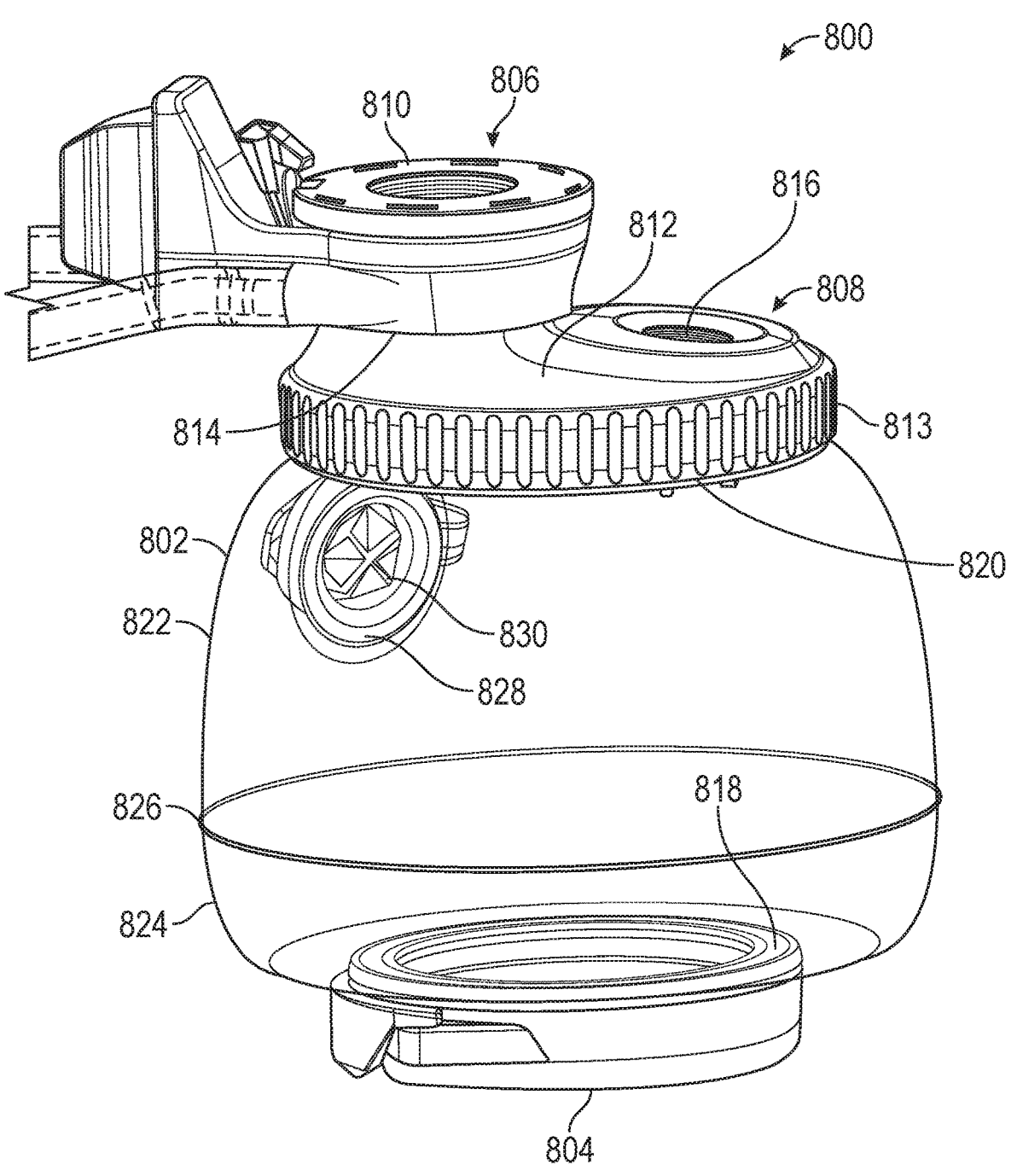
FIG. 8A is a perspective view of an example instrument access device including an ovoid envelope in accordance with one embodiment.

FIG. 8A is a perspective view depicting example instrument access device 800 according to various embodiments. In FIG. 8A, instrument access device 800 includes envelope 802, distal coupling component 804, entry guide receptacle assembly 806, and countermotion assembly 808. Entry guide receptacle assembly 806 and countermotion assembly 808 can be similar to the entry guide receptacle assemblies and countermotion assemblies described above with reference to FIGS. 4A-7D. For example, entry guide receptacle assembly 806 includes entry guide receptacle 810 and countermotion assembly 808 includes orbital element 812 having entry guide port 814 and assistant port 816, surrounded by outer element 813.

Envelope 802 includes distal opening 818 and proximal opening 820. Distal opening 818 of envelope 802 is coupled to and receives clamp (or other distal coupling component) 804, which is configured to be connected to a port device, such as a wound retractor assembly, at an incision site. Proximal opening 820 of envelope 802 is coupled to and receives countermotion assembly 808. Distal opening 818 of envelope 802 can be coupled to clamp 804 by a variety of means, including using an adhesive, or heat-sealing envelope 802 to clamp 804. Similarly, proximal opening 820 of envelope 802 can be coupled to countermotion assembly 808 by a variety of means, including using an adhesive, or heat-sealing envelope 802 to countermotion assembly 808 at the outer element 813.

As will be described in greater detail below, envelope 802 can be of a variety of shapes and sizes. In general, however, envelope 802, on condition that envelope 802 is pressurized with insufflation gas or if sufficiently rigid, extends radially outward beyond clamp 804 and countermotion assembly 808. In the example of FIG. 8A, envelope 802 includes proximal section 822 and distal section 824. Proximal section 822 of envelope 802 is coupled to distal section 824 at junction 826. Proximal section 822 can be coupled to distal section 824 by a variety of means, including using an adhesive, or heat-sealing proximal section 822 to distal section 824. Proximal section 822 and distal section 824 may each be a single contiguous piece, or be alternatively formed of multiple pieces. In multi-piece sections 822, 824, the proximal opening 820 may be formed in a first piece included in the proximal section 822, and the distal opening 818 may be formed in a second piece included in the distal section 824.

Proximal section 822 of envelope 802 can be a first convex section. Distal section 824 of envelope 804 can be a second convex section generally opposed to proximal convex section 822. The combination of proximal section 822 and distal section 824 can form an ovoid shape as shown (e.g., as characterized by two convex portions that meet at a common maximum diameter, but generally differ in height). As will be described in detail below, other shapes are also possible. In the depicted example, the maximum diameter of envelope 802 is located at junction 826 connecting proximal section 822 to distal section 824. In an example, the maximum diameter of envelope 802 is optionally larger than the longitudinal height of envelope 802. Additionally, junction 826 can be located below a transverse plane that bisects envelope 802 longitudinally (in a direction along a center axis defined through the distal and proximal openings 818 and 820 of the envelope). In other words, with proximal section 822 of the envelope 802 extending a first distance along the center axis and the distal section 824 of the envelope 802 extending along a second distance along the center axis, the second distance can be less than the first distance. Locating junction 826 below the longitudinal midpoint of envelope 802 can improve visualization for a clinician by providing a larger field of view through proximal section 822 that is unobstructed by junction 826.

Envelope 802 includes an optional additional assistant port 828. Envelope assistant port 828 includes seal 830, which is received in port 828 of envelope 802. Envelope assistant port seal 830 is configured to receive and seal a manually operated instrument and can include a variety of types of seals, including a cross-slit, duckbill, wiper, and/or septum seal. In the example of FIG. 8A, envelope assistant port seal 830 includes a cross-slit seal. In another example, envelope assistant port seal 830 includes a seal similar to the seals disclosed in International Application No. PCT/US2019/031393 (filed May 8, 2019), which is herein incorporated by reference.

Envelope 802 (and other envelopes in accordance with this disclosure) can be manufactured from a variety of materials, including a variety of transparent polymers. In an example, envelope 802 is manufactured from acetates, polyester, vinyl, or urethanes (e.g., thermoplastic polyurethane (TPU)). Envelope 802 can be manufactured in a variety of ways, including vacuum forming. In another example, envelope 802 is manufactured from a flat panel with multiple seams, which are joined to one another to form the final shape of envelope 802.

Figure 8B:
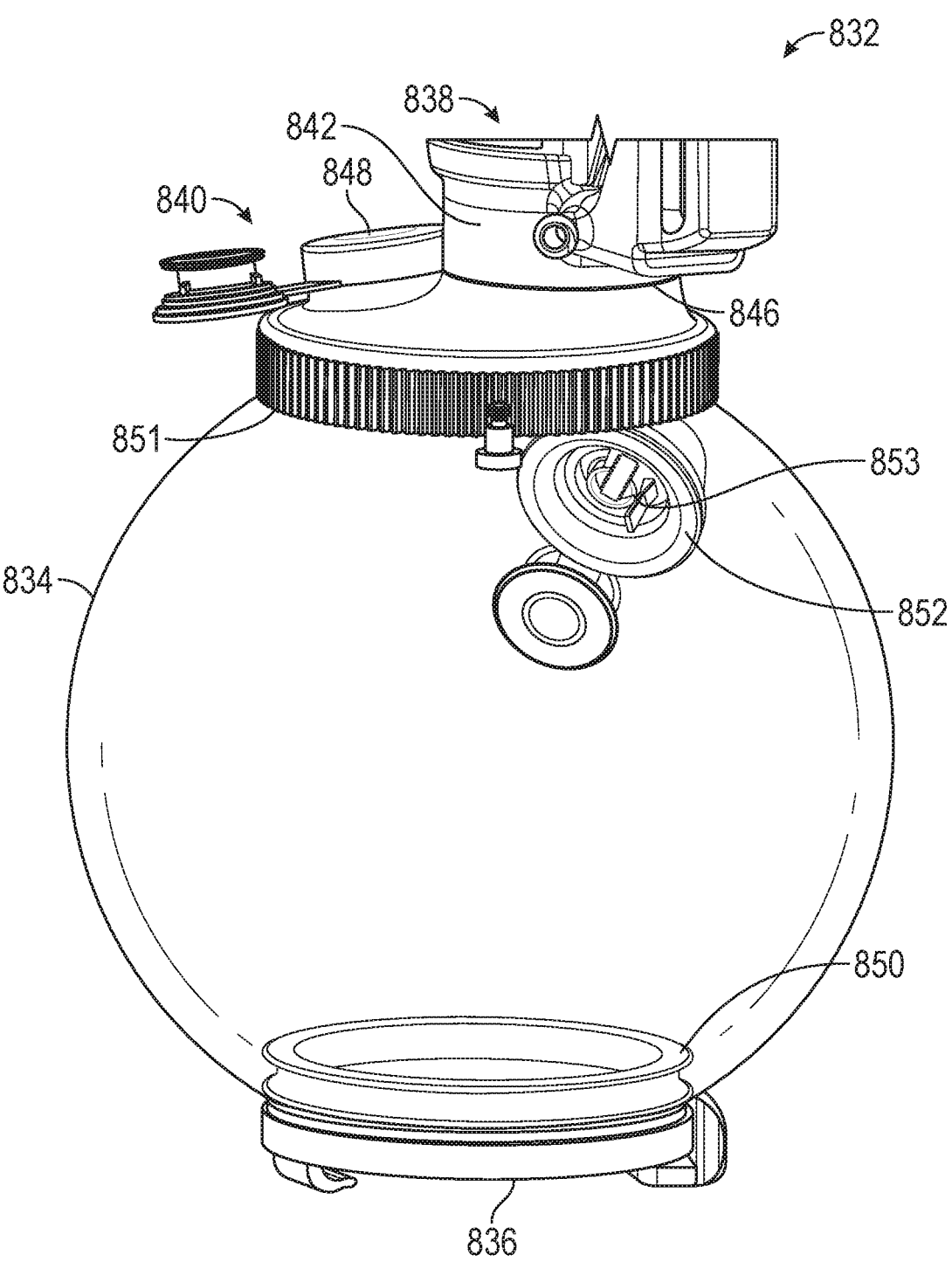
FIG. 8B is a perspective view of an example instrument access device including a spherical envelope in accordance with one embodiment.

FIGS. 8B-8F are perspective views depicting additional example envelopes in accordance with this disclosure. The same materials as listed above may be used for the envelopes of FIGS. 8B-8F as well. In FIG. 8B, instrument access device 832 includes envelope 834, clamp 836, entry guide receptacle assembly 838, and countermotion assembly 840. Entry guide receptacle assembly 838 and countermotion assembly 840 can be similar to the entry guide receptacle assemblies and instrument seal assemblies described above with reference to FIGS. 4A-7D.

Envelope 834 includes distal opening 850 and proximal opening 851. Distal opening 850 of envelope 834 is coupled to and receives clamp 836, which is configured to be connected to a port device, such as a wound retractor assembly at an incision site. Proximal opening 851 of envelope 834 is coupled to and receives countermotion assembly 840. Distal opening 850 of envelope 834 can be coupled to clamp 836 by a variety of means, including using an adhesive, or heat-sealing envelope 834 to clamp 836. Similarly, proximal opening 851 of envelope 834 can be coupled to countermotion assembly 840 by a variety of means, including using an adhesive or heat-sealing envelope 834 to countermotion assembly 840 at the outer element.

In the example of FIG. 8B, envelope 834 has a substantially spherical shape (allowing for some deviations from perfect spherical shape, e.g., to accommodate for the proximal and distal openings). Although not depicted in FIG. 8B, in examples, spherical envelope 834 may be formed from two or more semi-spherical sections joined together at a seam or other junction.

Envelope 834 includes, optionally, an additional assistant port 852. Envelope assistant port 852 includes seal 853, which is received in port 852 of envelope 834. Envelope assistant port seal 853 is configured to receive and seal a manually operated instrument and can include a variety of types of seals, including a cross-slit, duckbill, wiper, and/or septum seal. In the example of FIG. 8A, envelope assistant port seal 853 includes a cross-slit seal. In another example, envelope assistant port seal 853 includes a seal similar to seals disclosed in International Application No. PCT/US2019/031393.

Envelope 834 can be manufactured in a variety of ways, including vacuum forming. In another example, envelope 834 is manufactured from a flat panel with multiple seams, which are joined to one another to form the final shape of envelope 834.

Figure 8C:
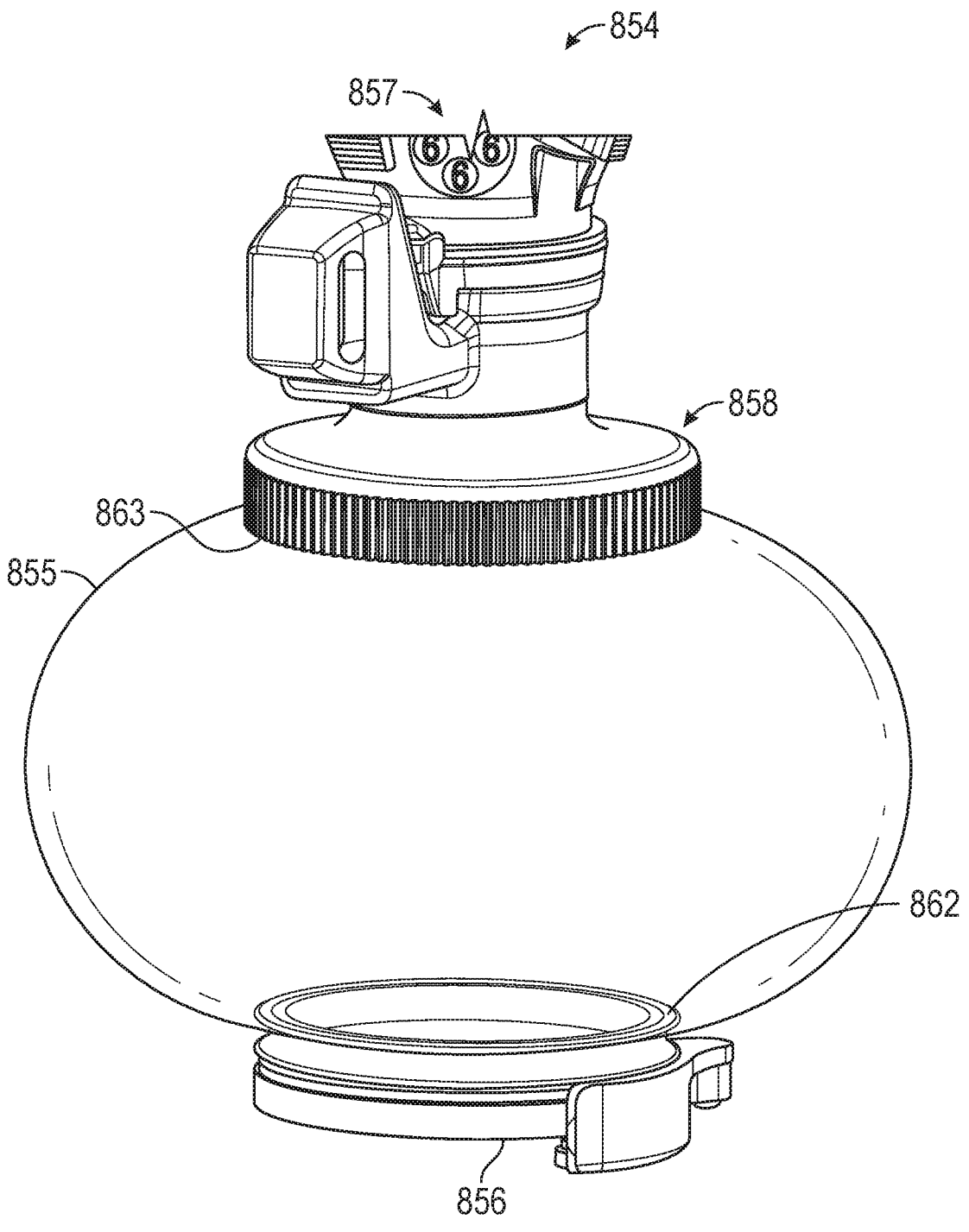
FIG. 8C is a perspective view of an example instrument access device including an oblate spherical envelope in accordance with one embodiment.

Referring now to FIG. 8C, instrument access device 854 includes envelope 855, clamp 856, entry guide receptacle assembly 857, and countermotion assembly 858. Entry guide receptacle assembly 857 and countermotion assembly 858 can be similar to the entry guide receptacle assemblies and instrument seal assemblies described above with reference to FIGS. 4A-7D.

Envelope 855 includes distal opening 862 and proximal opening 863. Distal opening 862 of envelope 855 is coupled to and receives clamp 856, which is configured to be connected to a port device, such as a wound retractor assembly at an incision site. Proximal opening 863 of envelope 855 is coupled to and receives countermotion assembly 858. Distal end 862 of envelope 855 can be coupled to clamp 856 by a variety of means, including using an adhesive, or heat-sealing envelope 855 to clamp 856. Similarly, proximal end 863 of envelope 855 can be coupled to countermotion assembly 858 by a variety of means, including using an adhesive, or heat-sealing envelope 855 to countermotion assembly 858 at the outer element.

In the example of FIG. 8C, envelope 855 has an oblate spheroid shape. Although not depicted in FIG. 8C, in examples, oblate spheroid envelope 855 may be formed from two or more semi-spheroid sections which are joined together at a seam or other junction. Although not depicted in FIG. 8C, envelope 855 can optionally include an additional assistant port having an assistant port seal as described above.

Figure 8D:
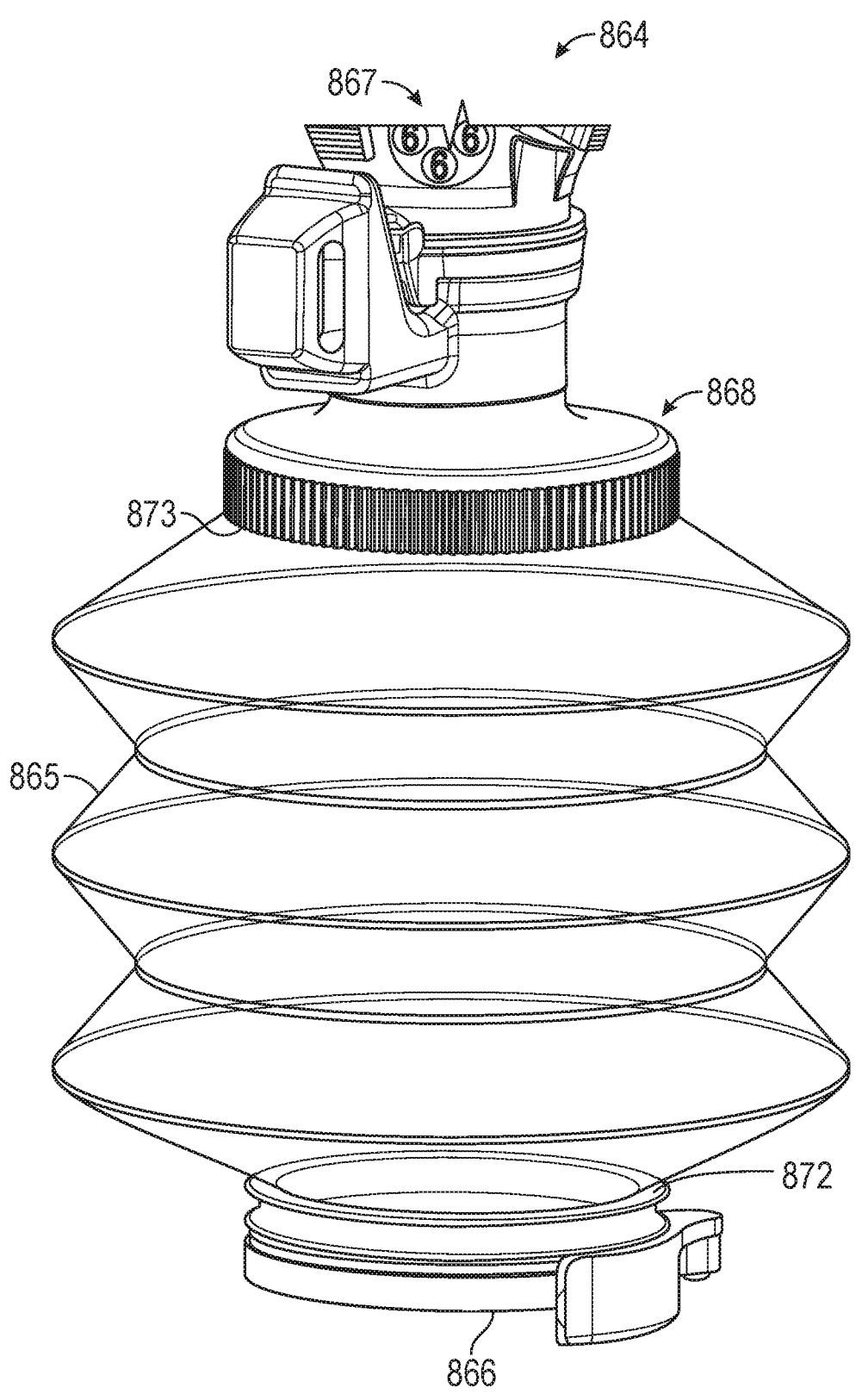
FIG. 8D is a perspective view of an example instrument access device including a bellows-shaped envelope in accordance with one embodiment.

In FIG. 8D, instrument access device 864 includes envelope 865, clamp 866, entry guide receptacle assembly 867, and countermotion assembly 868. Entry guide receptacle assembly 867 and countermotion assembly 868 can be similar to the entry guide receptacle assemblies and instrument seal assemblies described above with reference to FIGS. 4A-7D.

Envelope 865 includes distal opening 872 and proximal opening 873. Distal opening 872 of envelope 865 is coupled to and receives clamp 866, which is configured to be connected to a port device, such as a wound retractor assembly at an incision site. Proximal opening 873 of envelope 865 is coupled to and receives countermotion assembly 868. Distal end 872 of envelope 865 can be coupled to clamp 866 by a variety of means, including using an adhesive, or heat-sealing envelope 865 to clamp 866. Similarly, proximal end 873 of envelope 865 can be coupled to countermotion assembly 868 by a variety of means, including using an adhesive, or heat-sealing envelope 865 to countermotion assembly 868 at the outer element.

In the example of FIG. 8D, envelope 865 has a generally cylindrical shape, and more specifically a cylindrical bellows shape. Although not depicted in FIG. 8D, in examples, bellows-shaped envelope 865 may be formed from two or more sections joined together at seam(s) or other junction(s). Additionally, although not depicted in FIG. 8D, envelope 865 can optionally include an additional assistant port having an assistant port seal.

Figure 8E:
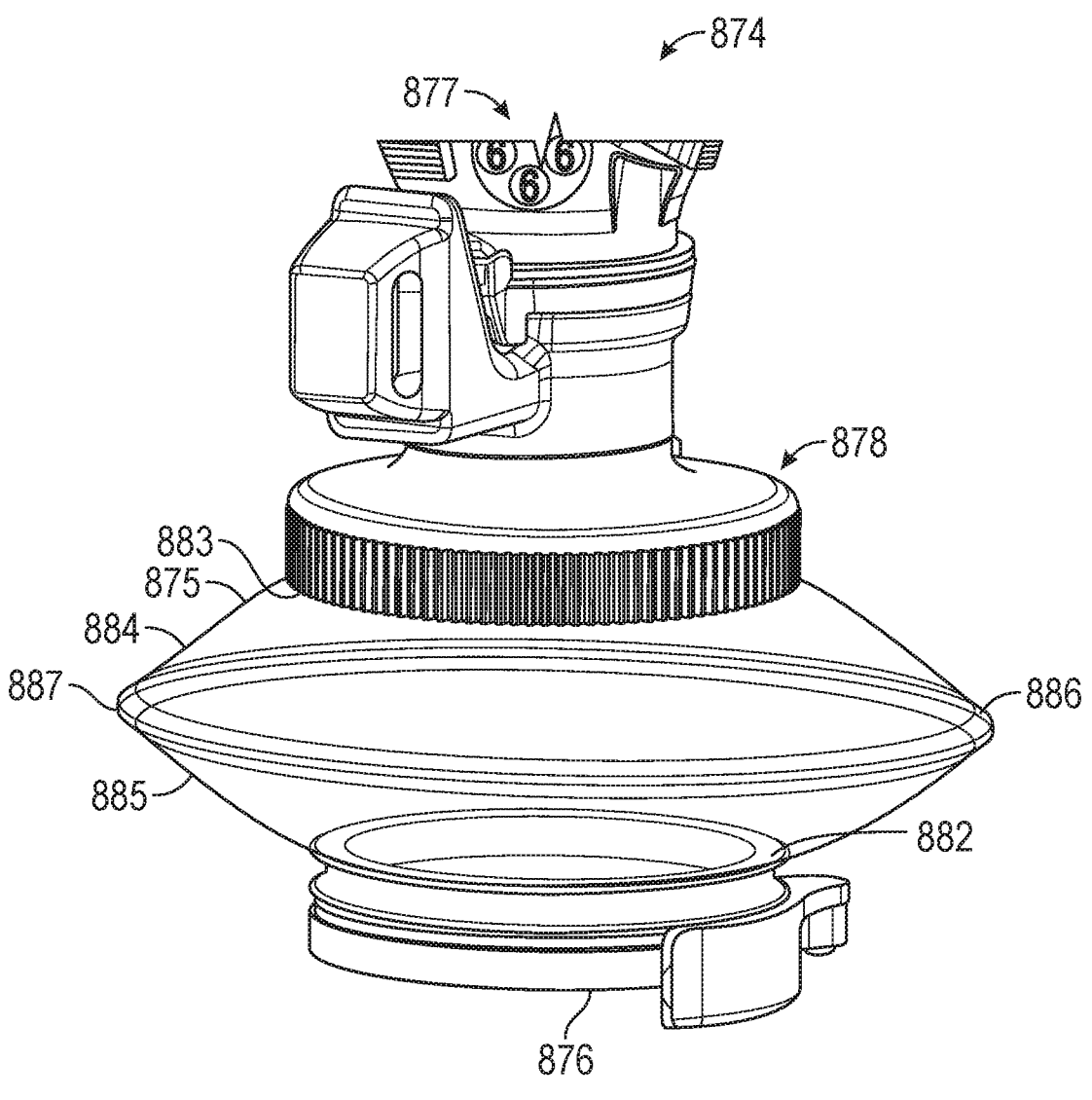
FIG. 8E is a perspective view of an example instrument access device including a lenticular envelope in accordance with one embodiment.

In FIG. 8E, instrument access device 874 includes envelope 875, clamp 876, entry guide receptacle assembly 877, and countermotion assembly 878. Entry guide receptacle assembly 877 and countermotion assembly 878 can be similar to the entry guide receptacle assemblies and instrument seal assemblies described above with reference to FIGS. 4A-7D.

Envelope 875 includes distal opening 882 and proximal opening 883. Distal opening 882 of envelope 875 is coupled to and receives clamp 876, which is configured to be connected to a port device, such as a wound retractor assembly at an incision site. Proximal opening 883 of envelope 875 is coupled to and receives countermotion assembly 878. Distal end 882 of envelope 875 can be coupled to clamp 876 by a variety of means, including using an adhesive, or heat-sealing envelope 875 to clamp 876. Similarly, proximal opening 883 of envelope 875 can be coupled to countermotion assembly 878 by a variety of means, including using an adhesive, or heat-sealing envelope 875 to countermotion assembly 878.

In the example of FIG. 8E, envelope 875 has a lenticular shape. The lenticular-shaped envelope 875 includes first and second convex sections 884, 885 sharing a common maximum diameter. The two convex sections 884, 885 are positioned opposite one another, and they are joined in an equatorial region 886, where the common maximum diameters of the two sections 884, 885 meet. In the example of FIG. 8E, the envelope 875 includes rib 887 at the equatorial region 886, and rib 887 extends radially outward from first convex section 885 and second convex section 886. Rib 887 provides structural support around the perimeter of equatorial region 886 to prevent, for example, inward buckling of the lenticular shape at the equatorial region 886 under insufflation pressure.

The two sections 884, 885 of lenticular-shaped envelope 875 may be symmetrical as shown, or they may be of different sizes. For example, proximal convex section 884 may have a larger longitudinal height than distal convex section 885 to provide enhanced visibility inside the envelope as described above. The proximal and convex sections may be joined together at seam(s) or other junction(s). Additionally, although not depicted in FIG. 8E, envelope 865 can optionally include an additional assistant port having an assistant port seal as described above.

Figure 8F:
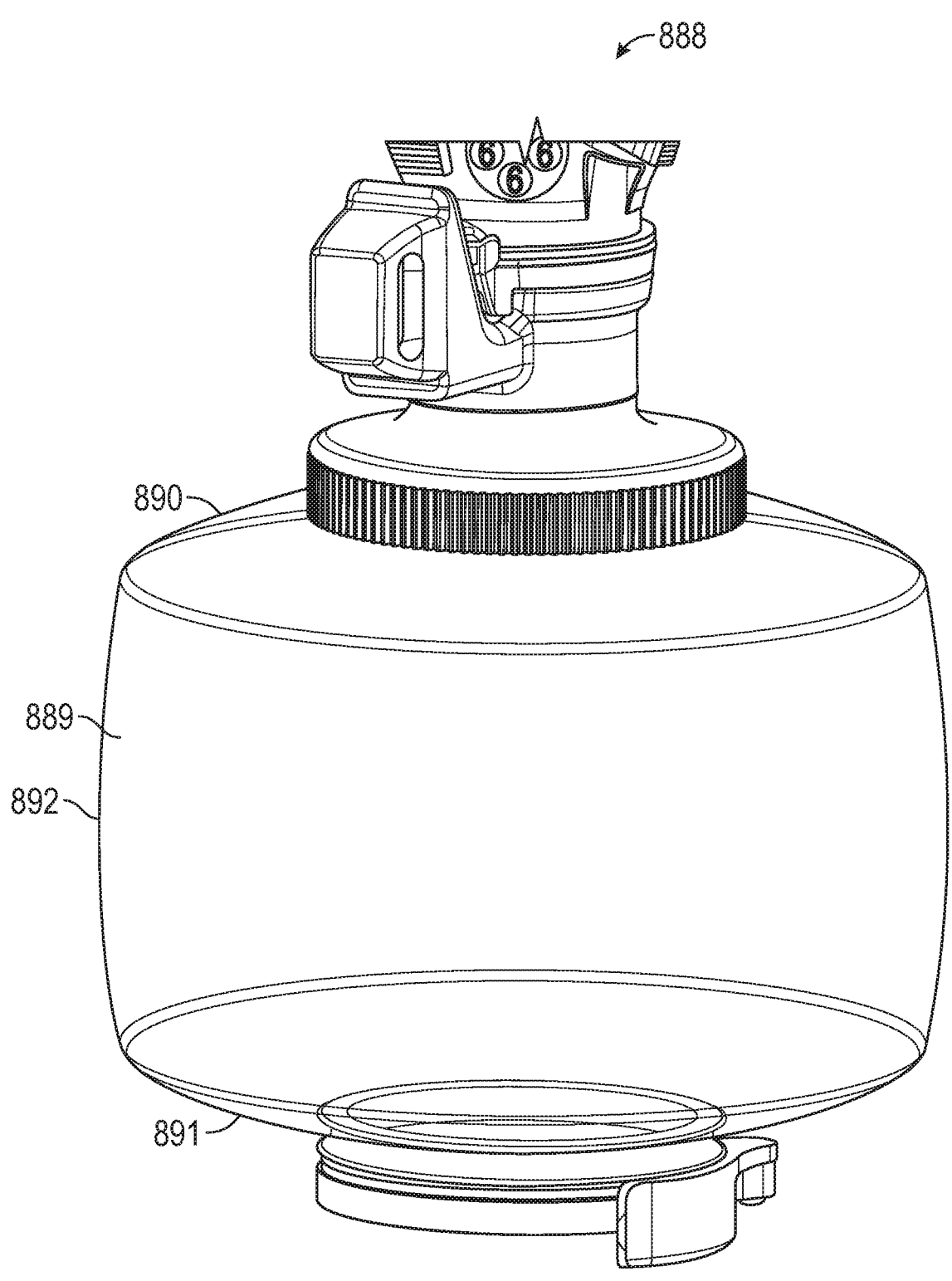
FIG. 8F is a perspective view of an example instrument access device including a barrel-shaped envelope in accordance with one embodiment.

In FIG. 8F, instrument access device 888 includes envelope 889. Instrument access device 888 can be substantially similar to instrument access device 874 of FIG. 8E, except that its envelope 889, instead of being lenticular-shaped like envelope 875, includes an elongated vertical section 892 between the two (e.g., convex) top and bottom sections 890, 891. Thus, envelope 889 generally has the shape of a barrel (e.g., bulging outward in the center, or, alternatively, being substantially cylindrical) bounded at the top and bottom by convex or, alternatively, flat or generally flat surfaces. Envelope 889, when pressurized with insufflation gas, extends radially outward beyond a clamp or other distal coupling component as well as beyond the countermotion assembly of a proximal coupling component. Envelope 889 may include an assistant port and seal (not shown) as described above.

Entry Guide

As explained above, various instrument access devices in accordance with this disclosure (e.g., devices 400, 700, 800, 832, 854, 864, 874, 888) are configured to receive an instrument entry guide in an entry guide receptacle located in an entry guide port of the instrument access device. An example such entry guide is described in the following disclosure.

Figure 9A:
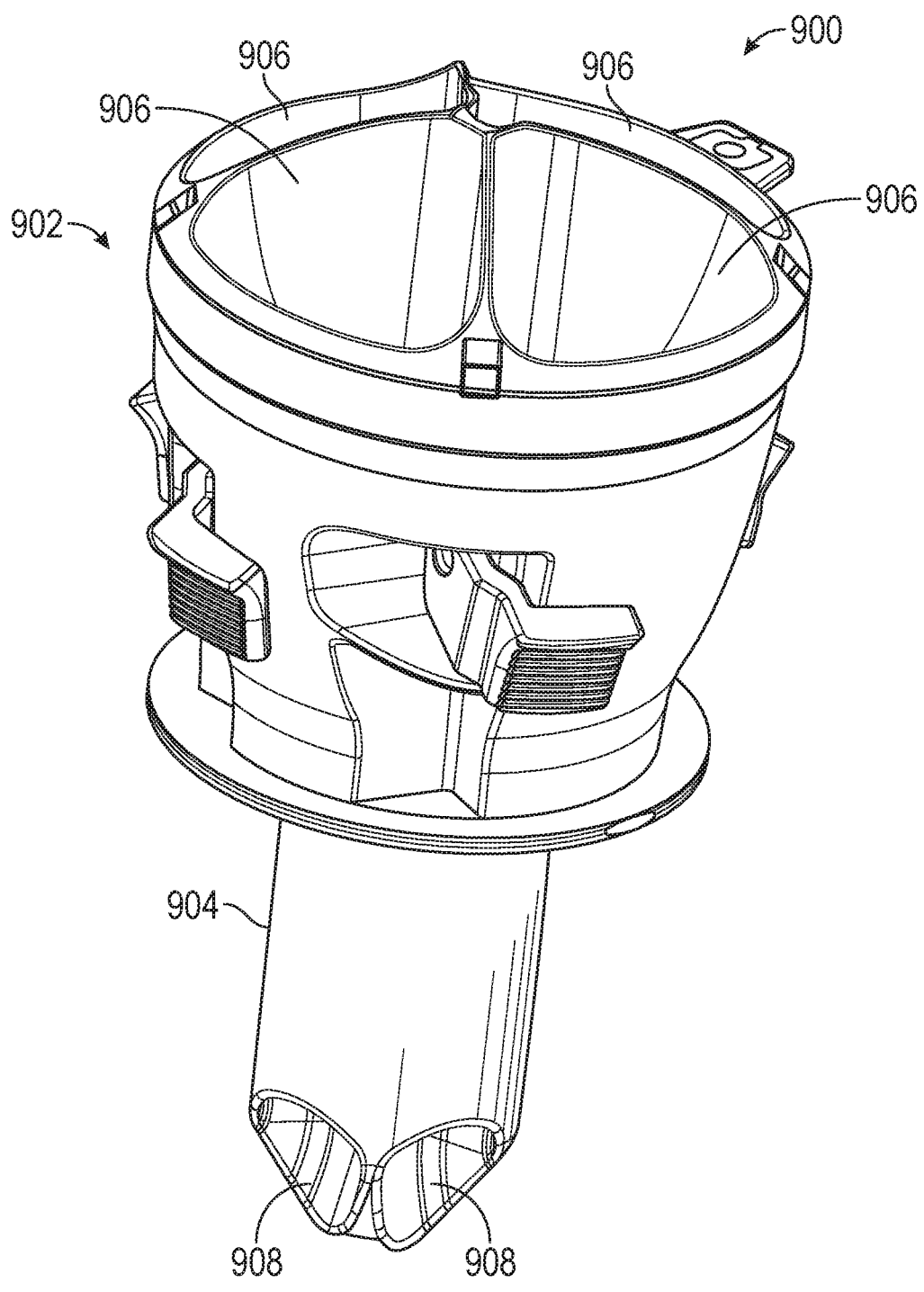
FIG. 9A is a perspective view of an entry guide in accordance with various embodiments.

FIG. 9A is a perspective view of an instrument entry guide 900 in accordance with various embodiments. The entry guide 900 includes a funnel portion 902 at the proximal end and, connected to the distal end of the funnel portion 902, a shaft portion 904. Multiple instrument channels are defined in entry guide 900, and each instrument channel includes an optional proximal tapered lead-in portion 906 in funnel portion 902 and a distal lumen 908 in shaft portion 904. Four instrument channels are shown, and other optional implementations may include two, three, or more instrument channels. Each instrument channel is configured to receive and guide an instrument through the entry guide to emerge from the distal end of the lumen 908. The cross sections of the instrument channels may all have the same size and shape, or they may vary in size and/or shape to guide different instruments through the entry guide.

Figure 9B:
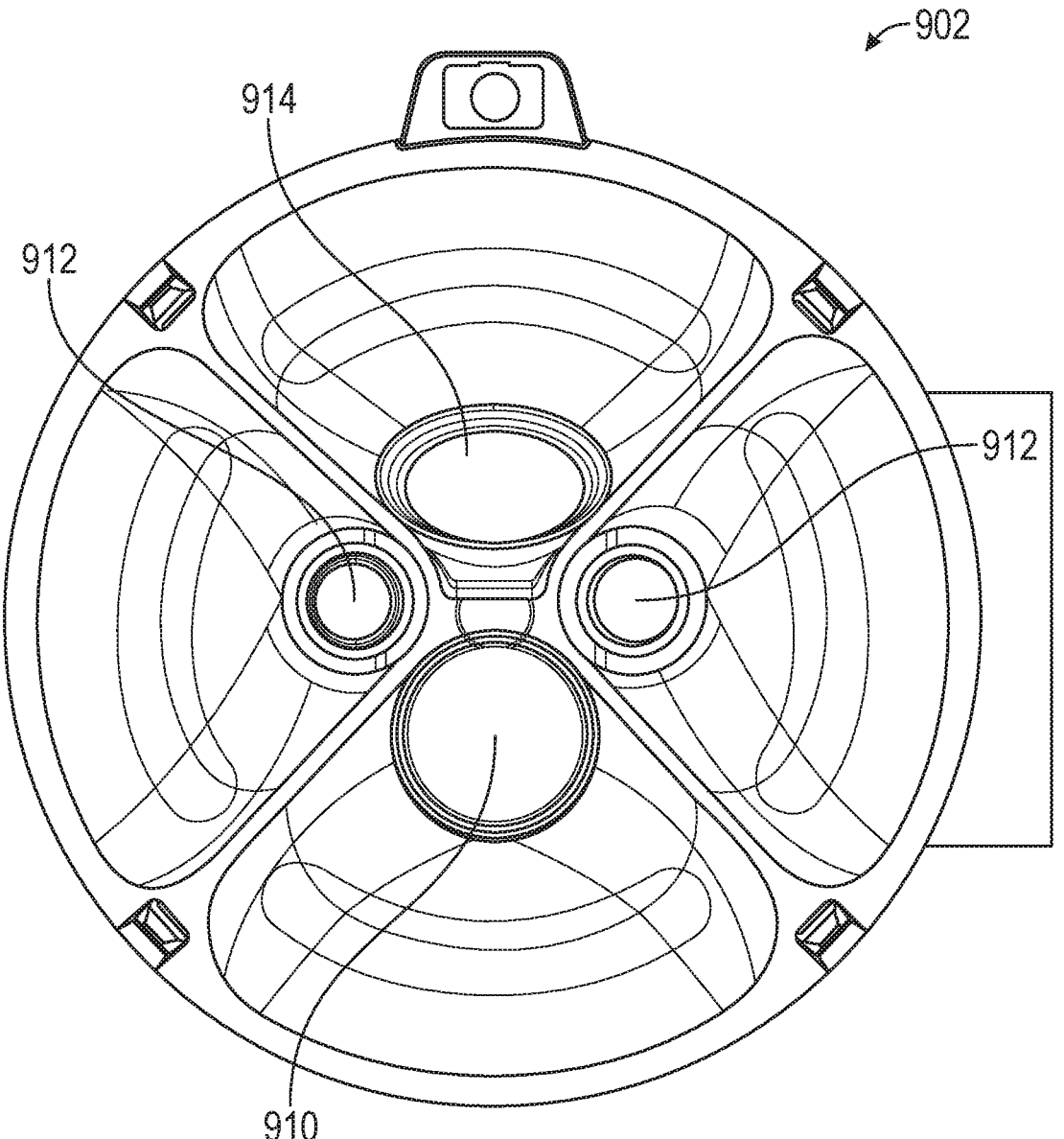
FIG. 9B is a top view of the proximal end of the entry guide of FIG. 9A.

FIG. 9B is a top view of entry guide 900, showing the funnel portions 902 and its tapered lead-in portions 906 at the proximal end of the entry guide 900 of FIG. 9A. FIG. 9B illustrates instrument channels (lead-in portions 906 and lumens 908) of different cross-sectional shapes and sizes in accordance with one embodiment. One lumen 910 has a relatively larger round cross section than round cross section lumens 912. In one optional implementation, lumen 910 is sized to receive an instrument comprising an instrument shaft with a diameter of 14 millimeters or less, such as diameters in the range of 10-14 millimeters. Two lumens 912 have relatively smaller round cross sections than lumen 910. These lumens 912 are optionally sized to each receive an instrument with an instrument shaft having a diameter of 7 millimeters or less, such as diameters that are approximately 6.5 millimeters. The cross section of the fourth lumen 914 is oval in shape, and it is suitable to accommodate, e.g., a camera instrument. The relative sizes and cross-sectional shapes of the lumens 910, 912, 914 illustrate that various combinations of lumen sizes and cross section shapes may be used in implementations of entry guide 900.

Figure 9C:
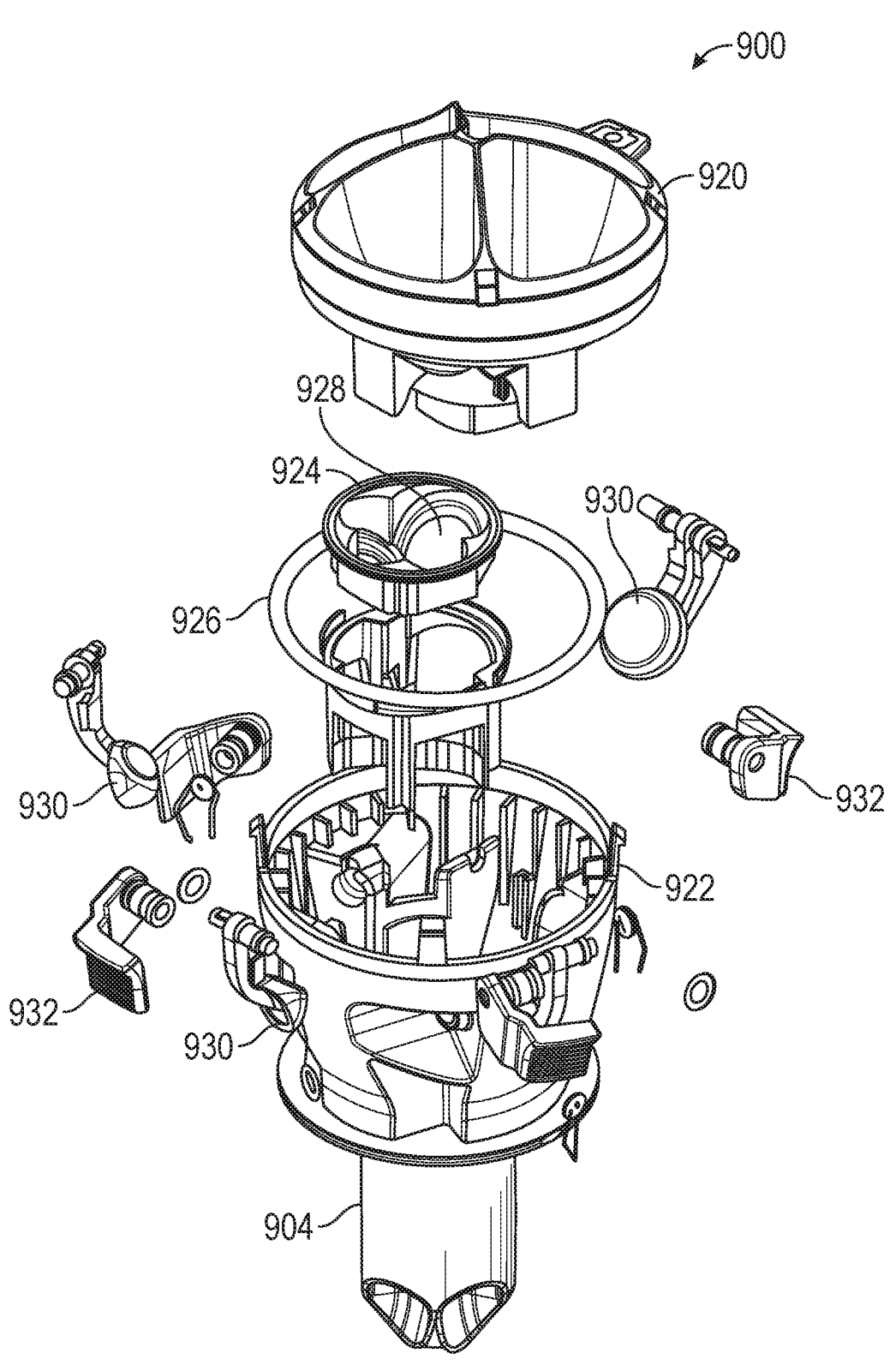
FIG. 9C is an exploded perspective view depicting additional details of the entry guide of FIG. 9A.

FIG. 9C is an exploded perspective view of the entry guide 900 that illustrates further detail. As shown, the funnel portion 902 may be formed of two parts: an upper part 920 and a lower part 922. The lower part 922 optionally may be integrally formed with the shaft 904. The entry guide 900 further includes an instrument seal 924 captured between the upper and lower parts 920, 922 of the funnel portion 902. The seal may be made, e.g., of silicone. During manufacturing, the instrument seal 924 can be seated in the lower part 922, and the upper part 924 can then be snapped into the lower part 922, with an O-ring 926 sealing the two parts along their rims. The instrument seal 924 includes seal openings 928 aligned with the instrument channels 906 and lumens 908, and the seal openings 928 are sized and shaped to accommodate an associated instrument outer diameter. The entry guide 900 further includes pivoting seal doors 930 each aligned with one of the seal openings 928 and the associated instrument channel 906. In some embodiments, the entry guide also includes levers 932 to manually operate the doors 930. (Some, but not all, of the pivoting doors 930 and levers 932 are shown exploded off to the side.)

The doors 930 may be spring-loaded and biased to the closed state. In its closed state, each door engages with and seals against the instrument seal 924, with a sealing portion of the door sealing one of the seal openings 928. When an instrument is inserted through a lead-in portion 906 of the funnel portion 902 and into a corresponding lumen in the shaft 904, the door 930 associated with the lumen is pushed open. When a door 930 is in an open state, the lip of corresponding seal opening 928 seals against the shaft of the instrument extending through the corresponding instrument channel. The instrument seal 924 in conjunction with the sealing door 930 prevents insufflation gas from escaping through an instrument channel when no instrument is inserted and from escaping between the inner wall of the channel and the instrument shaft when an instrument is inserted. Further details of entry guides and associated sealing aspects are described in U.S. Pat. No. 9,629,681 B2 (filed Mar. 14, 2014)(disclosing "Sealing Multiple Surgical Instruments"), which is herein incorporated by reference.

Figure 9D:
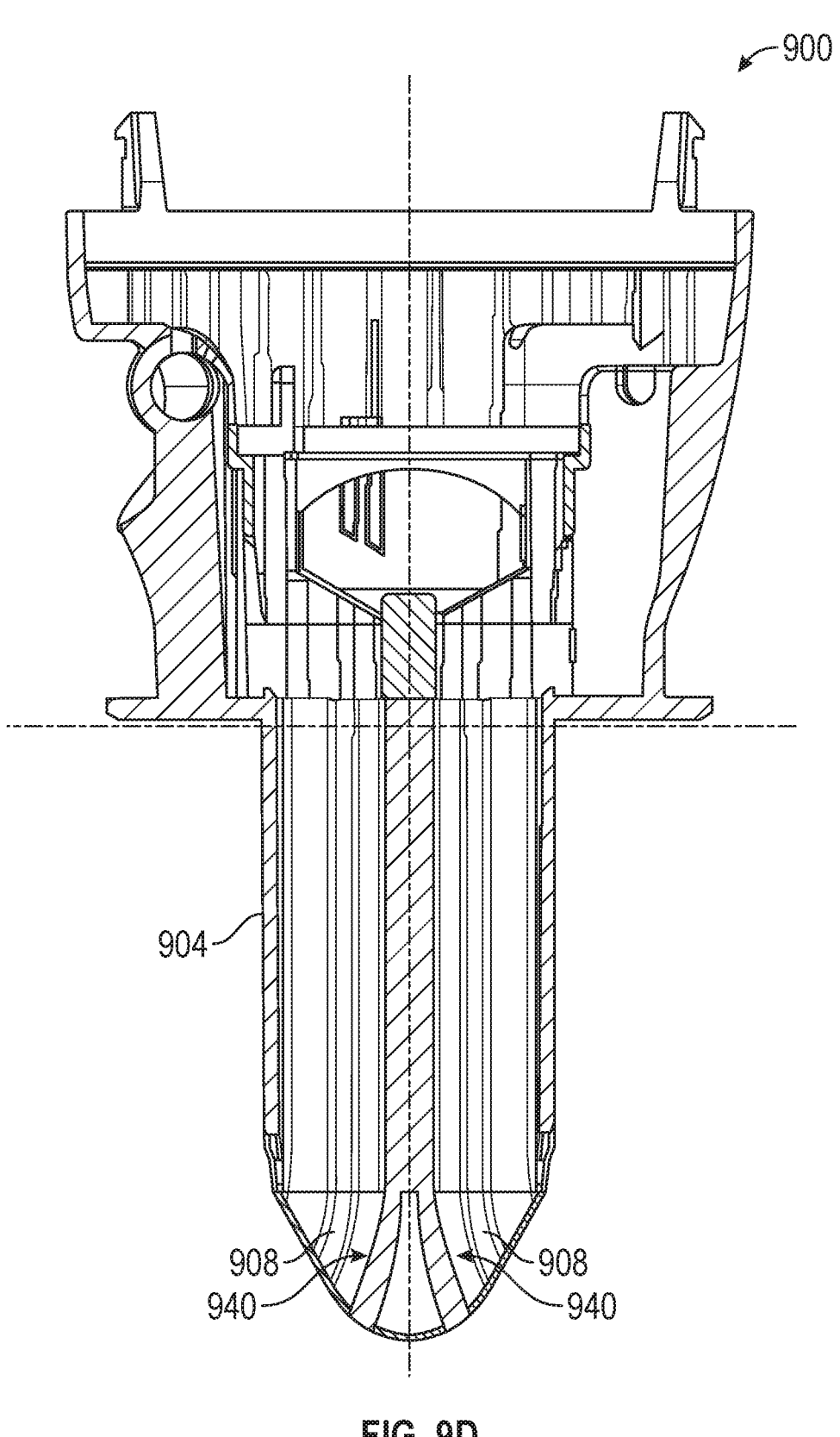
FIG. 9D is a cross-section taken along a longitudinal axis of the entry guide of FIG. 9A.

FIG. 9D is a cross-sectional view of the entry guide 900, taken along a longitudinal axis of the entry guide 900 (i.e., along the direction of the shaft 904). Unlike prior entry guides, entry guide 900 is configured to slightly bend the shafts of one or more of the inserted instruments. In prior entry guide configurations, the instrument channels in an entry guide are configured so that instrument shafts, despite entering the instrument channels in the funnel portion 902 from generally different directions, exit the lumens 908 of the shaft 904 substantially parallel to each other and to the longitudinal axis of the entry guide 900 (e.g., deviating from the longitudinal axis by no more than 1 degree). In prior entry guides, this reorientation of the instrument shafts to be generally parallel is achieved by curving the distal ends of the lumens 908 slightly radially outward, compensating for the remaining orientational bias of the instrument shafts that results from the radially inward component of their orientation where they enter the instrument channels. But this straightening effect is insufficient to keep the instrument shafts parallel upon exiting the lumens 908 when the length of the shaft 904 of the entry guide 900 is shortened, e.g., to minimize the space the shaft 904 takes up inside the envelope of an instrument access device in accordance with the present disclosure. Thus, if the entry guide shaft 904 is shortened without further compensating for the inward orientational bias of resiliently bendable instrument shafts entering the proximal end of the entry guide, the instrument shafts will cross or collide after they exit the entry guide lumens 908.

To remedy this problem and keep the instrument shafts parallel at the exit of the lumens 908 of a shortened entry guide, one or more of the lumens 908 are modified to include a small projection 940 at their distal ends. Projection 940 extends radially inward into to the lumen 908 to deflect the instrument shaft extending through the lumen radially outward from the lumen's centerline and the entry guide's central axis. The projection 940 in a lumen may be positioned on the central junction between the multiple lumens such that it points away from the central axis of the entry guide shaft 904. The projection 940 is sized and shaped to deflect and orient a shaft of an instrument parallel to the longitudinal axis of the entry guide shaft 904. The size and shape of the projection 940 may, for instance, depend on the flexibility of the instrument shaft of the instrument intended to be received in the respective lumen 908. Some instruments extending through instrument channels in entry guide 900 may have shafts that are sufficiently rigid that no projection 940 is required at the distal end of these instruments' corresponding instrument channel. And so, for example, an entry guide 900 as depicted in FIG. 9B may have projections at the ends of the three lumens 910, 912 intended to receive surgical instruments, whereas the lumen 914 for the camera may lack such a projection because the camera shaft is sufficiently rigid. In general, however, an entry guide in accordance herewith may include inward projections 940 in any one or more, including all, lumens.

In some embodiments the projection 940 at the distal end of lumen 908 forms a ramp that defines a lumen diameter that decreases from a proximal end of the ramp to a distal end of the ramp, and the ramp is positioned toward a center of the shaft 904 at the junction between the lumens 908.

In accordance with a further aspect, entry guide 900 may optionally include a relief that defines an aperture in the outer periphery of the entry guide shaft 904 at a position opposite to the projection or ramp. This aperture extends the diameter of the lumen 908 outward and so allows for the extra bend in the instrument shaft. That is, the aperture provides extra room for the instrument shaft to bend outward, where the shaft would otherwise contact the outer wall of the lumen. Although the projections as described above reorient the instrument shafts into a generally parallel configuration after exiting the distal end of the entry guide, in optional alternate embodiments the projections in the lumens 108 are configured to deliberately spread the instruments laterally to a laterally converging orientation or to a laterally diverging orientation. In the laterally converging orientation, the projections still spread the instrument shafts sufficiently to prevent the instruments from colliding during normal operation. In the laterally diverging orientation, the projections spread the instrument shafts to provide additional spacing between the instruments.

Torque Limiting Clutch

Figure 10A:
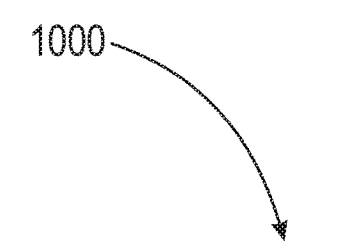
FIGS. 10A-10C depict an example medical device including a clutch in accordance with examples of this disclosure.
Figure 10A:
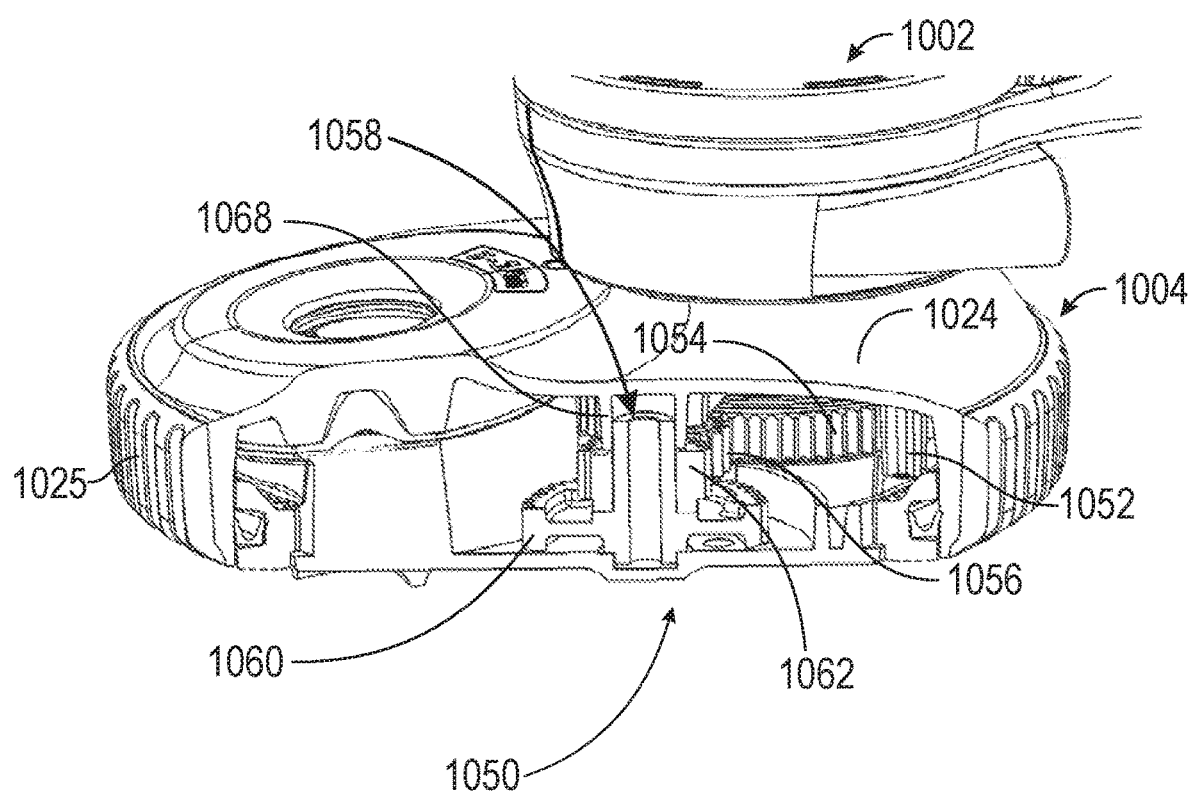
Figure 10B:
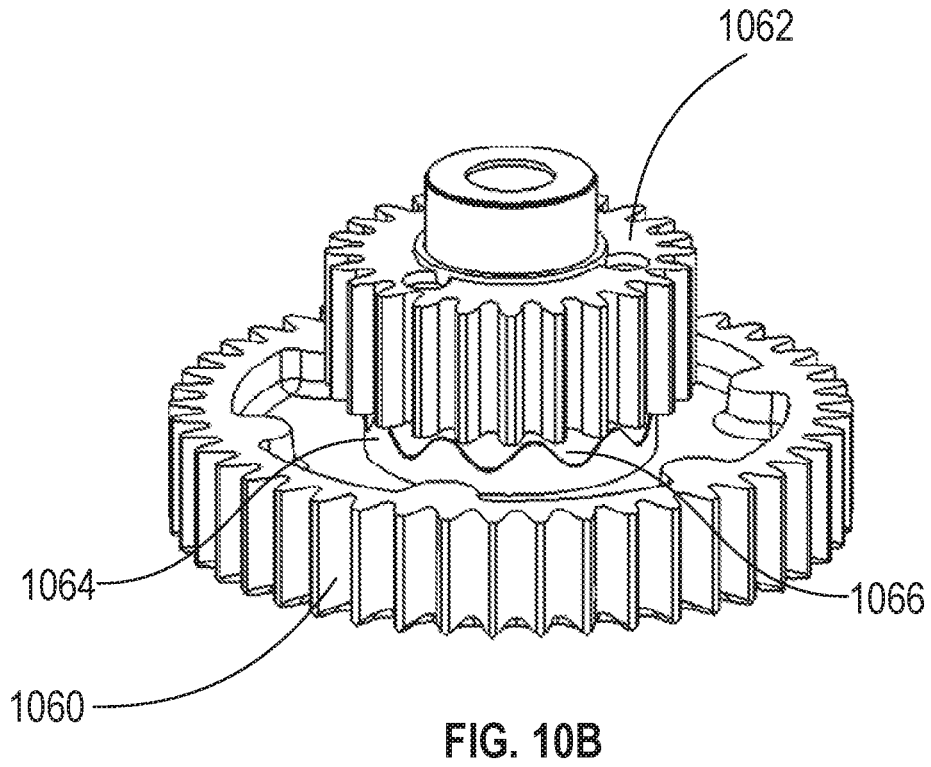
Figure 10C:
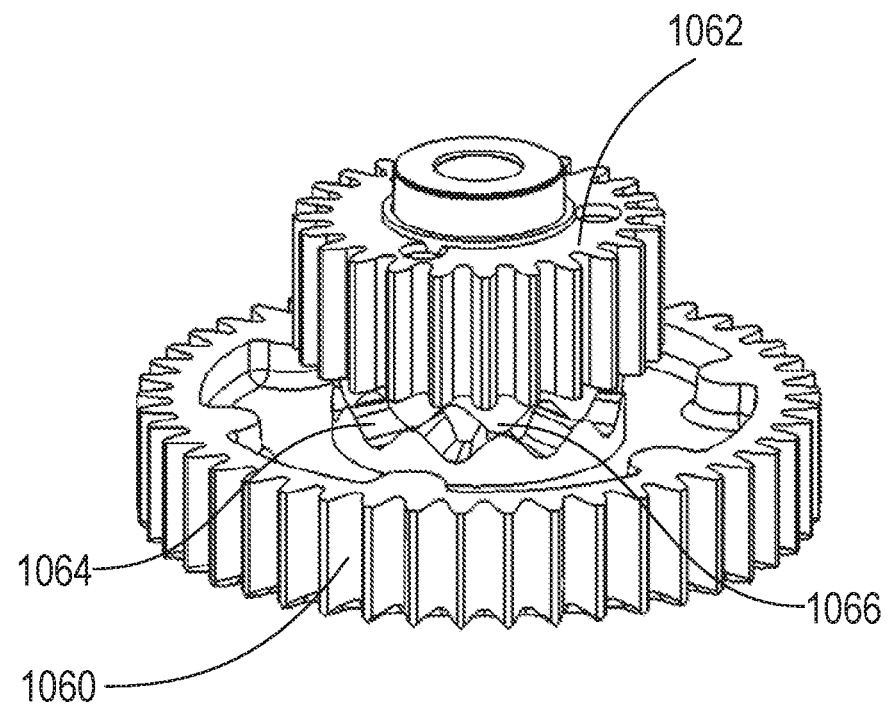

FIGS. 10A-10C depict an example medical device including a clutch in accordance with examples of this disclosure. FIG. 10A is a partial section view of example instrument access device 1000 including entry guide receptacle assembly 1002 and countermotion assembly 1004. Although not depicted in FIG. 10A, in examples, instrument access device 1000 can include an envelope and wound retractor clamp (serving as distal coupling component) substantially similar as described with reference to the examples of FIGS. 4A-4E. Countermotion assembly 1004 includes an orbital element 1024 in which the openings of the entry guide port and the assistant port are defined, an outer element 1025 received in the proximal opening of the envelope, and a countermotion mechanism that rotates the assistant port around the entry guide port without twisting the envelope about a central axis of the envelope. With regard to the countermotion mechanism of instrument access device 1000, the example of FIGS. 10A-10C is substantially similar in function, operation, and structure to the example of FIGS. 4A-4E. However, the countermotion mechanism of countermotion assembly 1004 includes a torque limiting clutch, which is configured to disengage counterrotation of the countermotion mechanism in response to a threshold applied torque.

It has been discovered that under certain circumstances, a clinician or other user may operate an instrument access device in accordance with this disclosure in a manner that applies a load on components of the countermotion assembly/mechanism of the device, which can break or otherwise cause the failure of one or more components of the countermotion assembly/mechanism. In some applications, for example, a user of an instrument access device, in the process of rotating the assistant port around the entry guide receptacle and entry guide port, may grab the envelope or a portion thereof and hold the envelope fixed to the outer element of the counterrotation assembly of the access device. When a user grabs the envelope in this manner, the envelope is essentially forced to rotate with the rotation of the assistant port around the entry guide receptacle and entry guide port. In these circumstances, the envelope pulls against the counterrotation action of the countermotion assembly/mechanism and places a relatively high load on the components of the device, which can lead to wear or failure of such components.

Referring to FIGS. 10A-10C, countermotion assembly 1004 includes gear train 1050, which is a mechanism by which the assistant port is able to rotate around the entry guide receptacle and entry guide port without the envelope rotating about a central axis of the envelope, or, in other words, without twisting the envelope. Gear train 1050 includes first gear 1052, second gear 1054, idler gear 1056, and intermediate gear 1058. Intermediate gear 1058 is a step spur gear including third spur gear 1060 and fourth spur gear 1062 engaged with idler gear 1056. As depicted in FIGS. 10B and 10C, third spur gear 1060 includes first face gear 1064 and fourth spur gear 1062 includes second face gear 1066. As illustrated by the example of FIGS. 10B and 10C, a face gear (sometimes referred to as a crown gear) is a gear which has teeth that project at right angles to the face of the cylindrical shaped gear component (versus the teeth of spur gear 1060 or 1062, which project generally parallel to the face). A face or crown gear is also defined as a type of bevel gear where the pitch cone angle is 90 degrees.

In the example of instrument access device 1000, first face gear 1064 of third spur gear 1060 is biased into engagement with second face gear 1066 of fourth spur gear 1062 by a section of orbital element 1024. As depicted in FIG. 10A, orbital element 1024 includes projections 1068, which extend distally from a proximal end of orbital element 1024 to abut fourth spur gear 1062. In operation at loads/torques below a threshold level, third and fourth spur gears 1060, 1062 are biased into engagement with one another by projections 1068 of orbital element 1024 and third and fourth spur gears 1060, 1062 rotate together.

In response to a load/torque above a threshold level, however, the load the user applies to the countermotion assembly 1004 overcomes the inherent spring force of orbital element 1024 to cause first face gear 1064 to slip relative to the second face gear 1066 and to thereby decouple third spur gear 1060 from fourth spur gear 1062. When third spur gear 1060 disengages from fourth spur gear 1062, the counterrotation of gear train 1050, which prevents the envelope from twisting, is disengaged and outer element 1025, orbital element 1024, and the envelope rotate around the entry guide port together in the same direction. The resilience of orbital element 1024, applied to fourth spur gear 1062 via projections 1068 functions to automatically reengage third and fourth spur gears 1060, 1062 and thus reengage the counterrotation of gear train 1050 upon removal of or reduction in the load/torque applied by the user.

Instrument access devices in accordance with this disclosure can include clutch or torque limiters that function similar to but are structured differently than the example clutch including first face gear 1064 of third spur gear 1060, second face gear 1066 of fourth spur gear 1062, and the resilient section of orbital element 1024. For example, third spur gear 1060 and fourth spur gear 1062 can be biased into engagement with one another by a spring disposed within a cavity of countermotion assembly 1004. As another example, FIGS. 11A and 11C depict an alternative clutch that can be employed in instrument access device 1000 to disengage the counterrotation of countermotion assembly 1004 (in particular, gear train 1050) in response to a threshold applied torque.

Figure 11A:
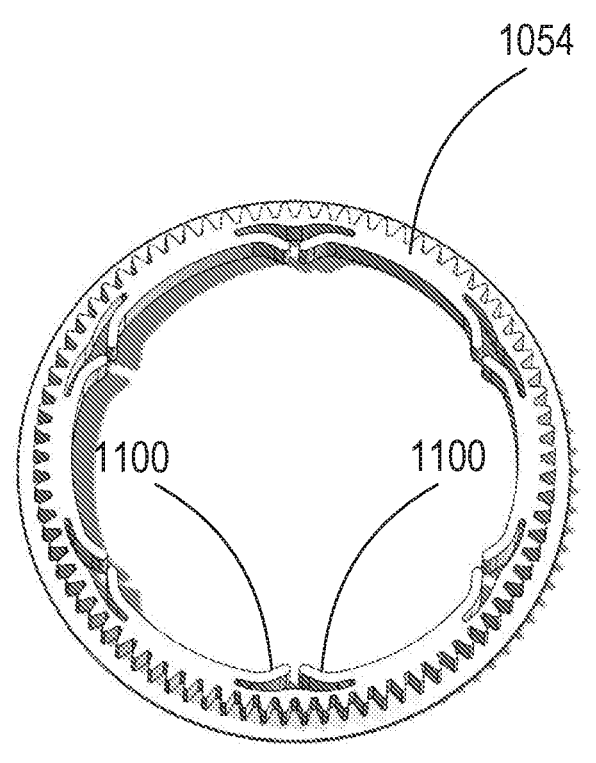
FIGS. 11A and 11B depict an alternative clutch that can be employed in instrument access device in accordance with examples of this disclosure.
Figure 11B:
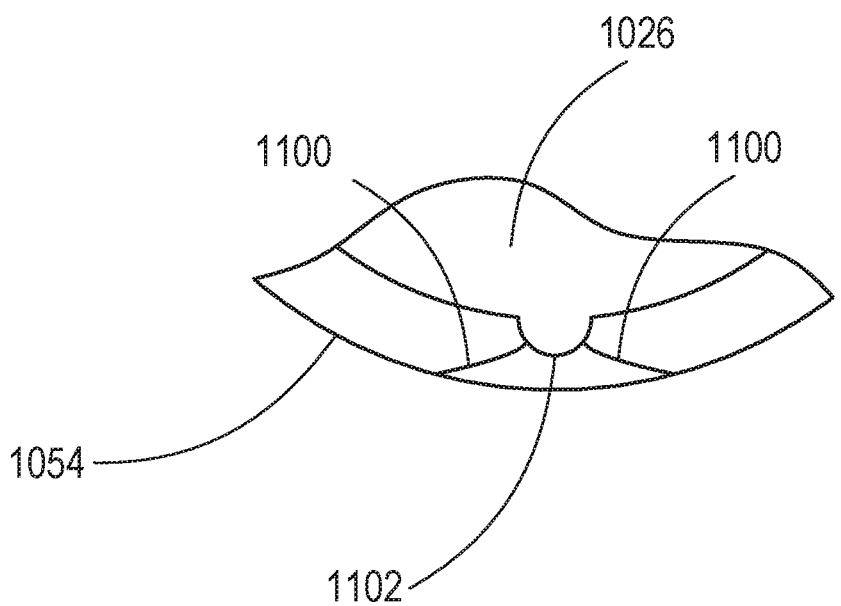

FIGS. 11A and 11B depict an alternative torque limiting clutch, which is configured to disengage the counterrotation of a countermotion assembly of an instrument access device in accordance with this disclosure. The clutch of FIGS. 11A and 11B can be implemented at the junction/coupling between second gear 1054 of gear train 1050 and the outer periphery of the entry guide receptacle of instrument access device 1000. FIG. 11A depicts example second gear 1054 with resilient fingers 1100 and FIG. 11B schematically depicts second gear 1054 assembled on the outer periphery of entry guide receptacle 1026, which includes protrusions 1102 on either side of which pairs of fingers 1100 are arranged.

In operation at loads/torques below a threshold level, second gear 1054 is configured to be fixedly coupled to entry guide receptacle 1026 such that second gear 1054 does not rotate around the entry guide receptacle periphery. Second gear 1054 includes a plurality of resilient fingers 1100 circumferentially distributed on an inner surface of the second gear to engage a plurality of protrusions 1102 circumferentially distributed on an outer surface of entry guide receptacle 1026. Fingers 1100 and protrusions 1000 are circumferentially distributed such that pairs of resilient fingers 1100 are disposed on opposing sides of each one of protrusions 1102 to hold second gear 1054 from rotating in response to a range of applied torques less than the threshold.

In response to a load/torque above a threshold level, however, the load the user applies overcomes the inherent spring force of fingers 1100 to cause the fingers to deflect radially outward and out of engagement with protrusions 1102. In such circumstances, second gear 1054 is freed to rotate relative to entry guide receptacle 1026, which, in turn, causes the counterrotation of the gear train to disengage in a similar manner as described above with reference to FIGS. 10A and 10B. To reengage the coupling between second gear 1054 and the outer periphery of entry guide receptacle 1026, second gear 1054 need only be rotated by a load/torque at least less than the threshold far enough for the pairs of fingers 1100 to become reengaged with each of protrusions 1102.

EXAMPLES

The following numbered examples are illustrative embodiments:

1. A medical device comprising: an envelope comprising a proximal opening; and a proximal coupling component in the proximal opening of the envelope; the proximal coupling component comprising: an outer element coupled to the envelope, an orbital element comprising a first opening and a second opening, an entry guide receptacle received in the first opening, and a gear train coupling the entry guide receptacle to the outer element; the gear train comprising: a first gear fixedly positioned in the proximal opening of the envelope, a second gear fixedly coupled to a periphery of the entry guide receptacle, and one or more intermediate gears engaged with the first and the second gears, the first gear being rotatable relative to the second gear without rotating around a central axis of the first gear, and the one or more intermediate gears being rotatable and translatable relative to the first gear and the second gear.

2. The medical device of example 1, wherein: the orbital element comprises a center; and the first and second openings are positioned eccentrically on the orbital element.

3. The medical device of example 1 or example 2, wherein: movement of the plurality of gears rotates the orbital element and the second port around the first port and the entry guide receptacle.

4. The medical device of any one of examples 1-3, wherein the one or more intermediate gears comprise: an idler gear; and an intermediate gear; the idler gear being engaged with the second gear and the intermediate gear; and the intermediate gear being engaged with the idler gear and the first gear.

5. The medical device of example 4, wherein: the intermediate gear comprises a step gear comprising a third gear and a fourth gear coupled to the third gear; the third gear is engaged with the first gear; and the fourth gear engaged with the idler gear.

6. The medical device of example 5, wherein: a gear ratio of the third gear to the fourth gear is equal to a gear ratio of the first gear to the second gear.

7. The medical device of example 5 or example 6, wherein: the first gear and the second gear are ring gears; and the idler gear and the intermediate gear are spur gears.

8. The medical device of any one of examples 1-3, wherein: the one or more intermediate gears comprise a step gear comprising a third gear and a fourth gear coupled to the third gear; the third gear being engaged with the first gear; and the fourth gear being engaged with the second gear.

9. The medical device of example 8, wherein: a gear ratio of the third gear to the fourth gear is equal to a gear ratio of the first gear to the second gear.

10. The medical device of example 8, wherein: the first gear and the second gear are ring gears; and the third gear and the fourth gear are spur gears.

11. The medical device of any one of examples 1-10, wherein: the envelope pressurized with insufflation gas comprises a spherical shape.

12. The medical device of any one of examples 1-10, wherein: the envelope pressurized with insufflation gas comprises an oblate spherical shape.

13. The medical device of any one of examples 1-10, wherein: the envelope pressurized with insufflation gas comprises a lenticular shape.

14. The medical device of any of examples 1-10, wherein: the envelope pressurized with insufflation gas comprises a barrel shape.

15. The medical device of any one of examples 1-10, wherein: the envelope pressurized with insufflation gas comprises a bellows shape.

16. The medical device of any one of examples 1-10, wherein: the envelope pressurized with insufflation gas comprises an ovoid shape.

17. The medical device of any one of examples 1-16, further comprising: a distal coupling component coupled to the distal opening of the envelope.

18. The medical device of example 17, wherein: the distal coupling component is configured to be coupled to a wound retractor assembly.

19. The medical device of any one of example 1-18, further comprising: a multiple instrument entry guide received in the entry guide receptacle.

20. The medical device of example 19, further comprising: an entry guide seal received in the entry guide receptacle; wherein the multiple instrument entry guide is received in and sealed by the entry guide seal.

21. The medical device of any one of examples 1-20, further comprising: an instrument seal received in the second port.

22. The medical device of any one of examples 1-21, further comprising: a third port in the envelope between the proximal opening and the distal opening of the envelope.

23. The medical device of example 22, further comprising: an instrument seal received in the third port.

24. A medical device comprising: an envelope comprising a proximal opening; and a proximal coupling component in the proximal opening of the envelope; the proximal coupling component comprising: an inner hub comprising a first opening and a second opening, an outer rim coupled to the envelope and surrounding the inner hub, an entry guide receptacle received in the first opening, and a crank arm pivotally connected to the outer rim and the entry guide receptacle, the inner hub being rotatable relative to the outer rim, the inner hub, the outer rim, the entry guide receptacle, and the crank arm being connected to one another to define a linkage, and movement of the linkage rotating the inner hub and the second opening around the first opening and the entry guide receptacle.

25. The medical device of example 24, wherein: the inner hub comprises a center; and the first and second openings are positioned eccentrically on the inner hub.

26. The medical device of example 24 ore example 25, wherein: the linkage is a 4-bar linkage.

27. The medical device of example 26, wherein: a ground link of the 4-bar linkage comprises the entry guide receptacle.

28. The medical device of example 26 or example 27, wherein: a coupler link of the 4-bar linkage comprises the outer rim.

29. The medical device of any one of examples 26-28, wherein: a coupler link of the 4-bar linkage comprises the inner hub.

30. The medical device of any one of examples 26-29, wherein: an input link of the 4-bar linkage comprises the crank arm.

31. The medical device of any one of examples 26-30, wherein: the linkage comprises a parallel linkage.

32. The medical device of any one of examples 24-31, wherein: pivoting of the crank arm causes the inner hub to rotate relative to the outer rim.

33. The medical device of example 32, wherein: pivoting of the crank arm causes the outer rim to translate without rotating around a central axis of the outer rim.

34. A medical device comprising: means for enclosing a cavity, the means for enclosing comprising a proximal opening and central longitudinal axis defined through the proximal opening; means for receiving one or more instruments, the means for receiving being fixed in the proximal opening of the means for enclosing, and the means for receiving comprising a first port and a second port; and means for rotating the second port around the first port without twisting the means for enclosing around the central longitudinal axis.

35. The medical device of example 34, wherein: the means for enclosing comprises a distal opening; and the central longitudinal axis is defined through the distal opening.

36. The instrument a medical access device of example 34 or example 35, wherein: the means for rotating comprises a gear train; and movement of the gear train rotates the second port around the first port without twisting the means for enclosing around the central longitudinal axis.

37. The medical device of example 34 or example 35, wherein: the means for rotating comprises a linkage; and movement of the linkage rotates the second port around the first port without twisting the means for enclosing around the central longitudinal axis.

38. The medical device of example 34, wherein: the means for receiving comprises: an orbital element fixedly coupled to the means for enclosing, the orbital element comprising the first port and the second port, and an entry guide receptacle received in the first port; and the means for rotating comprises: a gear train connecting the orbital element to the entry guide receptacle, wherein movement of the gear train rotates the orbital element and the second port around the first port and the entry guide receptacle.

39. The medical device of example 34, wherein: the means for receiving comprises: an inner hub comprising the first port and the second port, an outer rim coupled to the means for enclosing, the outer rim surrounding the inner hub, an entry guide receptacle received in the first port, and a crank arm pivotally connected to the inner hub and the outer rim; and the means for rotating comprises: a linkage defined by the inner hub, the outer rim, the entry guide receptacle, and the crank arm, wherein movement of the linkage rotates the inner hub and the second port around the first port and the entry guide receptacle.

40. A medical device comprising: an envelope comprising a proximal opening; means for countermotion comprising: an outer element fixedly coupled to the envelope at the proximal opening, an orbital element surrounded by the outer element, a first instrument port in the orbital element, a second instrument port in the orbital element, means for fixing the first instrument port at a fixed location in space, and means for counterrotating the outer element around the orbital element in a first angular displacement in a first direction as the second instrument port rotates around the first instrument port in a second angular displacement in a second direction, the second angular displacement being equal to the first angular displacement, and the second direction being opposite the first direction.

41. The medical device of example 40, wherein: the envelope comprises a distal opening opposite the proximal opening; the medical device further comprises means for clamping a port device; and the means for clamping is fixedly coupled to the envelope at the distal opening.

42. The medical device of example 40 or example 41, wherein: the means for counterrotating comprises gear means.

43. The medical device of example 40 or example 41, wherein: the means for counterrotating comprises bar linkage means.

44. A medical device comprising: an envelope comprising a proximal opening; and a proximal coupling component in the proximal opening of the envelope, wherein the proximal coupling component comprises: an outer element coupled to the envelope; an orbital element surrounded by the outer element and comprising a first opening and a second opening; an instrument entry guide receptacle received in the first opening; and a mechanism coupling the entry guide receptacle to the outer element, wherein the mechanism comprises a clutch, wherein on condition a first torque below a threshold torque urges the orbital element to rotate in a first direction, the mechanism rotates the orbital element and the second opening around the first opening in the first direction and counterrotates the outer element and the envelope around the orbital element in a second direction opposite the first direction; and wherein on condition a second torque above the threshold torque urges the orbital element to rotate in the first direction, the mechanism rotates the orbital element and the second opening around the first opening in the first direction, and the clutch disengages the counterrotation of the outer element and the envelope in the second direction.

45. The medical device of claim 44, wherein: the mechanism comprises a gear train coupling the entry guide receptacle to the outer element.

46. The medical device of claim 45, wherein: the gear train comprises: a first gear fixedly positioned in the proximal opening of the envelope; a second gear coupled to a periphery of the entry guide receptacle; and one or more intermediate gears engaged with the first and the second gears, the first gear is rotatable relative to the second gear without rotating around a central axis of the first gear, and the one or more intermediate gears are rotatable and translatable relative to the first gear and the second gear.

47. The medical device of claim 46, wherein: the one or more intermediate gears comprise the clutch; and the clutch is configured to disengage the one or more intermediate gears from the first gear in response to the second torque.

48. The medical device of claim 47, wherein: the one or more intermediate gears comprise a step spur gear, the step spur gear comprises a third gear and a fourth gear; the clutch comprises a first face gear biased into engagement with a second face gear by a resilient member, the first face gear being on the third gear of the step spur gear, and the second face gear being on the fourth gear of the step spur gear; and on the condition the first torque urges the orbital element to rotate in the first direction, a spring force of the resilient member biases the first face gear into engagement with the second face gear and the third gear and the fourth gear rotate synchronously; and on the condition the second torque urges the orbital element to rotate in the first direction, and the spring force of the resilient member is overcome and the first face gear slips relative to the second face gear.

49. The medical device of claim 48, wherein: the proximal coupling component comprises a cavity, and the step spur gear is in the cavity; the orbital element defines a proximal wall of the cavity; and the resilient member comprises a portion of the orbital element that deflects in response to the second torque.

50. The medical device of claim 46, wherein: the clutch couples the second gear to the periphery of the entry guide receptacle; and the clutch is configured to disengage the counterrotation of the mechanism in response to the second torque by decoupling the second gear from the periphery of the entry guide receptacle such that the second gear rotates relative to the entry guide receptacle.

51. The medical device of claim 50, wherein the clutch comprises: a protrusion on the outer surface of the entry guide receptacle; at least one resilient finger is on an inner surface of the second gear, wherein on the condition the first torque urges the orbital element to rotate in the first direction, the at least one resilient finger engages the protrusion to prevent the second gear from rotating relative to the entry guide receptacle, and wherein on the condition the second torque urges the orbital element to rotate in the first direction, the at least one resilient finger deflects out of engagement with the protrusion and the second gear rotates relative to the entry guide receptacle.

52. The medical device of claim 51, wherein: the at least one resilient finger comprises a first resilient finger and a second resilient finger; the protrusion comprises a first side and a second side opposite the first side; the first resilient finger is on the first side of the protrusion; and the second resilient finger is on the second side of the protrusion; on the condition the first torque urges the orbital element to rotate in the first direction, the first and second resilient fingers engage the protrusion to prevent the second gear from rotating relative to the entry guide receptacle; and on the condition the second torque urges the orbital element to rotate in the first direction, the first and second resilient fingers deflect out of engagement with the protrusion and the second gear rotates relative to the entry guide receptacle.

53. The medical device of claim 46, wherein: the one or more intermediate gears comprise a step spur gear; the step spur gear comprises a third gear and a fourth gear coupled to the third gear; the third gear is engaged with the first gear; and the fourth gear is engaged with the second gear.

54. The medical device of claim 53, wherein: a gear ratio of the third gear to the fourth gear is equal to a gear ratio of the first gear to the second gear.

55. The medical device of claim 53, wherein: the first gear and the second gear are ring gears; and the third gear and the fourth gear are spur gears.

56. The medical device of any of claims 44-55, wherein: the orbital element comprises a center; and the first and second openings are positioned eccentrically on the orbital element.

57. The medical device of any one of claims 44-55, wherein: the envelope comprises a distal opening; and the medical device further comprises a distal coupling component coupled to the distal opening of the envelope.

58. The medical device of claim 57, wherein: the distal coupling component is configured to be coupled to a wound retractor assembly.

59. The medical device of any one of claims 44-55, further comprising: a multiple instrument entry guide received in the entry guide receptacle.

60. The medical device of claim 59, further comprising: an entry guide seal received in the entry guide receptacle; wherein the multiple instrument entry guide is received in and sealed by the entry guide seal.

61. The medical device of any one of claims 46-55, further comprising: an instrument port in the envelope between the proximal opening and a distal opening of the envelope.

62. A medical device comprising: means for enclosing a cavity, the means for enclosing comprising a proximal opening and central longitudinal axis defined through the proximal opening; means for receiving one or more instruments, the means for receiving being in the proximal opening of the means for enclosing, and the means for receiving comprising a first port and a second port; means for rotating the second port around the first port without twisting the means for enclosing around the central longitudinal axis; and means for disengaging at least a portion of the means for rotating in response to a threshold applied torque.

63. The medical device of claim 62, wherein: on the condition the at least a portion of the means for rotating is disengaged in response to the threshold applied torque, the second port rotates around the first port and the means for enclosing twists around the central longitudinal axis.

64. The medical device of claim 62, wherein: the means for receiving comprises a center; the central longitudinal axis intersects the center; and the first and second openings are positioned eccentrically on the means for receiving.

65. The medical device of any one of claims 62-64, wherein: the means for rotating comprises a gear train, and the gear train comprises a step spur gear comprising a third gear and a fourth gear; the means for disengaging comprises a first face gear, a second face gear, and a resilient member that biases the first face gear into engagement with the second face gear; the first face gear is on the third gear of the step spur gear, and the second face gear is on the fourth gear of the step spur gear; and on the condition the at least a portion of the means for rotating is disengaged in response to the threshold applied torque, a spring force of the resilient member is overcome and the first face gear slips relative to the second face gear.

66. The medical device of any one of claims 62-64, wherein: the means for rotating comprises a gear train, and the gear train comprises a gear fixedly coupled to a periphery of an instrument receptacle in the first port; and the means for disengaging comprises a protrusion on the periphery of the instrument receptacle and at least one resilient finger on an inner surface of the gear and engaged with the protrusion to prevent the gear from rotating relative to the instrument receptacle; and on the condition the at least a portion of the means for rotating is disengaged in response to the threshold applied torque, the resilient finger disengages from the protrusion and the gear rotates relative to the instrument receptacle.

Persons of skill in the art will understand that any of the features described above may be combined with any of the other example features, as long as the features are not mutually exclusive. All possible combinations of features are contemplated, depending on clinical or other design requirements.

The examples (e.g., methods, systems, or devices) described herein may be applicable to surgical procedures, non-surgical medical procedures, diagnostic procedures, cosmetic procedures, and non-medical procedures or applications. The examples may also be applicable for training, or for obtaining information, such as imaging procedures. The examples may be applicable to handling of tissue that has been removed from human or animal anatomies and will not be returned to a human or animal, or for use with human or animal cadavers.

The above detailed description includes references to the accompanying drawings, which form a part of the detailed description. The drawings show, by way of illustration, specific embodiments in which the invention may be practiced. These embodiments are also referred to herein as "examples." Such examples may include elements in addition to those shown or described. But, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round", a component that is not precisely circular (e.g., one that is slightly oblong or is a many-sided polygon) is still encompassed by this description. Coordinate systems or reference frames are provided for aiding explanation, and implantations may use other reference frames or coordinate systems other than those described herein.

The above description is intended to be illustrative, and not restrictive. For example, the above-described examples (or one or more aspects thereof) may be used in combination with each other. Other embodiments may be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments may be combined with each other in various combinations or permutations. The scope of the invention should be determined with reference to the appended claims, along with the full scope of equivalents to which such claims are entitled.

The claimed invention is:

1. A medical device comprising:
an envelope comprising a proximal opening; and
a proximal coupling component in the proximal opening of the envelope;
the proximal coupling component comprising:
an outer element coupled to the envelope,
an orbital element comprising a first opening and a second opening,
an entry guide receptacle received in the first opening, and
a gear train coupling the entry guide receptacle to the outer element;
the gear train comprising:
a first gear fixedly positioned in the proximal opening of the envelope,
a second gear fixedly coupled to a periphery of the entry guide receptacle, and
one or more intermediate gears engaged with the first and the second gears,
the first gear being rotatable relative to the second gear without rotating around a central axis of the first gear, and
the one or more intermediate gears being rotatable and translatable relative to the first gear and the second gear.

2. The medical device of claim 1, wherein:
the orbital element comprises a center; and
the first and second openings are positioned eccentrically on the orbital element.

3. The medical device of claim 1, wherein:
movement of the first gear, the second gear, and the one or more intermediate gears rotate the orbital element and the second opening around the first opening and the entry guide receptacle.

4. The medical device of claim 1, wherein the one or more intermediate gears comprise:
an idler gear; and
an intermediate gear;
the idler gear being engaged with the second gear and the intermediate gear; and
the intermediate gear being engaged with the idler gear and the first gear.

5. The medical device of claim 4, wherein:
the intermediate gear comprises a step gear comprising a third gear and a fourth gear coupled to the third gear;
the third gear is engaged with the first gear; and
the fourth gear engaged with the idler gear.

6. The medical device of claim 5, wherein:
a gear ratio of the third gear to the fourth gear is equal to a gear ratio of the first gear to the second gear.

7. The medical device of claim 5, wherein:
the first gear and the second gear are ring gears; and
the idler gear and the intermediate gear are spur gears.

8. The medical device of claim 1, wherein:
the one or more intermediate gears comprise a step gear comprising a third gear and a fourth gear coupled to the third gear;
the third gear being engaged with the first gear; and
the fourth gear being engaged with the second gear.

9. The medical device of claim 8, wherein:
a gear ratio of the third gear to the fourth gear is equal to a gear ratio of the first gear to the second gear.

10. The medical device of claim 8, wherein:
the first gear and the second gear are ring gears; and
the third gear and the fourth gear are spur gears.

11. The medical device of claim 1, wherein:
the envelope pressurized with insufflation gas comprises a spherical shape.

12. The medical device of claim 1, wherein:
the envelope pressurized with insufflation gas comprises an oblate spherical shape.

13. The medical device of claim 1, wherein:
the envelope pressurized with insufflation gas comprises a lenticular shape.

14. The medical device of claim 1, wherein:
the envelope pressurized with insufflation gas comprises a barrel shape.

15. The medical device of claim 1, wherein:
the envelope pressurized with insufflation gas comprises a bellows shape.

16. The medical device of claim 1, wherein:
the envelope pressurized with insufflation gas comprises an ovoid shape.

17. The medical device of claim 1, further comprising:
a distal coupling component coupled to a distal opening of the envelope.

18. The medical device of claim 17, wherein:
the distal coupling component is configured to be coupled to a wound retractor assembly.

19. The medical device of claim 1, further comprising:
a multiple instrument entry guide received in the entry guide receptacle.

20. The medical device of claim 19, further comprising:
an entry guide seal received in the entry guide receptacle;
wherein the multiple instrument entry guide is received in and sealed by the entry guide seal.

21. The medical device of claim 1, wherein:
movement of the gear train rotates the orbital element and the second opening around the first opening and the entry guide receptacle.

* * * * *